(12) United States Patent
Haskell-Luevano et al.

(10) Patent No.: US 11,932,628 B2
(45) Date of Patent: Mar. 19, 2024

(54) SELECTIVE SMALL MOLECULE PEPTIDOMIMETIC MELANOCORTIN LIGANDS

(71) Applicants: REGENTS OF THE UNIVERSITY OF MINNESOTA, Minneapolis, MN (US); TORREY PINES INSTITUTE FOR MOLECULAR STUDIES, Port St. Lucie, FL (US)

(72) Inventors: Carrie Haskell-Luevano, Minneapolis, MN (US); Skye Ross Doering, Minneapolis, MN (US); Marcello A. Giulianotti, Port St. Lucie, FL (US); Clemencia Pinilla, Port St. Lucie, FL (US); Radleigh G. Santos, Port St. Lucie, FL (US); Richard A. Houghten, Port St. Lucie, FL (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 10 days.

(21) Appl. No.: 17/567,201

(22) Filed: Jan. 3, 2022

(65) Prior Publication Data
US 2022/0213068 A1    Jul. 7, 2022

Related U.S. Application Data

(60) Provisional application No. 63/133,571, filed on Jan. 4, 2021.

(51) Int. Cl.
| | | |
|---|---|---|
| *C07D 403/14* | (2006.01) | |
| *A61K 9/20* | (2006.01) | |
| *A61K 9/48* | (2006.01) | |
| *A61P 3/04* | (2006.01) | |

(52) U.S. Cl.
CPC .......... *C07D 403/14* (2013.01); *A61K 9/2013* (2013.01); *A61K 9/2027* (2013.01); *A61K 9/2054* (2013.01); *A61K 9/2059* (2013.01); *A61K 9/485* (2013.01); *A61K 9/4858* (2013.01); *A61K 9/4866* (2013.01); *A61P 3/04* (2018.01)

(58) Field of Classification Search
CPC .................................................. C07D 403/14
See application file for complete search history.

(56) References Cited

U.S. PATENT DOCUMENTS

| | | | |
|---|---|---|---|
| 6,613,874 B1 | 9/2003 | Mazur et al. | |
| 7,307,063 B2 | 12/2007 | Sharma et al. | |
| 10,899,793 B2 | 1/2021 | Haskell-Luevano et al. | |
| 11,124,541 B2 | 9/2021 | Haskell-Luevano et al. | |
| 2017/0342107 A1 | 11/2017 | Haskell-Luevano et al. | |
| 2018/0360972 A1 | 12/2018 | Haskell-Luevano et al. | |
| 2020/0115416 A1 | 4/2020 | Haskell-Luevano et al. | |
| 2021/0179666 A1 | 6/2021 | Haskell-Luevano et al. | |

FOREIGN PATENT DOCUMENTS

WO   2013134376 A1   9/2013

OTHER PUBLICATIONS

American Chemical Society. Chemical Abstract Service. RN 913559-17-8. Entered into STN: Nov. 17, 2006. (Year: 2006).*
Hensler, Mary E., et al. "Pyrrolidine bis-cyclic guanidines with antimicrobial activity against drug-resistant Gram-positive pathogens identified from a mixture-based combinatorial library." Bioorganic & Medicinal Chemistry Letters. (2006), 16, pp. 5073-5079. (Year: 2006).*
Doering, S , et al., "Discovery of Mixed Pharmacology Melanocortin-3 Agonists and Melanocortin-4 Receptor Tetrapeptide Antagonist Compounds (TACOs) Based on the Sequence Ac-Xaa1-Arg-(pI)DPhe-Xaa4-NH2", J Med Chem 60(10), 4342-4357 (2017).
Doering, S , et al., "Discovery of Nanomolar Melanocortin-3 Receptor (MC3R)-Selective Small Molecule Pyrrolidine Bis-Cyclic Guanidine Agonist Compounds Via a High-Throughput "Unbiased" Screening Campaign", J Med Chem 64, 5577-5592 (2021).
Dong, H , et al., "Identification of Small Molecule Inhibitors of Human As(III) S-Adenosylmethionine Methyltransferase (AS3MT)", Chem Res Toxicol 28, 2419-2425 (2015).
Ericson, M , et al., "Functional Mixture-Based Positional Scan Identifies a Library of Antagonist Tetrapeptide Sequences (LAtTeS) with Nanomolar Potency for the Melanocortin-4 Receptor and Equipotent with the Endogenous AGRP(86-132) Antagonist", J Med Chem 64, 14860-14875 (2021).
Fleeman, R , et al., "Combinatorial Libraries As a Tool for the Discovery of Novel, Broad-Spectrum Antibacterial Agents Targeting the ESKAPE Pathogens", J Med Chem 58, 3340-3355 (2015).
Haslach, E M , et al., "Identification of Tetrapeptides from a Mixture Based Positional Scanning Library That Can Restore nM Full Agonist Function of the L106P, I69T, I102S, A219V, C271Y, and C271R Human Melanocortin-4 Polymorphic Receptors (hMC4Rs)", J. Med. Chem. 57(11), 4615-4628 (2014).

(Continued)

*Primary Examiner* — John S Kenyon
(74) *Attorney, Agent, or Firm* — Viksnins Harris Padys Malen LLP

(57) ABSTRACT

The invention provides compounds having the general formula I:

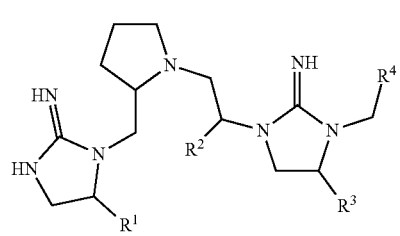

and salts thereof, wherein the variables $R^1$, $R^2$, $R^3$ and $R^4$ have the meaning as described herein, and compositions containing such compounds and methods for using such compounds and compositions.

22 Claims, 18 Drawing Sheets

(56) References Cited

OTHER PUBLICATIONS

Hensler, M, et al., "Pyrrolidine bis-cyclic guanidines with antimicrobial activity against drug-resistant Gram-positive pathogens identified from a mixture-based combinatorial library", Bioorganic & Medicinal Chemistry Letters 16, 5073-5079 (2006).
Houghten, R, et al., "Mixture-Based Synthetic Combinatorial Libraries", J. Med. Chem. 42(19), 3743-3778 (1999).
Houghten, R, et al., "Strategies for the Use of Mixture-Based Synthetic Combinatorial Libraries: Scaffold Ranking, Direct Testing In Vivo, and Enhanced Deconvolution by Computational Methods", J. Comb. Chem. 10(1), 3-19 (2008).
Singh, A, et al., "Synthesis and pharmacology of $\alpha/\beta 3$-peptides based on the melanocortin agonist Ac-His-d Phe-Arg-Trp-NH2 sequence.", ACS Med Chem Lett 6(5), 568-572 (2015).
Yitzhaki, S, et al., "Similarities between Exogenously- and Endogenously-Induced Envelope Stress: The Effects of a New Antibacterial Molecule, TPI1609-10", PLOS One 7(10), e44896, 15 pages (2012).

\* cited by examiner

SELECTIVE SMALL MOLECULE PEPTIDOMIMETIC MELANOCORTIN LIGANDS

CROSS REFERENCE TO RELATED APPLICATIONS

This non-provisional application claims the benefit of priority to U.S. Provisional Application No. 63/133,571, filed 4 Jan. 2021, which is incorporated by reference in its entirety.

GOVERNMENT FUNDING

This invention was made with government support under DK091906 awarded by the National Institutes of Health. The government has certain rights in the invention.

BACKGROUND OF THE INVENTION

The melanocortin system consists of five receptors, discovered to date, that are members of the family of G protein-coupled receptors (GPCRs), endogenous agonists including the α-melanocyte stimulating hormone (MSH), β-MSH, γ-MSH, and adrenocorticotropic hormone (ACTH) derived from the proopiomelanocortin (POMC) gene transcript, and the naturally occurring antagonists agouti and agouti-related protein. These receptors and ligands may be important in numerous biological pathways, including pigmentation, steroidogenesis, and energy homeostasis. MC3R/MC4R antagonists increase food consumption. With global obesity rates increasing, the development of novel probes to investigate the etiology of obesity and serve as potential therapeutic leads may be important in efforts to decrease this trend.

Both the melanocortin-3 and melanocortin-4 receptors are found in the brain and they modulate body weight. It has been hypothesized the melanocortin-4 receptor effects immediate satiety whereas the melanocortin-3 receptor effects the long-term energy needs and food consumption in the body. While MC4R-selective agonists based upon the endogenous melanocortin agonists have previously been investigated, off-target effects including increased blood pressure and increased erectile activity have limited their clinical utility.

Mixture-based combinatorial library technology has been applied to the melanocortin system in the identification of tetrapeptide ligands which rescued the function of known MC4R single nucleotide polymorphisms, and ligands which demonstrate mixed mouse (m)MC3R agonist and mouse (m)MC4R antagonist pharmacology (Houghten, R. A., et al, *J. Med. Chem.* (1999) 42 (19):3743-3778; Pinilla, C., et al, *Nat. Med.* (2003) 9 (1):118-122; Houghten, R. A., et al, *J. Comb. Chem.* (2008) 10 (1):3-19; Haslach, E. M., et al, *J. Med. Chem.* (2014) 57 (11):4615-4628; Doering, S. R.; et al (2017) *J. Med. Chem.* 60:4342-4357).

There is a need for selective melanocortin ligands. Specifically, there is a need for new compounds that selectively activate MC3R and simultaneously block the activation of MC4R.

SUMMARY OF THE INVENTION

This invention provides selective melanocortin ligands. Accordingly, the invention provides a compound of formula I:

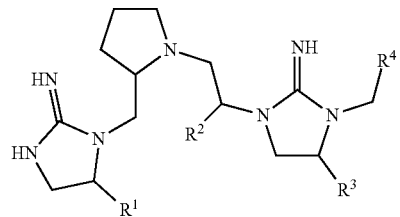

wherein:
R$^1$ is H, C$_{1-30}$ alkyl or -L$^1$-A$^1$; wherein the C$_{1-30}$ alkyl is optionally substituted with one or more groups selected from the group consisting of halo, hydroxy, nitro, cyano, C$_{1-6}$ alkoxy, —NR$^a_2$, —NHC(=NH)NR$^a_2$, —C(=O)NR$^a_2$, —COOR$^a$, and —SR$^a$;

R$^2$ is H, C$_{1-8}$ alkyl or -L$^2$-A$^2$; wherein the C$_{1-8}$ alkyl is optionally substituted with one or more groups selected from the group consisting of halo, hydroxy, nitro, cyano, C$_{1-6}$ alkoxy, —NR$^b_2$, —NHC(=NH)NR$^b_2$, —C(=O)NR$^b_2$, —COOR$^b$, and —SR$^b$;

R$^3$ is H, C$_{1-30}$ alkyl or -L$^3$-A$^3$; wherein the C$_{1-30}$ alkyl is optionally substituted with one or more groups selected from the group consisting of halo, hydroxy, nitro, cyano, C$_{1-6}$ alkoxy, —NR$^c_2$, —NHC(=NH)NR$^c_2$, —C(=O)NR$^c_2$, —COOR$^c$, and —SR$^c$;

R$^4$ is H, C$_{1-30}$ alkyl or -L$^4$-A$^4$; wherein the C$_{1-30}$ alkyl is optionally substituted with one or more groups selected from the group consisting of halo, hydroxy, nitro, cyano, C$_{1-6}$ alkoxy, —NR$^d_2$, —NHC(=NH)NR$^d_2$, —C(=O)NR$^d_2$, —COOR$^d$, and —SR$^d$;

L$^1$ is absent or C$_{1-4}$ alkylene;
L$^2$ is absent or C$_{1-4}$ alkylene;
L$^3$ is absent or C$_{1-4}$ alkylene;
L$^4$ is absent or C$_{1-4}$ alkylene;
A$^1$ is cycloalkyl, aryl, or heteroaryl; wherein the cycloalkyl, aryl, and heteroaryl are optionally substituted with one or more groups selected from the group consisting of halo, hydroxy, nitro, cyano, C$_{1-6}$ alkyl, C$_{1-6}$ alkoxy, C$_{1-6}$haloalkyl, C$_{1-6}$ haloalkoxy, and phenyl;
A$^2$ is cycloalkyl, aryl, or heteroaryl; wherein the cycloalkyl, aryl, and heteroaryl are optionally substituted with one or more groups selected from the group consisting of halo, hydroxy, nitro, cyano, C$_{1-6}$ alkyl, C$_{1-6}$ alkoxy, C$_{1-6}$ haloalkyl, C$_{1-6}$ haloalkoxy, and phenyl;
A$^3$ is cycloalkyl, aryl, or heteroaryl; wherein the cycloalkyl, aryl, and heteroaryl are optionally substituted with one or more groups selected from the group consisting of halo, hydroxy, nitro, cyano, C$_{1-6}$ alkyl, C$_{1-6}$ alkoxy, C$_{1-6}$ haloalkyl, C$_{1-6}$ haloalkoxy, and phenyl;
A$^4$ is cycloalkyl, aryl, or heteroaryl; wherein the cycloalkyl, aryl, and heteraryl are optionally substituted with one or more groups selected from the group consisting of halo, hydroxy, nitro, cyano, C$_{1-6}$ alkyl, C$_{1-6}$ alkoxy, C$_{1-6}$ haloalkyl, C$_{1-6}$ haloalkoxy, and phenyl;
each R$^a$ is independently H or C$_{1-6}$ alkyl;
each R$^b$ is independently H or C$_{1-6}$ alkyl;
each R$^c$ is independently H or C$_{1-6}$ alkyl; and
each R$^d$ is independently H or C$_{1-6}$ alkyl;
or a salt thereof.

The invention also provides a pharmaceutical composition comprising a compound of formula I or a pharmaceutically acceptable salt thereof, and a pharmaceutically acceptable excipient.

The invention also provides a method for treating obesity or a disease associated with obesity in an animal (e.g., a mammal, such as a human) comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of obesity or a disease associated with obesity.

The invention also provides the use of a compound of formula I or a pharmaceutically acceptable salt thereof to prepare a medicament for treating obesity or a disease associated with obesity.

The invention also provides processes and intermediates disclosed herein that are useful for preparing a compound of formula I or a salt thereof.

DETAILED DESCRIPTION

Figure 1:
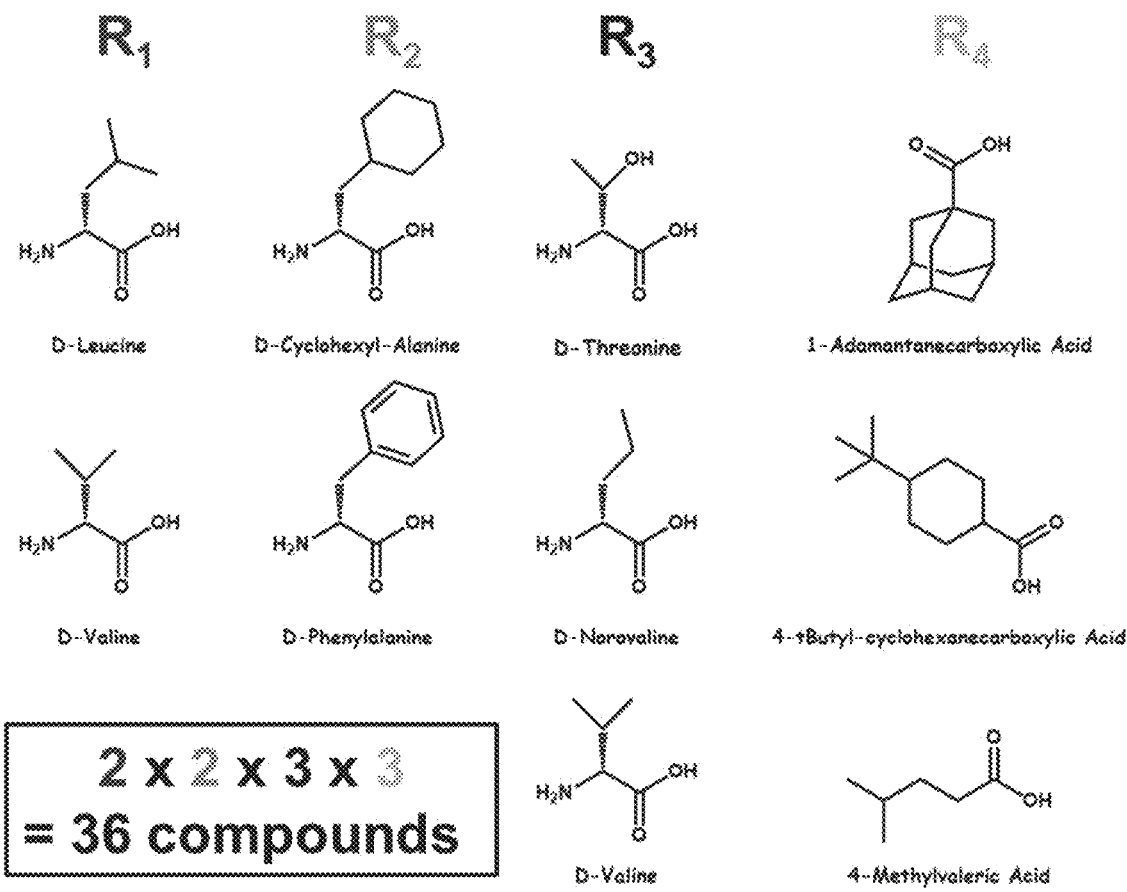
FIG. 1 illustrates the structures substituents R1, R2, R3, R4 of exemplary active hits of formula I compounds from the positional scanning assay.
Figure 2:
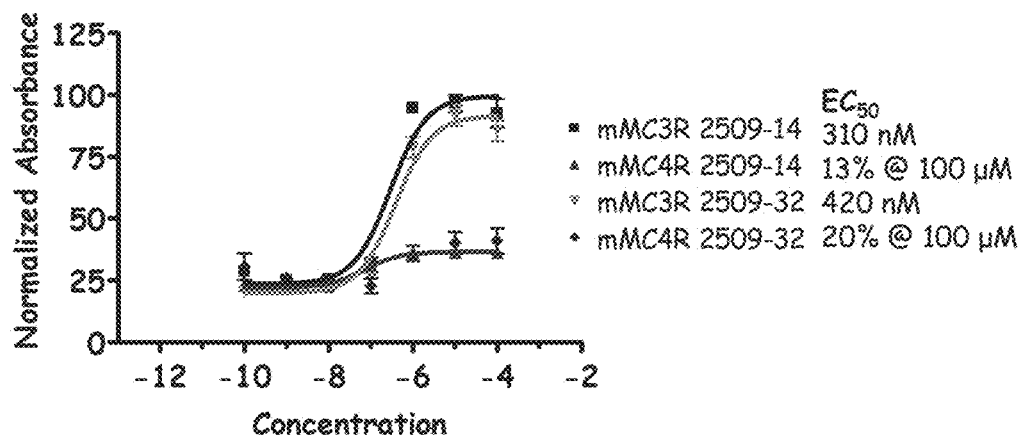
FIG. 2 illustrates a dose-response curve for compounds TPI2509-14 and TPI2509-32.

The term "halo" means fluoro, chloro, bromo, or iodo.

The term "alkyl", by itself or as part of another substituent, means, unless otherwise stated, a straight or branched chain hydrocarbon radical, having the number of carbon atoms designated (i.e., $C_{1-8}$ means one to eight carbons and $C_{1-30}$ means one to thirty carbons). Examples include ($C_1$-$C_8$) alkyl, ($C_2$-$C_8$) alkyl, $C_1$-$C_6$) alkyl, ($C_2$-$C_6$) alkyl and ($C_3$-$C_6$)alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and higher homologs and isomers. Alkyl groups can be unsubstituted or substituted with one or more groups independently selected from carboxyl, halo, hydroxy, amino, oxo (=O), alkylamino, amido, acyl, nitro, cyano, and alkoxy, including fatty acids where the alkyl radical terminates in a carboxylic acid group.

The term "alkenyl" refers to a straight (linear) or branched, unsaturated, aliphatic radical having the number of carbon atoms indicated and at least one carbon-carbon double bond, sp2. Alkenyl can include from two to about 30 or more carbons atoms. Alkenyl groups are radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$). butenyl, pentenyl, and isomers thereof. Alkenyl groups can be unsubstituted or substituted with one or more groups independently selected from carboxyl, halo, hydroxy, amino, oxo (=O), alkylamino, amido, acyl, nitro, cyano, and alkoxy, including fatty acids where the alkenyl radical terminates in a carboxylic acid group.

The term "haloalkyl" means an alkyl that is optionally substituted with one or more (e.g., 1, 2, 3, 4, or 5) halo. Non limiting examples of "haloalkyl" include iodomethyl, bromomethyl, chloromethyl, fluoromethyl, trifluoromethyl, 2-chloroethyl, 2-fluoroethyl, 2,2,2-trifluoroethyl 2,2-difluoroethyl and pentafluoroethyl.

The term "alkoxy" refers to an alkyl groups attached to the remainder of the molecule via an oxygen atom ("oxy"). Non limiting examples of "alkoxy" include methoxy, ethoxy, propoxy, isopropoxy, butoxy, iso-butoxy, sec-butoxy, pentoxy, 3-pentoxy, or hexyloxy;

The term "cycloalkyl" refers to a saturated all carbon ring having 3 to 8 carbon atoms (i.e., ($C_3$-$C_8$)carbocycle). The term also includes multiple condensed, saturated all carbon ring systems (e.g., ring systems comprising 2, 3 or 4 carbocyclic rings). Accordingly, carbocycle includes multicyclic carbocycles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocycles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2] octane, etc). Non-limiting examples of cycloalkyls include cyclopropyl, cyclobutyl, cyclopentyl, cyclohexyl, bicyclo [2.2.1]heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., cycloalkyl. Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. Dap, PyrAla, ThiAla, (pCl)Phe, (pNO$_2$)Phe, ε-Aminocaproic acid, Met[O$_2$], dehydPro, (3I)Tyr, norovaline (Nva), norleucine (Nle), para-I-phenylalanine ((pI)Phe), 2-napthylalanine (2-Nal), β-cyclohexylalanine (Cha), β-alanine (β-Ala), phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid (Tic), penicillamine, ornithine, citruline, α-methyl-alanine, para-benzoylphenylalanine, phenylglycine, propargylglycine, sarcosine, and tert-butylglycine) in D or L form. The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley:

New York, 1981, and references cited therein). An amino acid can be linked to the remainder of a compound of formula I through the carboxy terminus, the amino terminus, or through any other convenient point of attachment, such as, for example, through the sulfur of cysteine.

The term "side chain of an amino acid" refers to a portion of an amino acid, which is attached to the α-carbon of the amino acid. The structure of an amino acid can be illustrated by the following formula:

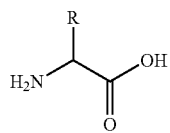

wherein R is the side chain of the amino acid. Non-limiting examples of "side chain of an amino acid" includes hydrogen, methyl, isopropyl, benzyl, 4-hydroxybenzyl, hydroxymethyl, 1-hydroxyethyl, and 4-aminobutyl.

The term "fatty acid" refers to various constituents found in lipids. Fatty adds have alkyl or alkenyl groups of various lengths and degrees of unsaturation terminated with carboxylic acid groups. The chain-length range of fatty acids is from 2 to 80 but commonly from 12 up to 24, and typically an even number. Common saturated fatty acids are lauric acid ($CH_3(CH_2)_{10}COOH$), palmitic acid ($CH_3(CH_2)_{14}COOH$) and stearic acid ($CH_3(CH_2)_{16}COOH$). Fatty acids may be oxygenated with a hydroxyl, epoxy, or furanoid group. Fatty acids may have double bonds (alkenyl) in the cis or trans configuration.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

The terms "treat" and "treatment" refer to both therapeutic treatment and prophylactic or preventative measures, wherein the object is to prevent or decrease an undesired physiological change or disorder, such as a metabolic disorder (e.g., obesity, anorexia, failure to thrive) or a disease associated with the metabolic disorder. Additional applications include cachexia and any disorder related to feeding behavior and the desire to eat or not eat. Treatment includes combination therapy where the compound of the present invention may be co-administered with an additional therapeutic agent, such as a metabolic drug, as part of a dosage regimen or course of therapy. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

As used herein a wavy line " ~~~ " that intersects a bond in a chemical structure indicates the point of attachment of the bond that the wavy bond intersects in the chemical structure to the remainder of a molecule.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2H$ or D). As a non-limiting example, a —$CH_3$ group may be substituted with —$CD_3$. Applications of isotopic-labeling or incorporation may include PET imaging of animal or humans.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound of formula I herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 99% the absolute stereoisomer depicted.

In one embodiment, the compound of formula I is a compound of formula Ia:

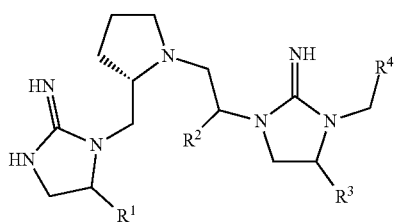

Ia or a salt thereof.

In one embodiment, at least one of $R^1$, $R^2$, $R^3$, and $R^4$ is not H.

In one embodiment, at least two of $R^1$, $R^2$, $R^3$, and $R^4$ are not H.

In one embodiment, none of $R^1$, $R^2$, $R^3$, and $R^4$ is H.

In one embodiment, $R^1$ is a side chain of an amino acid. In one embodiment, the amino acid is selected from the group consisting of: D-Leu, D-Val, D-Ile, D-Cha, D-Nle, D-Nva, D-Thr, D-Ala(2-naphthyl), D-Phe, D-Ala, D-Tyr, Gly, Ala, D-Ser, Val, Phg, Tyr, Nva, Thr, Ala(2-naphthyl), Leu, Nle, Ile, Phe, and Ser. In one embodiment, the amino acid is a D-amino acid. In one embodiment, the amino acid is a natural amino acid. In one embodiment, the amino acid is D-Leu or D-Val. In one embodiment, the amino acid is not proline.

In one embodiment, $R^1$ is $C_{1-8}$ alkyl.

In one embodiment, $R^1$ is $C_{1-30}$ alkyl, optionally substituted with one or more COOH.

In one embodiment, $R^1$ is an alkyl with up to 30 carbon atoms and terminating in a carboxylic acid.

In one embodiment, $R^1$ is a fatty acid.

In one embodiment, $R^1$ is

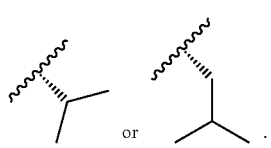

In one embodiment, $R^2$ is a side chain of an amino acid. In one embodiment, the amino acid is selected from the group consisting of: D-Cha, Cha, D-Nle, D-Phe, D-Ser, D-Leu, D-Nva, Ala(2-naphtyl), Ser, Phg, D-Ala(2-naphtyl), Val, Ile, D-Thr, Nle, Tyr, D-Tyr, D-Ile, D-Ala, Ala, D-Val, Phe, Nva, Gly, and Thr. In one embodiment, the amino acid is a D-amino acid. In one embodiment, the amino acid is a natural amino acid. In one embodiment, the amino acid is a non-natural amino acid. In one embodiment, the amino acid is D-Cha or D-Phe. In one embodiment, the amino acid is not proline.

In one embodiment, wherein:

$R^2$ is $-L^2-A^2$;

$L^2$ is $C_{1-4}$ alkylene; and $A^2$ is cycloalkyl or aryl.

In one embodiment, wherein $R^2$ is:

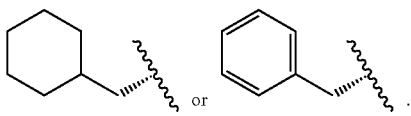

In one embodiment, wherein $R^3$ is a side chain of an amino acid. In one embodiment, wherein the amino acid is selected from the group consisting of: D-Thr, D-Nva, D-Val, D-Ile, Gly, D-Ala, D-Leu, D-Nle, D-Ser, Ala, Nle, Thr, Val, D-Tyr, Nva, Ile, Ser, D-Phe, Ala(2-naphthyl), Leu, Tyr, Phe, D-Cha, Phg, D-Ala(2-naphthyl), and Cha. In one embodiment, wherein the amino acid is a D-amino acid. In one embodiment, wherein the amino acid is a natural amino acid. In one embodiment, wherein the amino acid is a non-natural amino acid. In one embodiment, wherein amino acid is D-Thr, D-Nva, or D-Val. In one embodiment, the amino acid is not proline.

In one embodiment, wherein $R^3$ is $C_{1-8}$ alkyl which is optionally substituted with hydroxy.

In one embodiment, $R^3$ is $C_{1-30}$ alkyl, optionally substituted with one or more COOH.

In one embodiment, wherein $R^3$ is:

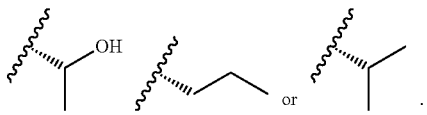

In one embodiment, wherein:

$R^4$ is $C_{1-30}$ alkyl optionally substituted with one or more COOH, or $-L^4-A^4$;

$L^4$ is absent or $C_{1-4}$ alkylene; and $A^4$ is cycloalkyl or phenyl; wherein the cycloalkyl or phenyl is optionally substituted with one or more groups selected from the group consisting of halo, hydroxy, $C_{1-6}$ alkyl, $C_{1-6}$ alkoxy, $C_{1-6}$ haloalkyl, and phenyl;

In one embodiment, wherein $R^4$ is $C_{1-8}$ alkyl.

In one embodiment, wherein $R^4$ is —CH$_2$CH$_2$CH(CH$_3$)$_2$.

In one embodiment, wherein:

$R^4$ is $-L^4-A^4$;

$L^4$ is absent; and $A^4$ is cycloalkyl which is optionally substituted with one or more $C_{1-6}$ alkyl groups.

In one embodiment, wherein R⁴ is:
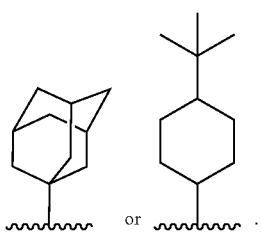
or
In one embodiment, the compound of formula I is selected from the group consisting of:
TPI 2509-4
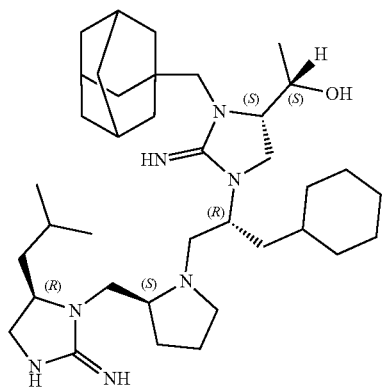
TPI 2509-5
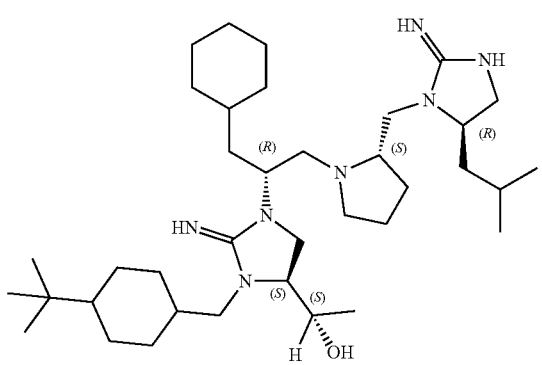
TPI 2509-6
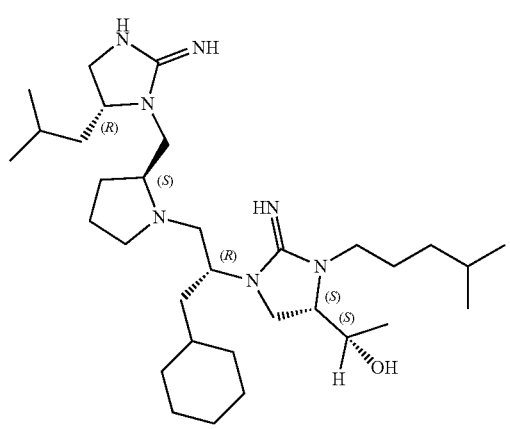
TPI 2509-7
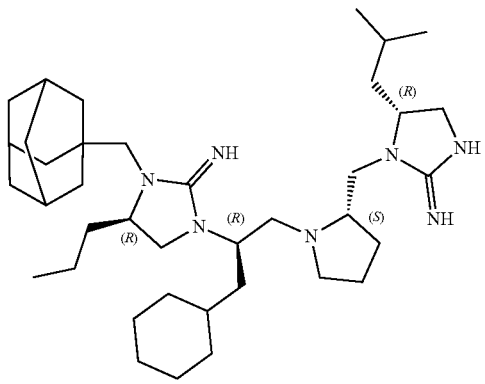
TPI 2509-8
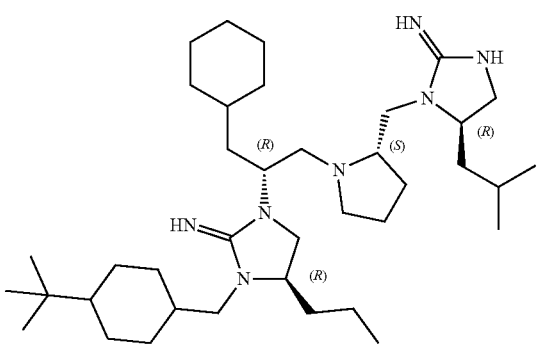
TPI 2509-9
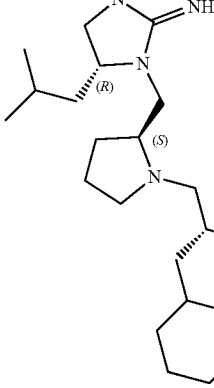
TPI 2509-10
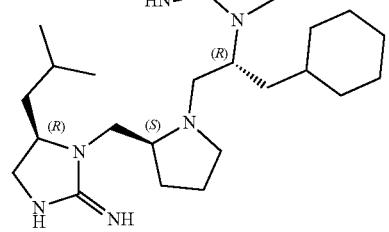

TPI 2509-11
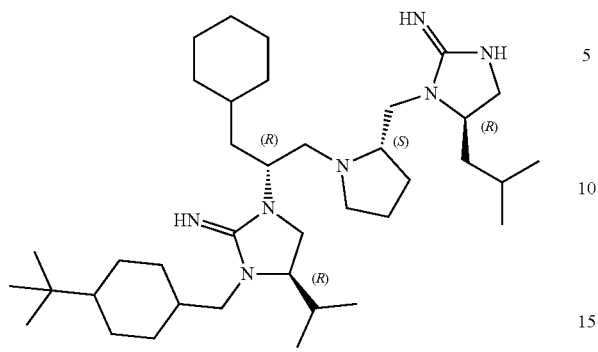
TPI 2509-12
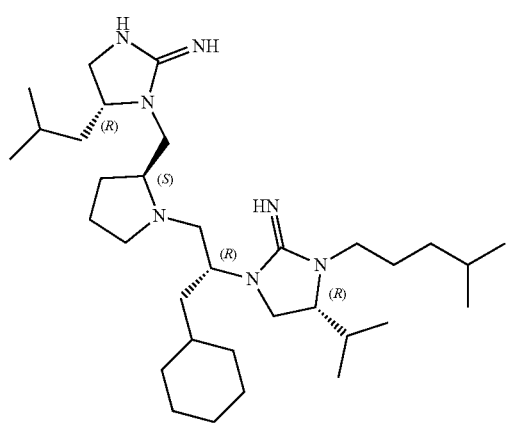
TPI 2509-13
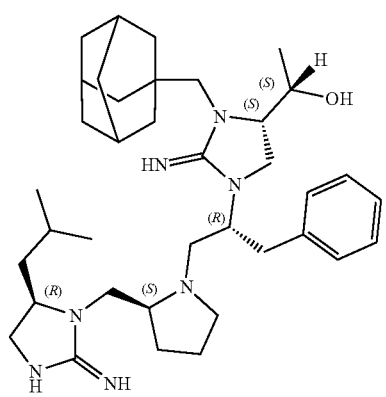
TPI 2509-14
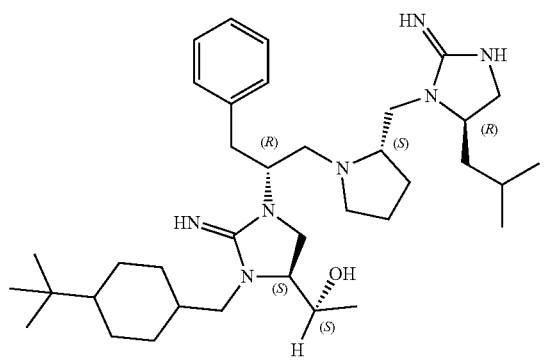
TPI 2509-15
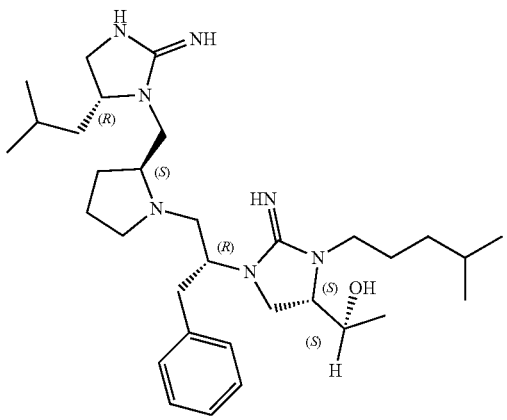
TPI 2509-16
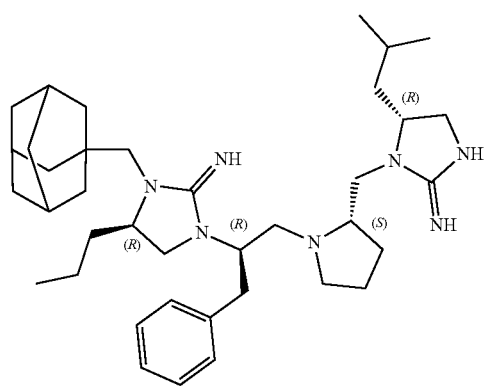
TPI 2509-17
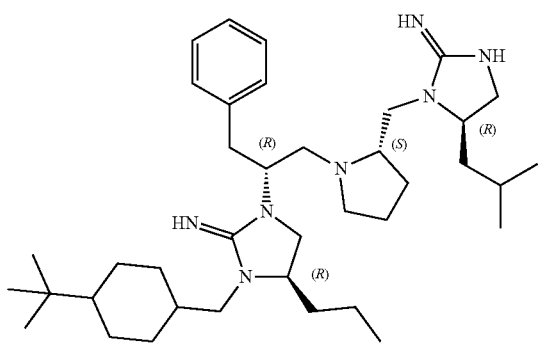
TPI 2509-18
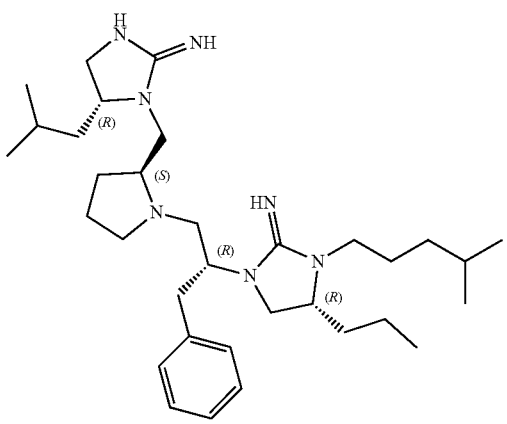

TPI 2509-19
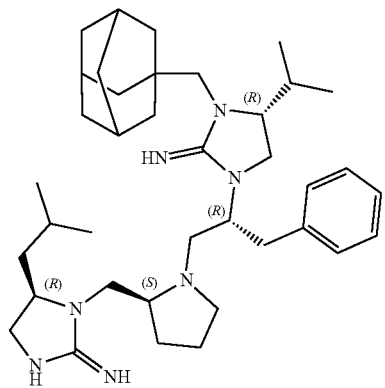
TPI 2509-20
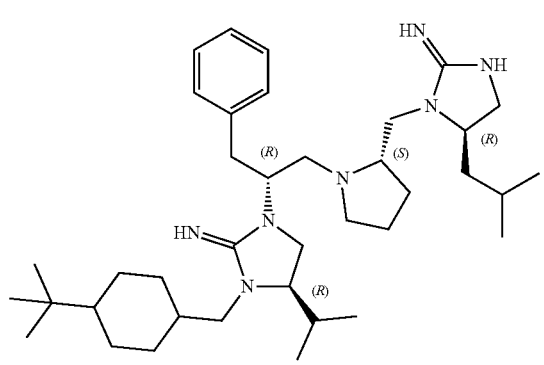
TPI 2509-21
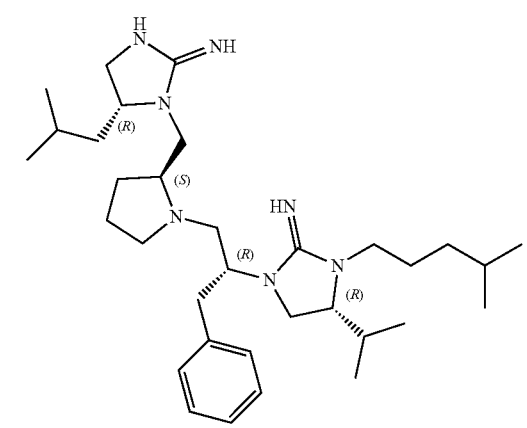
TPI 2509-22
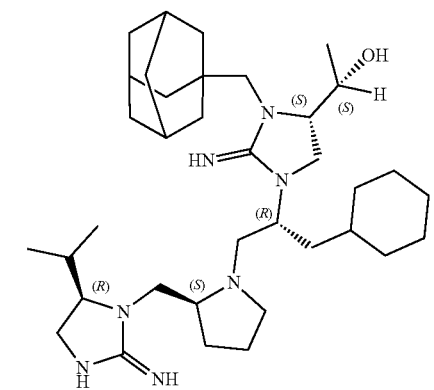
TPI 2509-23
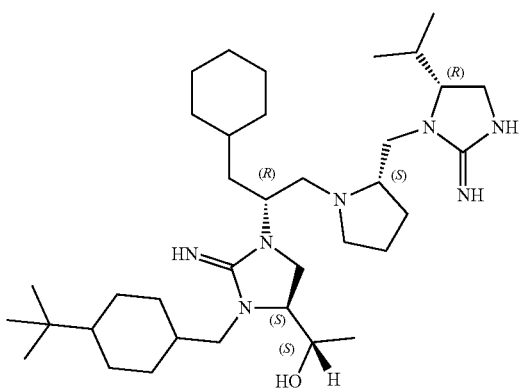
TPI 2509-24
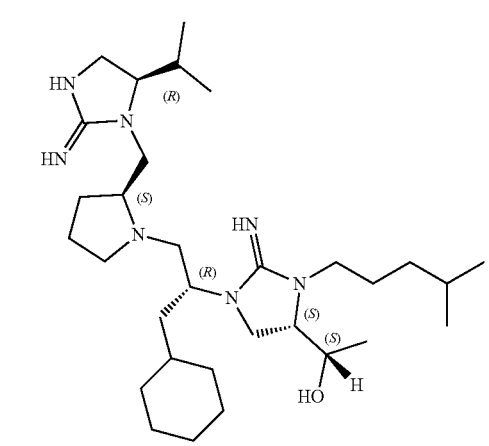
TPI 2509-25
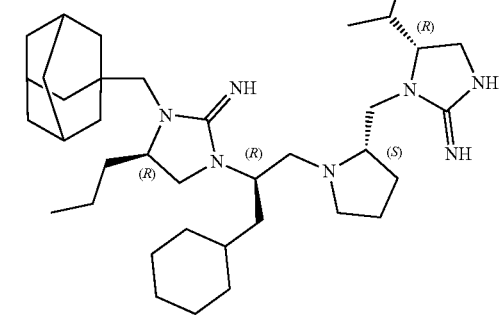
TPI 2509-26
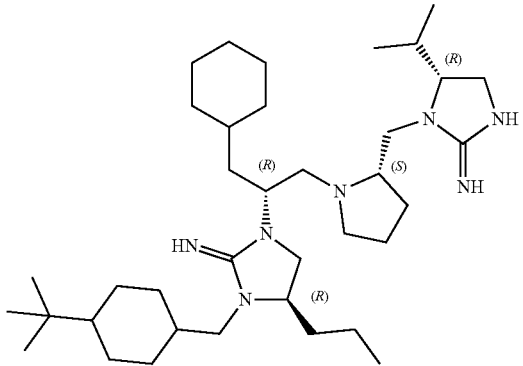

-continued
TPI 2509-27
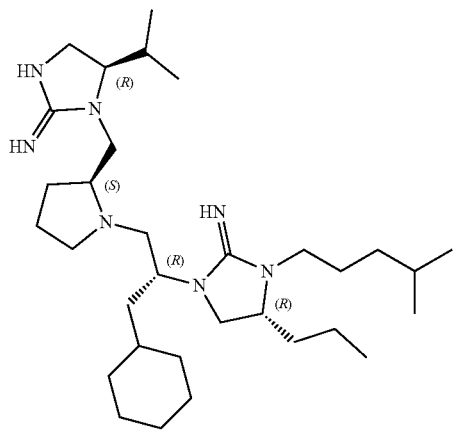
TPI 2509-28
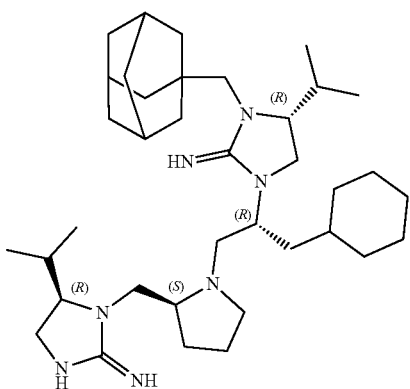
TPI 2509-29
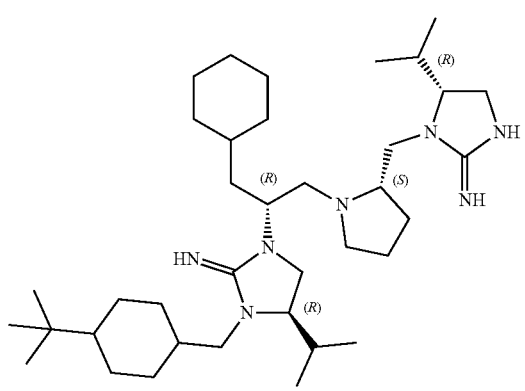
-continued
TPI 2509-30
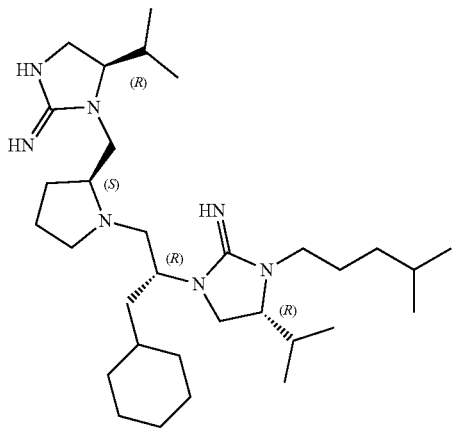
TPI 2509-31
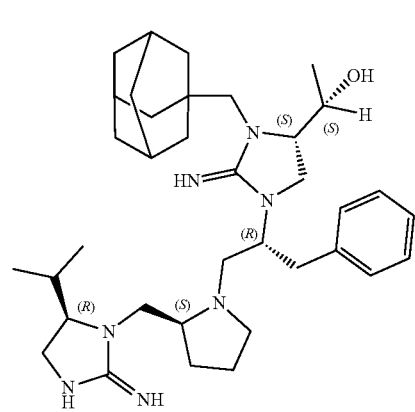
TPI 2509-32
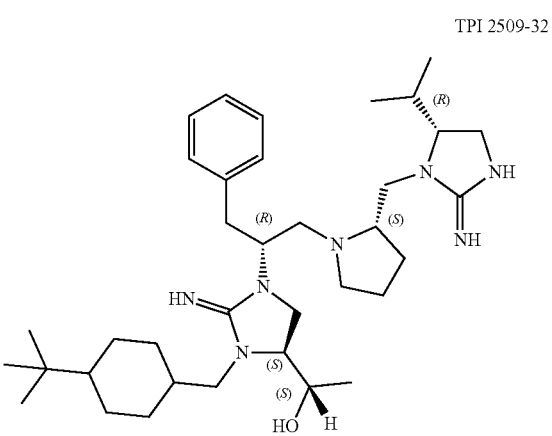

TPI 2509-33
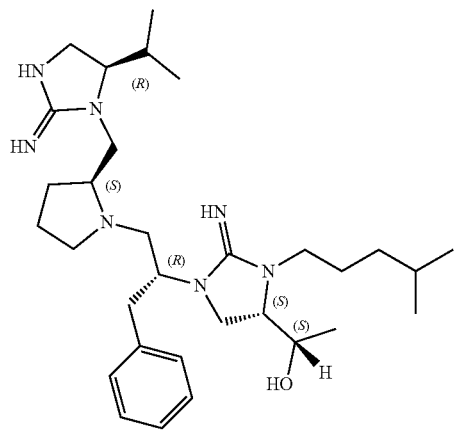
TPI 2509-36
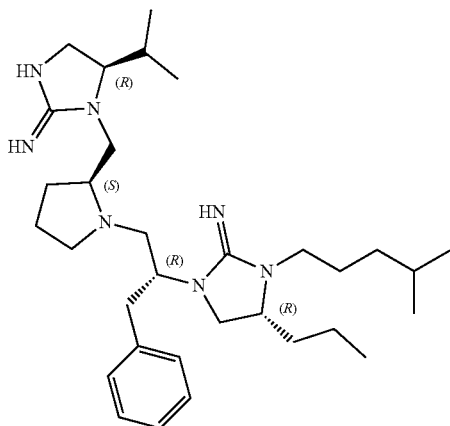
TPI 2509-34
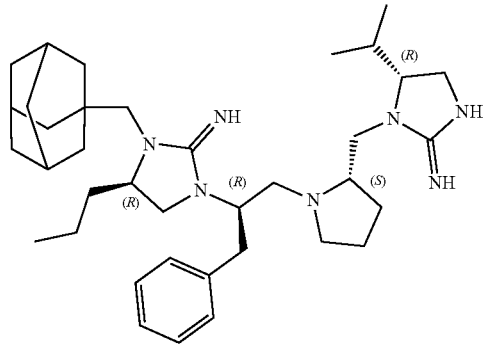
TPI 2509-37
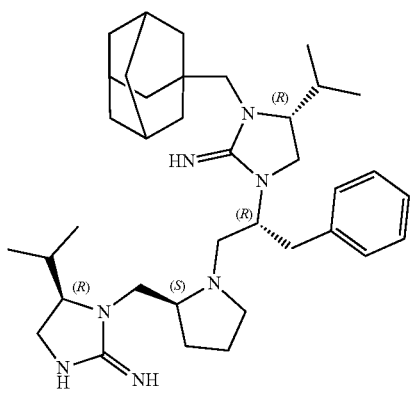
TPI 2509-35
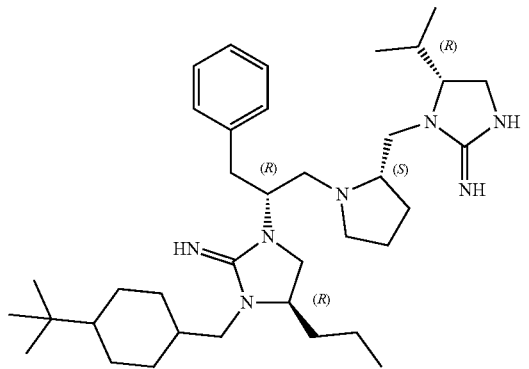
TPI 2509-38
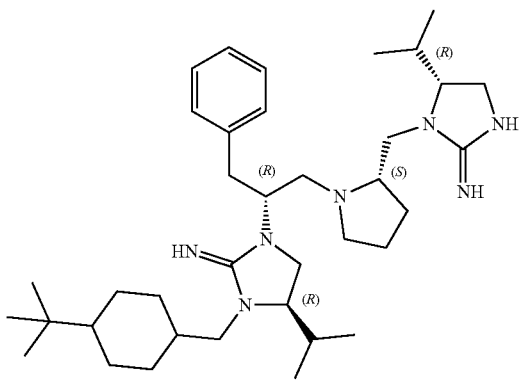

TPI 2509-39

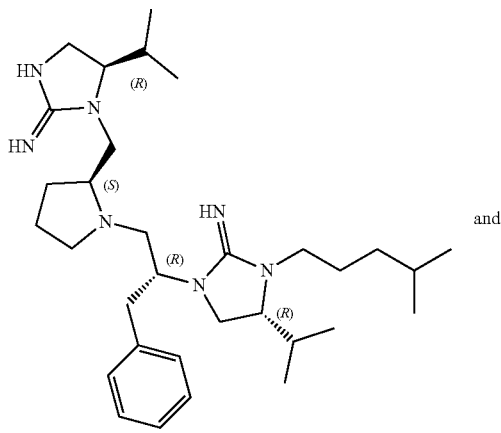

and

TPI 2509-40

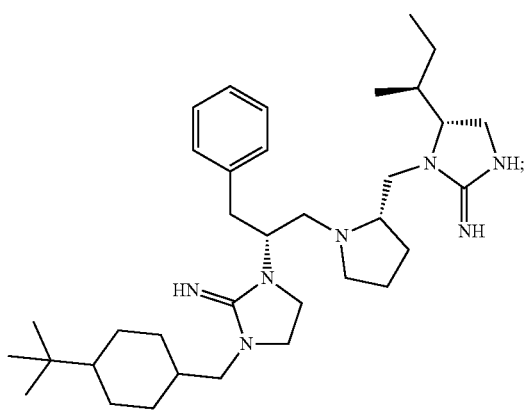

and salts thereof.
In one embodiment, the compound of formula I is:

TPI 2509-14

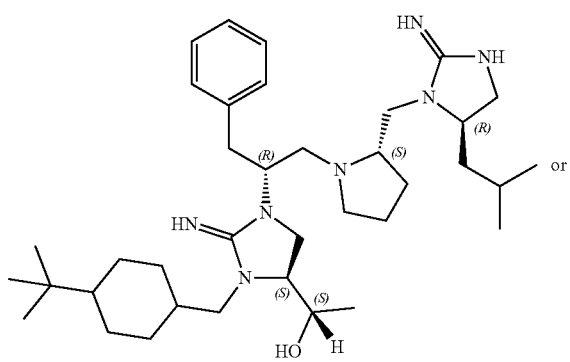

or

TPI 2509-32

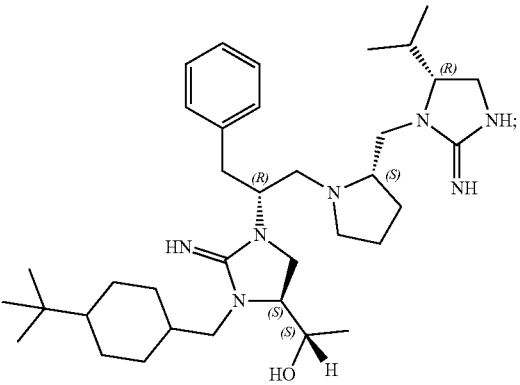

or a salt thereof.

In one embodiment, the compound of invention is an agonist for a melanocortin receptor (e.g. MC1R, MC2R, MC3R, MC4R, and MC5R). As described herein, agonist activity is the ability of a compound of the invention to stimulate a melanocortin receptor. The activity may be measured using an assay described in the Examples and may be reported as an $EC_{50}$ value (i.e., the concentration of compound needed to achieve 50% stimulation). In contrast, antagonist activity is the ability of a compound of the invention to block a melanocortin receptor. Antagonist activity of a given compound may be reported as a $pA_2$ value and measured using an assay described herein. $pA_2$ is defined as the negative $Log_{10}$ of the molar concentration of the antagonist needed to reduce the activity of an agonist such that double the concentration of the agonist is needed to recover the level of activity observed when the agonist is assayed alone (Schild, British Journal of Pharmacology, 1947, volume 2, issue 3, pages 189-206). The antagonist activity may also be reported as a $K_i$ value, which is the inverse Log of $pA_2$. For example, a compound of the invention may be at least 5, at least 10, at least 50, at least 100, at least 500, or at least 1,000 fold selective for a given melanocortin receptor (e.g., MC1R, MC2R, MC3R, MC4R and/or MC5R) over another melanocortin receptor(s) in a selected assay (e.g., an assay described in the Examples herein). In one embodiment the compound may be at least 5, at least 10, at least 50, at least 100, at least 500, or at least 1,000 fold selective (e.g., a selective agonist or antagonist) for MC3R over another melanocortin receptor(s) (e.g., over MC4R). In one embodiment the inhibitor may be at least 5, at least 10, at least 50, at least 100, at least 500, or at least 1,000 fold selective (e.g., selective antagonist) for MC4R over another melanocortin receptor(s).

In one embodiment, a compound of formula (I) is a melanocortin-3 receptor (MC3R) agonist (i.e., activates MC3R). In one embodiment, a compound of formula (I) is a selective melanocortin-3 receptor (MC3R) agonist (i.e., selectively activates MC3R, e.g., over MC4R) (e.g., at least 5, at least 10, at least 50, at least 100, at least 500, or at least 1,000 fold selective). In one embodiment, a compound of formula (I) is melanocortin-4 receptor (MC4R) antagonist (i.e., blocks activation of MC4R). In one embodiment, a compound of formula (I) is a selective melanocortin-4 receptor (MC4R) antagonist (i.e., selectively blocks activation of MC4R) (e.g., at least 5, at least 10, at least 50, at least 100, at least 500, or at least 1,000 fold selective). In one embodiment, a compound of formula (I) is a MC3R agonist and a MC4R antagonist. In one embodiment, a compound of formula (I) is a selective MC3R agonist and a selective MC4R antagonist (e.g., at least 5, at least 10, at least 50, at least 100, at least 500, or at least 1,000 fold selective for agonist and/or antagonist activity).

In one embodiment, a compound of formula (I) has an $EC_{50}$ at MCR3 of less than 10 µM, e.g., less than 1 µM, e.g., less than 100 nM, e.g., less than 50 nM, e.g., less than 25 nM, e.g., less than 10 nM, e.g., less than 1 nM, e.g., or greater than 0.01 nM.

In one embodiment, a compound of formula (I) has an $EC_{50}$ at MC4R of greater than 1 µM, e.g., greater than 10 µM, e.g., greater than 50 µM, e.g., greater than 100 µM. In one embodiment, the compound of invention is not an agonist for MC4R.

One embodiment of the invention provides a dietary supplement comprising a compound of formula I, or a salt thereof.

Another embodiment of the invention provides a prodrug of a compound of formula I or a salt thereof. As used herein the term "prodrug" refers to a biologically inactive compound that can be metabolized in the body to produce a biologically active form of the compound.

In one embodiment, the disease associated with obesity is diabetes, cardiovascular disease or hypertension.

One embodiment of the invention provides a method of modulating (e.g., increasing or decreasing) the activity of a melanocortin receptor in vitro or in vivo comprising contacting the receptor with an effective amount of a compound of formula I, or a pharmaceutically acceptable salt thereof. In one embodiment, the melanocortin receptor is MC3R. In one embodiment, the melanocortin receptor is MC4R. One embodiment of the invention provides a method of increasing the activity of melanocortin-3 receptor in vitro or in vivo comprising contacting the receptor with an effective amount of a compound of formula I, or a pharmaceutically acceptable salt thereof. One embodiment of the invention provides a method of decreasing the activity of melanocortin-4 receptor in vitro or in vivo comprising contacting the receptor with an effective amount of a compound of formula I, or a pharmaceutically acceptable salt thereof.

One embodiment of the invention provides a compound of formula I, or a pharmaceutically acceptable salt thereof for use in modulating (e.g., increasing or decreasing) the activity of a melanocortin receptor in vitro or in vivo.

One embodiment of the invention provides the use of a compound of formula I, or a pharmaceutically acceptable salt thereof for the manufacture of a medicament for modulating (e.g., increasing or decreasing) the activity of a melanocortin receptor in vitro or in vivo.

One embodiment of the invention provides a method of selectively activating melanocortin-3 receptor (MC3R) over melanocortin-4 receptor (MC4R) in vitro or in vivo comprising contacting the receptors with an effective amount of a compound of formula I or a pharmaceutically acceptable salt thereof.

One embodiment of the invention provides a compound of formula I, or a pharmaceutically acceptable salt thereof for use in selectively activating melanocortin-3 receptor (MC3R) over melanocortin-4 receptor (MC4R) in vitro or in vivo.

One embodiment of the invention provides the use of a compound of formula I, or a pharmaceutically acceptable salt thereof for the manufacture of a medicament for selectively activating melanocortin-3 receptor (MC3R) over melanocortin-4 receptor (MC4R) in vitro or in vivo.

Another embodiment of the invention provides a method of modulating (e.g., increasing or decreasing) metabolic activity and feeding behavior in an animal in need thereof, comprising administering an effective amount of a compound of formula I, or a pharmaceutically acceptable salt thereof, to the animal.

Another embodiment of the invention provides a compound of formula I, or a pharmaceutically acceptable salt thereof for use in modulating (e.g., increasing or decreasing) metabolic activity and feeding behavior.

Another embodiment of the invention provides the use of a compound of formula I, or a pharmaceutically acceptable salt thereof for the manufacture of a medicament for modulating (e.g., increasing or decreasing) metabolic activity and feeding behavior.

Another embodiment of the invention provides a method of modulating (e.g., increasing or decreasing) appetite in humans or any animal in need thereof, comprising administering an effective amount of a compound of formula I, or a pharmaceutically acceptable salt thereof, to the animal.

Another embodiment of the invention provides a compound of formula I, or a pharmaceutically acceptable salt thereof for use in modulating (e.g., increasing or decreasing) appetite.

Another embodiment of the invention provides the use of a compound of formula I, or a pharmaceutically acceptable salt thereof for the manufacture of a medicament for modulating (e.g., increasing or decreasing) appetite.

In cases where compounds are sufficiently basic or acidic, a salt of a compound of formula (I) can be useful as an intermediate for isolating or purifying a compound of formula (I). Additionally, administration of a compound of formula (I) as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of formula (I) (including salts and prodrugs thereof) can be formulated as pharmaceutical compositions and administered to a mammalian host, such as a human patient in a variety of forms adapted to the chosen route of administration, i.e., orally or parenterally, by intravenous, intramuscular, intrathecal, topical, nasal, inhalation, suppository, sub dermal osmotic pump, or subcutaneous routes.

Thus, the present compounds may be systemically administered, e.g., orally, in combination with a pharmaceutically acceptable vehicle such as an inert diluent or an edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compound of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents. For example, compounds of formula (I), or salts thereof, may be administered with other agents that are useful for modulating appetite (i.e., increasing or decreasing), modulating metabolic activity, treating obesity or diseases associated with obesity (e.g., diabetes, cardiovascular disease or hypertension), inducing weight loss, increasing or decreasing weight gain. Accordingly, in one embodiment the invention also provides a composition comprising a compound of formula (I), or a pharmaceutically acceptable salt thereof, at least one other therapeutic agent, and a pharmaceutically acceptable diluent or carrier. The invention also provides a kit comprising compound of formula (I), or a pharmaceutically acceptable salt thereof, at least one other therapeutic agent, packaging material, and instructions for administering the compound of formula (I) or the pharmaceutically acceptable salt thereof and the other therapeutic agent or agents to an animal to modulate appetite, modulate metabolic activity, treat obesity or diseases associated with obesity (e.g., diabetes, cardiovascular disease or hypertension), induce weight loss, increase weight gain, or decrease weight gain.

Compounds of invention can be prepared using known methods or using procedures analogous to those described in the examples herein (Houghten, R. A., et al, *J. Med. Chem.* (1999) 42 (19):3743-3778; Pinilla, C., et al, *Nat. Med.* (2003) 9 (1):118-122; Houghten, R. A., et al, *J. Comb. Chem.* (2008) 10 (1):3-19). For example, compounds of invention can be prepared as illustrated in the following scheme.

Cyanogen Bromide (3 eq per site), 0.1 m in anhydrous dcm (3 hr); 2× anhydrous DCM (1 min); h. HF, 0° C., 1.5 hr

EXAMPLES

The invention will now be illustrated by the following non-limiting Examples.

Example 1. Design of Melanocortin Receptor Modulators

A unique high throughput screening approached is utilized. This approach is known in the field as mixture based positional scanning, extensively used to discover new compounds for a variety of targets. A compound discovered by this screening approach is currently in clinical trials (Dooley, C. T., et al, *Jour. of Biol. Chem.*, (1998). 273:18848-56). The modified tetrapeptide, CR845, has results for phase 2 clinical trials for pain management and is currently recruiting for phase 3 trials (clinicaltrials.gov identifiers NCT02858726, NCT02524197, NCT01789476, NCT00877799, NCT02229929, NCT02542384, NCT02944448, and NCT01361568).

The high throughput mixture based screening approach is conducted in three discrete stages. The initial stage "Scaffold Ranking" is the identification of the best chemical scaffold for one's target out a library of approximately 100 different Scheme 1. Synthesis of representative compounds

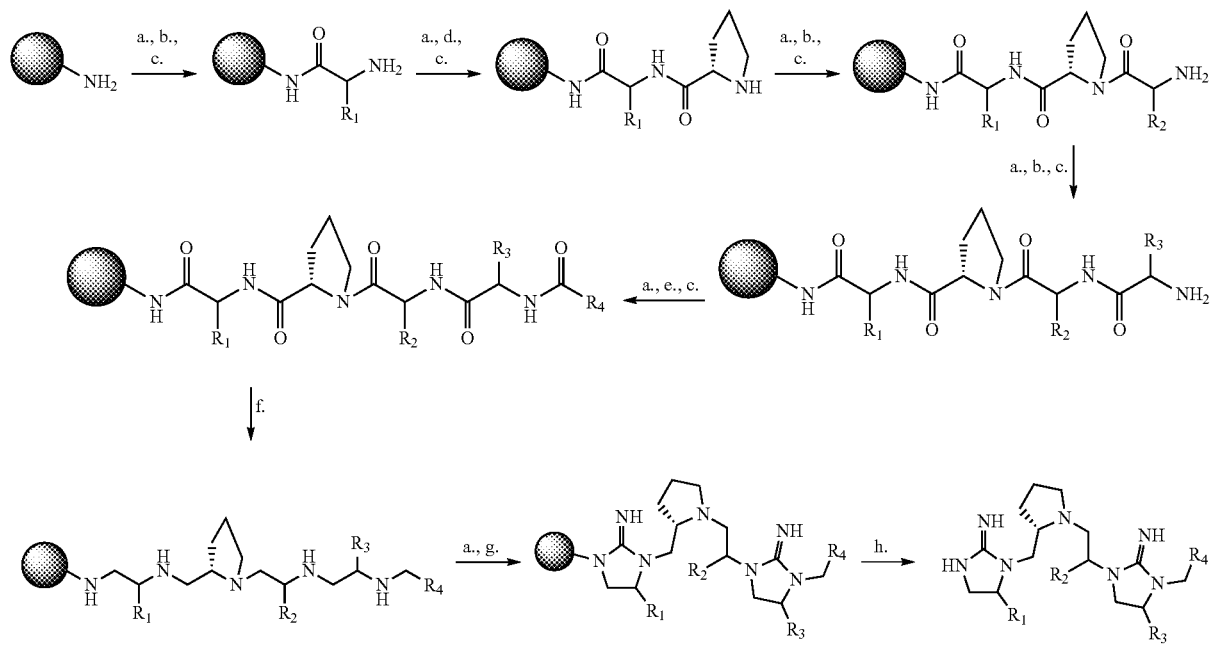

The synthesis starts with MBHA resin. a. 3×DCM (1 min); 3× 5% DIEA/DCM (2 min); 3×DCM (1 min); b. Boc-AA-OH (6 eq), DIC (6 eq), HOBt (6 eq), 0.1 M in DMF (1 hr); c. 3×DMF (1 min); 3×DCM (1 min); 1× 55% TFA/DCM (30 min); 2×DCM (1 min); 2×IPA (1 min); d. Boc-L-Proline-OH (6 eq), DIC (6 eq), HOBt (6 eq), 0.1 M in DMF (1 hr); e. R—COOH (10 eq), DIC (10 eq), HOBt (10 eq), 0.1 M in DMF (1 hr); f. Borane/THF (40 eq), anhydrous conditions, 65° C. (72 hr); piperidine, 65° C. (24 hr); g. under anhydrous conditions, 2× anhydrous DCM (1 min); 1× scaffolds. After the scaffold is selected, the second stage "positional scanning" determines different substituents which optimizes the scaffold to be more potent and selective. In this stage millions of different compounds are tested. After possible substituents are determined a smaller library, typically 10 to 100 individual compounds, are synthesized and tested and the lead compounds are then identified. This process has recently been utilized in the identification of new antibacterial agents and could serve in illustrating how this is done in practice (Doering, S., et al (2021) *J. Med. Chem.*, 64(9):5577-5592; Fleeman, R., et al (2015) *J. Med. Chem.*, 58:3340-55).

Scaffold Ranking

Approximately 100 different scaffolds were tested for activity at both the melanocortin-3 and melanocortin-4 receptors with a whole cell in vitro assay (Haskell-Luevano, C. et al, *Peptides* (1996) 17(6):995-1002). This cell assay utilizes HEK293 cells which are transfected with the various melanocortin receptor subtypes and cAMP, a signal important to melanocortin receptor activation, is indirectly measured using a beta-galactosidase reporter gene system (Chen, W., et al, *Analytical Biochemistry*, 1995, vol. 226, pp. 349-354). Selectivity of the melanocortin-3 receptor over the melanocortin-4 receptor was measured and calculated. Scaffold TPI1955 was relatively selective for the melanocortin-3 receptor over the melanocortin-4 receptor and was chosen to move onto the next stage. In addition, scaffold TPI1955 did not cause any observed cell toxicity at the highest concentrations it was tested which was unlike the other scaffolds which scored high using this analysis.

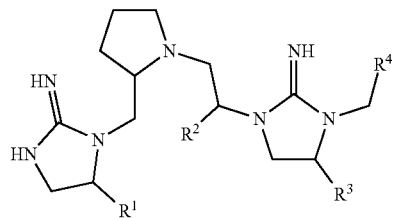

TP1955 Scaffold

Positional Scanning

After the bicyclic guanidine TPI1955 scaffold was selected, a variety of substituents were tested at each of the four positions. A total of 26 different substituents were tested at positions $R^1$, $R^2$, and $R^3$, while 42 were tested at position $R^4$. Table 1 lists all the building blocks as substituents $R^1$-$R^4$ included in the TPI1955 positional scanning library, and as described in formula I.

TABLE 1

Substituents $R^1$-$R^4$ included in the TPI1955 positional scanning library

| No. | R1 | R2 | R3 | R4 |
|---|---|---|---|---|
| 1 | Boc-D-Leu-OH | Boc-D-Cha-OH | Boc-D-Thr(Bzl)-OH | 1-adamantanecarboxylic acid |
| 2 | Boc-D-Val-OH | Boc-Cha-OH | Boc-D-Nva-OH | 4-tert-butyl-cyclohexanecarboxylic acid |
| 3 | Boc-D-Ile-OH | Boc-D-Nl3-OH | Boc-D-Val-OH | 4-methylvaleric acid |
| 4 | Boc-D-Cha-OH | Boc-D-Phe-OH | Boc-D-Ile-OH | 2-norbornaneacetic acid |
| 5 | Boc-D-Nle-OH | Boc-D-Ser(Bzl)-OH | Boc-Gly-OH | cyclohexanepropionic acid |
| 6 | Boc-D-Nva-OH | Boc-D-Leu-OH | Boc-D-Ala-OH | 2-phenylbutyric acid |
| 7 | Boc-D-Thr(Bzl)-OH | Boc-Leu-OH | Boc-D-Leu-OH | 3-cyclopentylpropionic acid |
| 8 | Boc-D-Ala(2-naphthyl)-OH | Boc-D-Nva-OH | Boc-D-Nle-OH | 1-adamantaneacetic acid |
| 9 | Boc-D-Phe-OH | Boc-Ala(2-naphthyl)-OH | Boc-D-Ser(Bzl)-OH | cyclobutanecarboxylic acid |
| 10 | Boc-D-Ala-OH | Boc-Ser(Bzl)-OH | Boc-Ala-OH | phenylacetic acid |
| 11 | Boc-D-Tyr(2-Br-Z)-OH | Boc-Phg-OH | Boc-Nle-OH | 4-methyl-1-cyclohexanecarboxylic acid |
| 12 | Boc-Gly-OH | Boc-D-Ala(2-naphthyl)-OH | Boc-Thr(Bzl)-OH | 4-biphenylacetic acid |
| 13 | Boc-Ala-OH | Boc-Val-OH | Boc-Val-OH | heptanoic acid |
| 14 | Boc-D-Ser(Bzl)-OH | Boc-Ile-OH | Boc-D-Tyr(2-Br-Z)-OH | 4-ethoxyphenylacetic acid |
| 15 | Boc-Val-OH | Boc-D-Thr(Bzl)-OH | BocNva-OH- | 3,4,5-trimethoxybenzoic acid |
| 16 | Boc-Phg-OH | Boc-Nle-OH | Boc-Ile-OH | 2-methylcyclopropanecarboxylic acid |
| 17 | Boc-Tyr(2-Br-Z)-OH | Boc-Tyr(2-Br-Z)-OH | Boc-Ser(Bzl)-OH | 2-methylbutyric acid |
| 18 | Boc-Nva-OH- | Boc-D-Tyr(2-Br-Z)-OH | Boc-D-Phe-OH | cyclohexanebutyric acid |
| 19 | Boc-Thr(Bzl)-OH | Boc-D-Il3-OH | Boc-Ala(2-naphthyl)-OH | (α,α,α-trifluoro-m-tolyl)acetic acid |
| 20 | Boc-Ala(2-naphthyl)-OH | Boc-D-Ala-OH | Boc-Leu-OH | 3-methylvaleric acid |
| 21 | Boc-Leu-OH | Boc-Ala-OH | Boc-Tyr(2-Br-Z)-OH | 4-fluorophenylacetic acid |
| 22 | Boc-Nle-OH | Boc-D-Val-OH | BocPhe-OH- | cycloheptanecarboxylic acid |
| 23 | Boc-Ile-OH | Boc-Phe-OH | Boc-D-Cha-OH | cyclohexanecarboxylic acid |
| 24 | Boc-Phe-OH | Boc-Nva-OH | Boc-Phg-OH | cyclohexylacetic acid |
| 25 | Boc-Ser(Bzl)-OH | Boc-Gly-OH | Boc-D-Ala(2-naphthyl)-OH | 4-isobutyl-α-methylphenylacetic acid |
| 26 | Boc-Cha-OH | Boc-Thr(Bzl)-OH | Boc-Cha-OH | 1-phenyl-1-cyclopropanecarboxylic acid |
| 27 | | | | isobutyric acid |
| 28 | | | | isovaleric acid |
| 29 | | | | 3-(3,4-dimethoxyphenyl)-propionic acid |
| 30 | | | | 3-methoxyphenylacetic acid |
| 31 | | | | cyclopentanecarboxylic acid |
| 32 | | | | butyric acid |
| 33 | | | | 3,4-dichlorophenylacetic acid |
| 34 | | | | m-tolylacetic acid |

TABLE 1-continued

Substituents $R^1$-$R^4$ included in the TPI1955 positional scanning library

| No. | R1 | R2 | R3 | R4 |
|---|---|---|---|---|
| 35 | | | | p-tolylacetic acid |
| 36 | | | | 4-methoxyphenylacetic acid |
| 37 | | | | 3,4-bis(trifluoromethyl)-phenylacetic acid |
| 38 | | | | 4-bromophenylacetic acid |
| 39 | | | | 3-fluorophenylacetic acid |
| 40 | | | | 3-bromophenylacetic acid |
| 41 | | | | 3-phenylbutyric acid |
| 42 | | | | p-toluic acid |

The 120 mixtures of Table 1 representing more than 730,000 compounds were tested for activity at the melanocortin-3 receptor. The common feature in each of the mixtures was one of the substituents at one of the positions was the same while everything else was varied (Houghten, R. et al (2000) *Drug Discovery Today*, 5:276-285). This allowed for the determination of the most important substituents at each position because active mixtures indicated the importance of a particular substituent at a particular position. The most active mixtures were identified using the same type of whole cell in vitro assay as used in the scaffold ranking section above (FIG. 3). The substituents identified to be active varied depending on the position on the chemical scaffold. The number of substituents selected for each of the positions was two at $R^1$, two at $R^2$, three at $R^3$, and three at $R^4$.

Individual Compounds

A set of 36 individual compounds (not mixtures) were synthesized and evaluated for biological activity. The number of compounds was based on all of the possible combinations for substituents at the four different positions on the TPI1955 scaffold (2×2×3×3=36). That is to say, if one were to list all of the possible permutations for compounds based on the substituents of the active mixtures from the positional scanning where there were 2 possible substituents at position $R^1$, 2 at $R^2$, 3 at $R^3$, and 3 at $R^4$, the total number of possible compounds using those chemical building blocks would result in a total of 36 individual compounds. All of the compounds have the compound identification TPI2509-XX.

Example 2. Synthesis and Characterization

Following the General Scheme, the solid-phase synthesis of the pyrrolidine bis-cyclic guandine library from resin-bound proline-containing acylated tetrapeptides was achieved. Starting from resin-bound amino acids (diversity $R^1$), Boc-proline was coupled using standard solid-phase coupling reagents, followed by Boc deprotection and subsequent coupling of two Boc-amino acids (diversities $R^2$ and $R^3$). The N-terminal Box was cleaved and the generated primary amine was N-acylated with different carboxylic acids (diversity $R^4$). The generated resin-bound N-acylated tetrapeptide was exhaustively reduced using borane-THF to yield a resin-bound pentamine containing two pairs of secondary amines separated by the pyrrolidine ring. The resulting pairs of secondary amines were treated with cyanogen bromide to generate the corresponding resin-bound pyrrolidine bis-cyclic guanidines. Twenty-six different amino acids were selected for $R^1$, $R^2$, and $R^3$, and 42 carboxylic acids for $R^4$ to prepare a library of pyrrolidine bis-cyclic guanidines containing 738,192 individual compounds in positional scanning format. (Hensler, M. et al, *Bioorg. & Med. Chem. Letters*, (2006) 16:5073-79). The synthesis of the set of 36 individual pyrrolidine bis-cyclic guanidines and 3 other compounds (TPI 2509) was carried out using the same synthetic strategy described for the library.

Compound Purification and Characterization

The individual compounds (TPI 2509) were purified using preparative HPLC with a dual pump Shimadzu LC-20AB system equipped with a Luna C18 preparative column (21.5×150 mm, 5 micron) at λ=214 nm, with a mobile phase of (A) H2O (+0.1% formic acid)/(B) acetonitrile (ACN) (+0.1% formic acid) at a flow rate of 15 mL/min; gradients varied by compound based on hydrophobicity. The purities of synthesized compounds were confirmed to be greater than 95% by liquid chromatography and mass spectrometry on a Shimadzu LCMS-2010 instrument with ESI Mass Spec and SPD-20A Liquid Chromatograph equipped with a Luna C18 column (50×4.6 mm, 5 micron) with a mobile phase of (A) H2O (+0.1% formic acid)/(B) ACN (+0.1% formic acid) (5-95% over 6 min with a 4 min rinse). 1H NMR spectra were recorded in DMSO-d6 or Chloroform-d on a Bruker Ascend 400 MHz spectrometer at 400.14 MHz.

TPI 2509-1 (2R,3S)-4-((S)-2-((((2R,3S)-1-amino-3-methylpentan-2-yl)amino)methyl)pyrrolidin-1-yl)-3-(((R)-2-(((4-(tert-butyl)cyclohexyl)methyl)amino)-3-cyclohexylpropyl)amino)butan-2-ol (1)

Using General Scheme for the synthesis of reduced pyrrolidino pentapeptides compound 2509-1 was synthesized using the following reagents: Boc-D-Isoleucine-OH ($R^1$), Boc-D-Threonine(Bzl)-OH ($R^2$), Boc-D-Cyclohexylalanine-OH ($R^3$), 4-tert-butyl-cyclohexancecarboxylic acid ($R^4$). The final crude product was purified using HPLC as described above, with a gradient of (B) 2, 0/2, 2/2, 6/20, 35/35. 1H NMR (400 MHz, DMSO-d6) d ppm 3.84 (br. s., 1H) 3.56 (br. s., 1H) 3.45 (br. s., 1H) 3.28 (d, J=11.86 Hz, 2H) 3.05 (br. s., 4H) 2.96 (br. s., 5H) 2.79 (br. s., 1H) 2.70 (br. s., 1H) 2.21 (br. s., 1H) 2.07 (br. s., 1H) 1.85-2.00 (m, 2H) 1.72-1.83 (m, 4H) 1.59-1.72 (m, 5H) 1.49 (br. s., 5H) 1.35 (br. s., 2H) 1.15-1.27 (m, 4H) 1.12 (br. s., 3H) 0.97-1.08 (m, 2H) 0.86-0.96 (m, 6H) 0.83 (br. s., 14H); m/z calcd C35H71N5O [M+H]+ 578.57, found (MS ESI) 578.55. Purity LCMS: 75% (TIC), N/A (214 nm, peak area); RT=3.88 min.

TPI 2509-3 4-((R)-3-(((R)-1-((S)-2-((((2R,3S)-1-amino-3-methylpentan-2-yl)amino)methyl)pyrrolidin-1-yl)-3-phenylpropan-2-yl)amino)-2-((3,5-bis(trifluoromethyl)phenethyl)amino)propyl)phenol (3)

Using General Scheme for the synthesis of reduced pyrrolidino pentapeptides compound 2509-3 was synthesized using the following reagents: Boc-D-Isoleucine-OH ($R^1$), Boc-D-Phenylalnine-OH ($R^2$), Boc-D-Tyrosine(2-Br—Z)—OH ($R^3$), 3,5-Bis(Trifluoromethyl)-Phenylacetic acid ($R^4$). The final crude product was purified using HPLC as described above, with a gradient of (B) 2, 0/2, 2/2, 6/20, 30/35, 35/40. 1H NMR (400 MHz, DMSO-d6) d ppm 9.39 (br. s., 1H) 8.18 (br. s., 1H) 7.96-8.08 (m, 3H) 7.17-7.43 (m, 4H) 7.12 (br. s., 3H) 6.76 (br. s., 2H) 3.60 (br. s., 3H) 3.38 (br. s., 5H) 3.23 (br. s., 2H) 3.15 (br. s., 1H) 3.05 (d, J=12.23 Hz, 2H) 2.77-2.97 (m, 5H) 2.52-2.74 (m, 4H) 2.19 (br. s., 1H) 1.92 (br. s., 2H) 1.77 (br. s., 1H) 1.64 (br. s., 1H) 1.32 (br. s., 1H) 1.18 (d, J=5.87 Hz, 1H) 0.85-0.93 (m, 3H) 0.81 (br. s., 3H); m/z calcd C39H53F6N5O [M+H]+ 722.42, found (MS ESI) 722.45. Purity LCMS: 64.74% (TIC), 98% (214 nm, peak area); RT=3.71 min.

TPI 2509-4 (R)-1-((S)-3-(adamantan-1-ylmethyl)-1-((R)-1-cyclohexyl-3-((S)-2-(((R)-2-imino-5-isobutyl-imidazolidin-1-yl)methyl)pyrrolidin-1-yl)propan-2-yl)-2-iminoimidazolidin-4-yl)ethanol (4)

Using General Scheme for the synthesis of bis-cyclic guanidines compound 2509-4 was synthesized using the following reagents: Boc-D-Leucine-OH·H2O ($R^1$), Boc-D-Cyclohexylalanine-OH ($R^2$), Boc-D-Threonine(Bzl)-OH ($R^3$), 1-Adamantancecarboxylic acid ($R^4$). The final crude product was purified using HPLC as described above, with a gradient of (B) 2, 0/2, 2/2, 6/20, 30/50. 1H NMR (400 MHz, CHLOROFORM-d) d ppm 10.11 (br. s., 1H) 8.83 (br. s., 1H) 8.60 (br. s., 2H) 4.33 (br. s., 2H) 4.08 (br. s., 2H) 3.98 (br. s., 1H) 3.79 (br. s., 1H) 3.56-3.73 (m, 2H) 3.49 (br. s., 3H) 3.29 (br. s., 2H) 3.14 (br. s., 1H) 2.91 (d, J=14.79 Hz, 1H) 2.82 (br. s., 1H) 2.65 (br. s., 1H) 2.21-2.40 (m, 2H) 1.99 (br. s., 4H) 1.84 (br. s., 1H) 1.71 (br. s., 6H) 1.53-1.68 (m, 11H) 1.41-1.53 (m, 3H) 1.35 (br. s., 1H) 1.19 (br. s., 6H) 0.98 (br. s., 4H) 0.93 (br. s., 4H); m/z calcd C37H65N7O [M+H]+ 624.54, found (MS ESI) 624.5. Purity LCMS: 96.45% (TIC), 98% (214 nm, peak area); RT=4.30 min.

TPI 2509-5 (R)-1-((S)-3-((4-(tert-butyl)cyclohexyl)methyl)-1-((R)-1-cyclohexyl-3-((S)-2-(((R)-2-imino-5-isobutylimidazolidin-1-yl)methyl)pyrrolidin-1-yl)propan-2-yl)-2-iminoimidazolidin-4-yl)ethanol (5)

Using General Scheme for the synthesis of bis-cyclic guanidines compound 2509-5 was synthesized using the following reagents: Boc-D-Leucine-OH·H2O ($R^1$), Boc-D-Cyclohexylalanine-OH ($R^2$), Boc-D-Threonine(Bzl)-OH ($R^3$), 4-tert-butyl-cyclohexancecarboxylic acid ($R^4$). The final crude product was purified using HPLC as described above, with a gradient of (B) 2, 0/2, 2/2, 6/20, 30/50. 1H NMR (400 MHz, CHLOROFORM-d) d ppm 10.21 (br. s., 1H) 8.60 (br. s., 2H) 4.35 (br. s., 1H) 3.84-4.06 (m, 3H) 3.78 (br. s., 2H) 3.67 (br. s., 2H) 3.40-3.59 (m, 3H) 3.27 (d, J=14.18 Hz, 2H) 3.01-3.21 (m, 2H) 2.83 (br. s., 1H) 2.63 (br. s., 1H) 2.24-2.38 (m, 2H) 2.19 (br. s., 1H) 1.95 (d, J=11.86 Hz, 1H) 1.83 (br. s., 1H) 1.70 (br. s., 3H) 1.52-1.67 (m, 8H) 1.40-1.52 (m, 4H) 1.34 (br. s., 1H) 1.24 (br. s., 3H) 1.16 (br. s., 5H) 0.99 (br. s., 5H) 0.93 (br. s., 4H) 0.85 (br. s., 8H); m/z calcd C37H69N7O [M+H]+ 628.56, found (MS ESI) 628.55. Purity LCMS: 98.41% (TIC), 99% (214 nm, peak area); RT=4.52 min.

TPI 2509-6 (R)-1-((S)-1-((R)-1-cyclohexyl-3-((S)-2-(((R)-2-imino-5-isobutylimidazolidin-1-yl)methyppyrrolidin-1-yl)propan-2-yl)-2-imino-3-(4-methylpentyl)imidazolidin-4-yl)ethanol (6)

Using General Scheme for the synthesis of bis-cyclic guanidines compound 2509-6 was synthesized using the following reagents: Boc-D-Leucine-OH·H2O ($R^1$), Boc-D-Cyclohexylalanine-OH ($R^2$), Boc-D-Threonine(Bzl)-OH ($R^3$), 4-Methylvaleric acid ($R^4$). The final crude product was purified using HPLC as described above, with a gradient of (B) 2, 0/2, 2/2, 6/20, 30/50. 1H NMR (400 MHz, CHLOROFORM-d) d ppm 10.06 (br. s., 1H) 8.59 (br. s., 2H) 4.24 (br. s., 2H) 3.96 (br. s., 2H) 3.84 (br. s., 1H) 3.78 (br. s., 1H) 3.71 (d, J=9.78 Hz, 2H) 3.44-3.58 (m, 1H) 3.42 (br. s., 1H) 3.28-3.38 (m, 2H) 3.23 (d, J=15.53 Hz, 2H) 2.81 (br. s., 1H) 2.72 (br. s., 1H) 2.35 (d, J=13.20 Hz, 2H) 1.81-1.93 (m, 2H) 1.73 (br. s., 3H) 1.63 (br. s., 3H) 1.50-1.60 (m, 4H) 1.45 (br. s., 2H) 1.36 (br. s., 1H) 1.17 (s, 3H) 1.21 (s, 5H) 0.98 (br. s., 4H) 0.79-0.95 (m, 9H); m/z calcd C32H61N7O [M+H]+ 560.49, found (MS ESI) 560.45. Purity LCMS: 96.78% (TIC), 99% (214 nm, peak area); RT=4.08 min.

TPI 2509-7 (R)-3-(adamantan-1-ylmethyl)-1-((R)-1-cyclohexyl-3-((S)-2-(((R)-2-imino-5-isobutylimidazolidin-1-yl)methyppyrrolidin-1-yl)propan-2-yl)-4-propylimidazolidin-2-imine (7)

Using General Scheme for the synthesis of bis-cyclic guanidines compound 2509-7 was synthesized using the following reagents: Boc-D-Leucine-OH·H2O ($R^1$), Boc-D-Cyclohexylalanine-OH ($R^2$), Boc-D-Norvaline-OH ($R^3$), 1-Adamantancecarboxylic acid ($R^4$). The final crude product was purified using HPLC as described above, with a gradient of (B) 2, 0/2, 2/2, 6/20, 30/50. 1H NMR (400 MHz, CHLOROFORM-d) d ppm 10.75 (br. s., 1H) 9.24 (br. s., 1H) 8.64 (br. s., 2H) 4.20 (br. s., 1H) 3.95 (br. s., 1H) 3.74 (br. s., 2H) 3.46-3.65 (m, 2H) 3.24-3.43 (m, 3H) 3.07-3.24 (m, 2H) 2.93 (br. s., 1H) 2.82 (br. s., 1H) 2.73 (d, J=15.77 Hz, 1H) 2.51-2.61 (m, 1H) 2.46 (d, J=13.33 Hz, 1H) 1.99 (br. s., 3H) 1.86-1.97 (m, 2H) 1.80 (br. s., 3H) 1.71 (br. s., 5H) 1.62 (s, 3H) 1.65 (s, 4H) 1.56 (br. s., 5H) 1.54 (br. s., 4H) 1.31 (br. s., 2H) 1.07-1.23 (m, 4H) 0.87-1.06 (m, 10H); m/z calcd C38H67N7 [M+H]+ 622.55, found (MS ESI) 622.5. Purity LCMS: 95.96% (TIC), 99% (214 nm, peak area); RT=4.73 min.

TPI 2509-8 (R)-3-((4-(tert-butyl)cyclohexyl)methyl)-1-((R)-1-cyclohexyl-3-((S)-2-(((R)-2-imino-5-isobutylimidazolidin-1-yl)methyl)pyrrolidin-1-yl)propan-2-yl)-4-propylimidazolidin-2-imine (8)

Using General Scheme for the synthesis of bis-cyclic guanidines compound 2509-8 was synthesized using the following reagents: Boc-D-Leucine-OH·H2O ($R^1$), Boc-D-Cyclohexylalanine-OH ($R^2$), Boc-D-Norvaline-OH ($R^3$), 4-tert-butyl-cyclohexancecarboxylic acid ($R^4$). The final crude product was purified using HPLC as described above, with a gradient of (B) 2, 0/2, 2/2, 6/20, 30/50. 1H NMR (400 MHz, CHLOROFORM-d) d ppm 8.62 (br. s., 2H) 4.19 (br. s., 1H) 3.90 (br. s., 1H) 3.84 (br. s., 1H) 3.74 (br. s., 2H) 3.59 (br. s., 1H) 3.39 (d, J=14.79 Hz, 1H) 3.29 (br. s., 2H) 3.19 (br. s., 2H) 3.05 (d, J=14.67 Hz, 1H) 2.92 (br. s., 1H) 2.83

(br. s., 1H) 2.54 (br. s., 1H) 2.47 (d, J=13.33 Hz, 1H) 2.09 (br. s., 1H) 1.83-1.96 (m, 2H) 1.81 (br. s., 2H) 1.73 (br. s., 3H) 1.49-1.66 (m, 9H) 1.43 (br. s., 4H) 1.35 (br. s., 2H) 1.16 (br. s., 6H) 0.89-1.04 (m, 11H) 0.86 (br. s., 9H); m/z calcd C38H71N7 [M+H]+ 626.58, found (MS ESI) 626.55. Purity LCMS: 97.36% (TIC), 99% (214 nm, peak area); RT=4.92 min.

TPI 2509-9 (R)-1-((R)-1-cyclohexyl-3-((S)-2-(((R)-2-imino-5-isobutylimidazolidin-1-yl)methyp-pyrrolidin-1-yl)propan-2-yl)-3-(4-methylpentyl)-4-propylimidazolidin-2-imine (9)

Using General Scheme for the synthesis of bis-cyclic guanidines compound 2509-9 was synthesized using the following reagents: Boc-D-Leucine-OH·H2O ($R^1$), Boc-D-Cyclohexylalanine-OH ($R^2$), Boc-D-Norvaline-OH ($R^3$), 4-Methylvaleric acid ($R^4$). The final crude product was purified using HPLC as described above, with a gradient of (B) 2, 0/2, 2/2, 6/20, 30/50. 1H NMR (400 MHz, CHLOROFORM-d) d ppm 8.59 (br. s., 2H) 4.11 (br. s., 1H) 3.79 (br. s., 1H) 3.63-3.75 (m, 3H) 3.55 (br. s., 1H) 3.38 (d, J=14.79 Hz, 1H) 3.25 (br. s., 2H) 3.02-3.19 (m, 3H) 2.88 (br. s., 1H) 2.80 (br. s., 1H) 2.37-2.52 (m, 2H) 1.72-1.88 (m, 4H) 1.64 (d, J=18.46 Hz, 4H) 1.52 (br. s., 5H) 1.24-1.46 (m, 6H) 1.14 (br. s., 6H) 0.81-1.01 (m, 17H); m/z calcd C33H63N7 [M+H]+ 558.51, found (MS ESI) 558.45. Purity LCMS: 97.89% (TIC), 99% (214 nm, peak area); RT=4.48 min.

TPI 2509-10 (R)-3-(adamantan-1-ylmethyl)-1-((R)-1-cyclohexyl-3-((S)-2-(((R)-2-imino-5-isobutyl-imidazolidin-1-yl)methyppyrrolidin-1-yl)propan-2-yl)-4-isopropylimidazolidin-2-imine (10)

Using General Scheme for the synthesis of bis-cyclic guanidines compound 2509-10 was synthesized using the following reagents: Boc-D-Leucine-OH·H2O ($R^1$), Boc-D-Cyclohexylalanine-OH ($R^2$), Boc-D-Valine-OH ($R^3$), 1-Adamantancecarboxylic acid ($R^4$). The final crude product was purified using HPLC as described above, with a gradient of (B) 2, 0/2, 2/2, 6/20, 25/45. 1H NMR (400 MHz, CHLOROFORM-d) d ppm 10.51 (br. s., 1H) 9.25 (br. s., 1H) 8.63 (br. s., 2H) 4.13 (br. s., 1H) 4.00 (br. s., 1H) 3.73 (br. s., 2H) 3.60 (d, J=15.28 Hz, 1H) 3.35-3.52 (m, 2H) 3.26 (br. s., 3H) 3.15 (d, J=14.79 Hz, 1H) 2.94 (br. s., 1H) 2.79-2.89 (m, 1H) 2.71 (d, J=15.41 Hz, 1H) 2.47 (d, J=10.76 Hz, 2H) 2.25 (br. s., 1H) 1.99 (br. s., 3H) 1.85-1.95 (m, 2H) 1.80 (br. s., 2H) 1.60-1.75 (m, 12H) 1.57 (br. s., 4H) 1.49 (br. s., 3H) 1.29-1.45 (m, 1H) 1.08-1.25 (m, 4H) 1.02 (br. s., 1H) 0.88-0.99 (m, 9H) 0.80 (br. s., 3H); m/z calcd C38H67N7 [M+H]+ 622.55, found (MS ESI) 622.5. Purity LCMS: 97.72% (TIC), 99% (214 nm, peak area); RT=4.72 min.

TPI 2509-11 (R)-3-((4-(tert-butyl)cyclohexyl)methyl)-1-((R)-1-cyclohexyl-3-((S)-2-(((R)-2-imino-5-isobutylimidazolidin-1-yl)methyl)pyrrolidin-1-yl)propan-2-yl)-4-isopropylimidazolidin-2-imine (11)

Using General Scheme for the synthesis of bis-cyclic guanidines compound 2509-11 was synthesized using the following reagents: Boc-D-Leucine-OH·H2O ($R^1$), Boc-D-Cyclohexylalanine-OH ($R^2$), Boc-D-Valine-OH ($R^3$), 4-tert-butyl-cyclohexancecarboxylic acid ($R^4$). The final crude product was purified using HPLC as described above, with a gradient of (B) 2, 0/2, 2/2, 6/20, 30/50. 1H NMR (400 MHz, CHLOROFORM-d) d ppm 8.63 (br. s., 2H) 4.15 (br. s., 1H) 3.97 (br. s., 1H) 3.86 (br. s., 1H) 3.73 (br. s., 3H) 3.36-3.58 (m, 2H) 3.28 (br. s., 3H) 3.17 (d, J=14.79 Hz, 1H) 3.01 (br. s., 1H) 2.92 (d, J=18.46 Hz, 2H) 2.39-2.59 (m, 2H) 2.14 (br. s., 2H) 1.76-1.92 (m, 5H) 1.71 (br. s., 2H) 1.66 (br. s., 3H) 1.52-1.62 (m, 5H) 1.48 (br. s., 2H) 1.43 (br. s., 2H) 0.95-1.22 (m, 14H) 0.92 (br. s., 4H) 0.84 (br. s., 11H); m/z calcd C38H71N7 [M+H]+ 626.58, found (MS ESI) 626.55. Purity LCMS: 98.51% (TIC), 99% (214 nm, peak area); RT=4.92 min.

TPI 2509-12 (R)-1-((R)-1-cyclohexyl-3-((S)-2-(((R)-2-imino-5-isobutylimidazolidin-1-yl)methyp-pyrrolidin-1-yl)propan-2-yl)-4-isopropyl-3-(4-methylpentyl)imidazolidin-2-imine (12)

Using General Scheme for the synthesis of bis-cyclic guanidines compound 2509-12 was synthesized using the following reagents: Boc-D-Leucine-OH·H2O ($R^1$), Boc-D-Cyclohexylalanine-OH ($R^2$), Boc-D-Valine-OH ($R^3$), 4-Methylvaleric acid ($R^4$). The final crude product was purified using HPLC as described above, with a gradient of (B) 2, 0/2, 2/2, 6/20, 25/45 1H NMR (400 MHz, CHLOROFORM-d) d ppm 8.62 (br. s., 2H) 4.09 (br. s., 1H) 3.87 (br. s., 1H) 3.73 (br. s., 3H) 3.35-3.59 (m, 2H) 3.26 (br. s., 3H) 3.14 (d, J=14.43 Hz, 1H) 3.06 (br. s., 1H) 2.81-2.98 (m, 2H) 2.40-2.52 (m, 2H) 2.16 (br. s., 1H) 1.87 (br. s., 1H) 1.82 (br. s., 2H) 1.68 (d, J=17.61 Hz, 4H) 1.57 (br. s., 4H) 1.35-1.53 (m, 5H) 1.18 (br. s., 6H) 0.97 (br. s., 7H) 0.75-0.93 (m, 12H); m/z calcd C33H63N7 [M+H]+ 558.51, found (MS ESI) 558.45. Purity LCMS: 96.02% (TIC), 98% (214 nm, peak area); RT=4.49 min.

TPI 2509-13 (R)-1-((S)-3-(adamantan-1-ylmethyl)-2-imino-1-((R)-1-((S)-2-(((R)-2-imino-5-isobutyl-imidazolidin-1-yl)methyl)pyrrolidin-1-yl)-3-phenyl-propan-2-yl)imidazolidin-4-yl)ethanol (13)

Using General Scheme for the synthesis of bis-cyclic guanidines compound 2509-13 was synthesized using the following reagents: Boc-D-Leucine-OH·H2O ($R^1$), Boc-D-Phenylalnine-OH ($R^2$), Boc-D-Threonine(Bzl)-OH ($R^3$), 1-Adamantancecarboxylic acid ($R^4$). The final crude product was purified using HPLC as described above, with a gradient of (B) 2, 0/2, 2/2, 6/20, 25/45. 1H NMR (400 MHz, CHLOROFORM-d) d ppm 10.14 (br. s., 1H) 8.94 (br. s., 1H) 8.63 (br. s., 2H) 8.38 (br. s., 1H) 7.35 (br. s., 2H) 7.21 (br. s., 2H) 4.74 (br. s., 1H) 4.04 (br. s., 3H) 3.84 (br. s., 2H) 3.67 (br. s., 1H) 3.58 (br. s., 1H) 3.51 (br. s., 1H) 3.42 (br. s., 1H) 3.36 (br. s., 1H) 3.21-3.33 (m, 2H) 2.92-3.19 (m, 3H) 2.70 (d, J=16.63 Hz, 3H) 2.47 (d, J=11.13 Hz, 1H) 2.33 (br. s., 1H) 1.78-1.93 (m, 3H) 1.64 (s, 3H) 1.67 (s, 2H) 1.50-1.60 (m, 5H) 1.41-1.50 (m, 1H) 1.30-1.41 (m, 3H) 1.16-1.27 (m, 3H) 1.11 (br. s., 3H) 1.00 (br. s., 3H) 0.94 (br. s., 3H); m/z calcd C37H59N7O [M+H]+ 618.48, found (MS ESI) 618.45. Purity LCMS: 98.23% (TIC), 99% (214 nm, peak area); RT=4.12 min.

TPI 2509-14 (R)-1-((S)-3-((4-(tert-butyl)cyclohexyl)methyl)-2-imino-1-((R)-1-((S)-2-(((R)-2-imino-5-isobutylimidazolidin-1-yl)methyl)pyrrolidin-1-yl)-3-phenylpropan-2-yl)imidazolidin-4-yl)ethanol (14)

Using General Scheme for the synthesis of bis-cyclic guanidines compound 2509-14 was synthesized using the following reagents: Boc-D-Leucine-OH·H2O ($R^1$), Boc-D-Phenylalnine-OH ($R^2$), Boc-D-Threonine(Bzl)-OH ($R^3$), 4-tert-butyl-cyclohexancecarboxylic acid ($R^4$). The final crude product was purified using HPLC as described above, with a gradient of (B) 2, 0/2, 2/2, 6/20, 25/40. 1H NMR (400 MHz, CHLOROFORM-d) d ppm 8.62 (br. s., 2H) 7.23 (br. s., 2H) 4.69 (br. s., 1H) 3.94 (br. s., 3H) 3.79 (br. s., 1H) 3.74 (br. s., 1H) 3.68 (br. s., 1H) 3.60 (br. s., 2H) 3.39-3.55 (m, 2H) 3.30 (br. s., 2H) 3.11 (br. s., 1H) 2.99 (d, J=13.20 Hz, 3H) 2.61-2.85 (m, 2H) 2.46 (d, J=11.49 Hz, 1H) 2.34 (br. s., 1H) 1.79-1.99 (m, 2H) 1.69 (br. s., 2H) 1.36-1.63 (m, 7H) 1.26 (br. s., 2H) 1.15 (br. s., 3H) 1.00 (br. s., 4H) 0.86-0.97 (m, 5H) 0.83 (br. s., 9H); m/z calcd C37H63N7O [M+H]+ 622.51, found (MS ESI) 622.5. Purity LCMS: 98.73% (TIC), 99% (214 nm, peak area); RT=4.33 min.

TPI 2509-15 (R)-1-((S)-2-imino-1-((R)-1-((S)-2-(((R)-2-imino-5-isobutylimidazolidin-1-yl)methyl)pyrrolidin-1-yl)-3-phenylpropan-2-yl)-3-(4-methylpentyl)imidazolidin-4-yl)ethanol (15)

Using General Scheme for the synthesis of bis-cyclic guanidines compound 2509-15 was synthesized using the following reagents: Boc-D-Leucine-OH·H2O (R$^1$), Boc-D-Phenylalnine-OH (R$^2$), Boc-D-Threonine(Bzl)-OH (R$^3$), 4-Methylvaleric acid (R$^4$). The final crude product was purified using HPLC as described above, with a gradient of (B) 2, 0/2, 2/2, 6/20, 25/45. 1H NMR (400 MHz, CHLOROFORM-d) d ppm 10.01 (br. s., 1H) 9.01 (br. s., 1H) 8.59 (br. s., 2H) 7.29 (br. s., 2H) 7.23 (br. s., 2H) 4.61 (br. s., 1H) 4.14 (br. s., 2H) 3.90 (br. s., 2H) 3.78 (br. s., 1H) 3.60-3.75 (m, 2H) 3.38-3.59 (m, 3H) 3.27 (br. s., 2H) 3.12 (br. s., 2H) 2.97 (br. s., 2H) 2.74 (d, J=12.96 Hz, 2H) 2.46 (d, J=12.35 Hz, 1H) 2.40 (br. s., 1H) 1.87 (br. s., 1H) 1.72 (br. s., 2H) 1.54 (d, J=11.74 Hz, 3H) 1.40-1.50 (m, 2H) 1.35 (br. s., 1H) 1.24 (br. s., 1H) 1.13 (br. s., 3H) 0.99 (br. s., 4H) 0.93 (br. s., 3H) 0.86 (br. s., 5H); m/z calcd C32H55N7O [M+H]+ 554.45, found (MS ESI) 554.4. Purity LCMS: 98.87% (TIC), 99% (214 nm, peak area); RT=3.86 min.

TPI 2509-16 (R)-3-(adamantan-1-ylmethyl)-1-((R)-1-((S)-2-(((R)-2-imino-5-isobutylimidazolidin-1-yl)methyl)pyrrolidin-1-yl)-3-phenylpropan-2-yl)-4-propylimidazolidin-2-imine (16)

Using General Scheme for the synthesis of bis-cyclic guanidines compound 2509-16 was synthesized using the following reagents: Boc-D-Leucine-OH·H2O (R$^1$), Boc-D-Phenylalnine-OH (R$^2$), Boc-D-Norvaline-OH (R$^3$), 1-Adamantancecarboxylic acid (R$^4$). The final crude product was purified using HPLC as described above, with a gradient of (B) 2, 0/2, 2/2, 6/20, 30/35. 1H NMR (400 MHz, CHLOROFORM-d) d ppm 10.74 (br. s., 1H) 9.43 (br. s., 1H) 8.66 (br. s., 2H) 7.40 (br. s., 2H) 7.29 (br. s., 2H) 7.21 (br. s., 1H) 4.75 (br. s., 1H) 3.73 (br. s., 4H) 3.58 (br. s., 2H) 3.27 (br. s., 4H) 3.20 (br. s., 1H) 3.10 (d, J=13.94 Hz, 1H) 2.99 (br. s., 2H) 2.77 (t, J=11.80 Hz, 1H) 2.47-2.70 (m, 3H) 2.00 (br. s., 1H) 1.90 (br. s., 3H) 1.74-1.86 (m, 2H) 1.66 (d, J=11.62 Hz, 4H) 1.49-1.60 (m, 5H) 1.28-1.46 (m, 4H) 1.22 (br. s., 5H) 0.88-1.07 (m, 8H); m/z calcd C38H61N7 [M+H]+ 616.50, found (MS ESI) 616.5. Purity LCMS: 98.41% (TIC), 99% (214 nm, peak area); RT=4.50 min.

TPI 2509-17 (R)-3-((4-(tert-butyl)cyclohexyl)methyl)-1-((R)-1-((S)-2-(((R)-2-imino-5-isobutylimidazolidin-1-yl)methyppyrrolidin-1-yl)-3-phenylpropan-2-yl)-4-propylimidazolidin-2-imine (17)

Using General Scheme for the synthesis of bis-cyclic guanidines compound 2509-17 was synthesized using the following reagents: Boc-D-Leucine-OH·H2O (R$^1$), Boc-D-Phenylalnine-OH (R$^2$), Boc-D-Norvaline-OH (R$^3$), 4-tert-butyl-cyclohexancecarboxylic acid (R$^4$). The final crude product was purified using HPLC as described above, with a gradient of (B). 1H NMR (400 MHz, CHLOROFORM-d) d ppm 8.65 (br. s., 2H) 7.35 (br. s., 3H) 7.22 (br. s., 1H) 4.70 (br. s., 1H) 3.73 (br. s., 3H) 3.48-3.68 (m, 3H) 3.25-3.45 (m, 3H) 3.16-3.25 (m, 1H) 3.01-3.15 (m, 2H) 2.98 (br. s., 1H) 2.89 (d, J=14.79 Hz, 1H) 2.73-2.85 (m, 1H) 2.62 (d, J=11.37 Hz, 2H) 1.86-1.99 (m, 1H) 1.81 (br. s., 3H) 1.66 (br. s., 1H) 1.48-1.62 (m, 4H) 1.33-1.47 (m, 3H) 1.24 (br. s., 3H) 1.05-1.19 (m, 1H) 0.88-1.02 (m, 11H) 0.84 (br. s., 9H); m/z calcd C38H65N7 [M+H]+ 620.53, found (MS ESI) 620.5. Purity LCMS: 98.68% (TIC), 99% (214 nm, peak area); RT=4.69 min.

TPI 2509-18 (R)-1-((R)-1-((S)-2-(((R)-2-imino-5-isobutylimidazolidin-1-yl)methyl)pyrrolidin-1-yl)-3-phenylpropan-2-yl)-3-(4-methylpentyl)-4-propylimidazolidin-2-imine (18)

Using General Scheme for the synthesis of bis-cyclic guanidines compound 2509-18 was synthesized using the following reagents: Boc-D-Leucine-OH·H2O (R$^1$), Boc-D-Phenylalnine-OH (R$^2$), Boc-D-Norvaline-OH (R$^3$), 4-Methylvaleric acid (R$^4$). The final crude product was purified using HPLC as described above, with a gradient of (B) 2, 0/2, 2/2, 6/20, 30/30. 1H NMR (400 MHz, CHLOROFORM-d) d ppm 10.53 (br. s., 1H) 9.34 (br. s., 1H) 8.61 (br. s., 2 H) 7.30 (br. s., 2H) 7.20 (br. s., 2H) 4.54 (br. s., 1H) 4.08 (br. s., 1H) 3.72 (br. s., 2H) 3.56 (br. s., 2H) 3.45 (br. s., 1H) 3.14-3.39 (m, 4H) 2.89-3.09 (m, 4H) 2.72-2.89 (m, 1H) 2.60 (d, J=14.06 Hz, 2H) 1.90 (br. s., 1H) 1.78 (br. s., 2H) 1.65 (br. s., 1H) 1.33-1.60 (m, 5H) 1.22 (br. s., 4H) 0.91 (s, 5H) 0.95 (s, 5H) 0.83 (br. s., 5H); m/z calcd C33H57N7 [M+H]+ 552.47, found (MS ESI) 552.4. Purity LCMS: 98.02% (TIC), 99% (214 nm, peak area); RT=4.29 min.

TPI 2509-19 (R)-3-(adamantan-1-ylmethyl)-1-((R)-1-((S)-2-(((R)-2-imino-5-isobutylimidazolidin-1-yl)methyl)pyrrolidin-1-yl)-3-phenylpropan-2-yl)-4-isopropylimidazolidin-2-imine (19)

Using General Scheme for the synthesis of bis-cyclic guanidines compound 2509-19 was synthesized using the following reagents: Boc-D-Leucine-OH·H2O (R$^1$), Boc-D-Phenylalnine-OH (R$^2$), Boc-D-Valine-OH (R$^3$), 1-Adamantancecarboxylic acid (R$^4$). The final crude product was purified using HPLC as described above, with a gradient of (B) 2, 0/2, 2/2, 6/20, 30/30, 35/35. 1H NMR (400 MHz, CHLOROFORM-d) d ppm 10.00 (br. s., 1H) 9.13 (br. s., 1H) 8.64 (br. s., 1H) 7.42 (br. s., 2H) 7.29 (br. s., 1H) 7.20 (br. s., 2H) 4.71 (br. s., 1H) 3.75 (br. s., 2H) 3.70 (br. s., 1H) 3.50 (br. s., 2H) 3.32-3.45 (m, 3H) 3.27 (br. s., 3H) 3.13 (d, J=14.18 Hz, 1H) 3.02 (br. s., 2H) 2.77-2.95 (m, 1H) 2.48-2.74 (m, 3H) 2.15 (br. s., 1H) 2.01 (br. s., 1H) 1.89 (br. s., 3H) 1.79 (br. s., 2H) 1.63 (br. s., 3H) 1.55 (br. s., 5H) 1.37 (d, J=11.00 Hz, 4H) 1.10-1.30 (m, 3H) 0.83-1.04 (m, 8H) 0.74 (br. s., 3H); m/z calcd C38H61N7 [M+H]+ 616.50, found (MS ESI) 616.45. Purity LCMS: 98.05% (TIC), 98% (214 nm, peak area); RT=4.51 min.

TPI 2509-20 (R)-3-((4-(tert-butyl)cyclohexyl)methyl)-1-((R)-1-((S)-2-(((R)-2-imino-5-isobutylimidazolidin-1-yl)methyl)pyrrolidin-1-yl)-3-phenylpropan-2-yl)-4-isopropylimidazolidin-2-imine (20)

Using General Scheme for the synthesis of bis-cyclic guanidines compound 2509-20 was synthesized using the following reagents: Boc-D-Leucine-OH·H2O ($R^1$), Boc-D-Phenylalnine-OH ($R^2$), Boc-D-Valine-OH ($R^3$), 4-tert-butyl-cyclohexancecarboxylic acid ($R^4$). The final crude product was purified using HPLC as described above, with a gradient of (B) 2, 0/2, 2/2, 6/20, 30/30. 1H NMR (400 MHz, CHLOROFORM-d) d ppm 8.64 (br. s., 2H) 7.32 (br. s., 2H) 7.20 (br. s., 2H) 4.63 (br. s., 1H) 3.69 (d, J=9.90 Hz, 3H) 3.56 (br. s., 1H) 3.41 (br. s., 1H) 3.27-3.37 (m, 1H) 3.23 (br. s., 3H) 3.07 (d, J=13.69 Hz, 1H) 2.94 (br. s., 2H) 2.71-2.90 (m, 2H) 2.46-2.69 (m, 2H) 2.00 (br. s., 1H) 1.90 (br. s., 1H) 1.78 (br. s., 3H) 1.44-1.65 (m, 4H) 1.37 (d, J=15.65 Hz, 3H) 1.23 (br. s., 1H) 1.03-1.17 (m, 1H) 0.96 (br. s., 4H) 0.90 (br. s., 7H) 0.82 (br. s., 9H) 0.75 (br. s., 4H); m/z calcd C38H65N7 [M+H]+ 620.53, found (MS ESI) 620.5. Purity LCMS: 98.57% (TIC), 99% (214 nm, peak area); RT=4.71 min.

TPI 2509-21 (R)-1-((R)-1-((S)-2-(((R)-2-imino-5-isobutylimidazolidin-1-yl)methyl)pyrrolidin-1-yl)-3-phenylpropan-2-yl)-4-isopropyl-3-(4-methylpentyl)imidazolidin-2-imine (21)

Using General Scheme for the synthesis of bis-cyclic guanidines compound 2509-21 was synthesized using the following reagents: Boc-D-Leucine-OH·H2O ($R^1$), Boc-D-Phenylalnine-OH ($R^2$), Boc-D-Valine-OH ($R^3$), 4-Methylvaleric acid ($R^4$). The final crude product was purified using HPLC as described above, with a gradient of (B) 2, 0/2, 2/2, 6/20, 30/30. 1H NMR (400 MHz, DMSO-d6): δ 8.5 (br. s., 2H) 7.4 (d, J=7.1 Hz, 4H) 7.2-7.3 (m, 17H) 7.2 (d, J=7.2 Hz, 6H) 3.7-3.9 (m, 5H) 3.7 (d, J=9.4 Hz, 2H) 3.5 (d, J=12.7 Hz, 3H) 3.3 (d, J=12.6 Hz, 4H) 3.1 (d, J=12.8 Hz, 2H) 2.9-3.0 (m, 7H) 2.7-2.9 (m, 11H) 2.6 (br. s., 4H) 2.0-2.2 (m, 4H) 1.9 (d, J=11.74 Hz, 4H) 1.5-1.7 (m, 12H) 1.2 (br. s., 5H) 1.2 (br. s., 6H) 0.8-1.1 (m, 4H) 13C NMR (100 MHz, DMSO-d6) δ 158.0, 157.8, 157.3, 156.8, 139.2, 137.9, 137.7, 129.8, 129.4, 129.1, 129.0, 128.8, 127.3, 127.1, 126.8, 62.8, 58.5, 55.6, 53.8, 51.2, 48.4, 40.7, 40.5, 37.9, 37.8, 37.5, 34.5, 33.6, 33.5, 32.8, 29.6, 26.6, 26.3, 26.1, 22.8; m/z calcd C33H57N7 [M+H]+ 552.47, found (MS ESI) 552.45. Purity LCMS: 97.09% (TIC), 99% (214 nm, peak area); RT=4.26 min.

TPI 2509-22 (R)-1-((S)-3-(adamantan-1-ylmethyl)-1-((R)-1-cyclohexyl-3-((S)-2-(((R)-2-imino-5-isopropylimidazolidin-1-yl)methyl)pyrrolidin-1-yl)propan-2-yl)-2-iminoimidazolidin-4-yl)ethanol (22)

Using General Scheme for the synthesis of bis-cyclic guanidines compound 2509-22 was synthesized using the following reagents: Boc-D-Valine-OH ($R^1$), Boc-D-Cyclohexylalanine-OH ($R^2$), Boc-D-Threonine(Bzl)-OH ($R^3$), 1-Adamantancecarboxylic acid ($R^4$). The final crude product was purified using HPLC as described above, with a gradient of (B) 2, 0/2, 2/2, 6/20, 30/30. 1H NMR (400 MHz, CHLOROFORM-d) d ppm 10.01 (br. s., 1H) 8.74-9.01 (m, 1H) 8.58 (br. s., 2H) 4.27 (br. s., 2H) 4.06 (br. s., 2H) 3.92 (br. s., 1H) 3.79 (br. s., 1H) 3.59 (d, J=15.04 Hz, 1H) 3.42-3.54 (m, 3H) 3.38 (br. s., 1H) 3.18 (d, J=16.63 Hz, 2H) 2.95 (d, J=14.79 Hz, 1H) 2.78 (br. s., 1H) 2.69 (br. s., 1H) 2.30 (br. s., 2H) 2.06 (br. s., 1H) 1.97 (br. s., 3H) 1.82 (br. s., 1H) 1.69 (br. s., 6H) 1.43-1.65 (m, 11H) 1.33 (br. s., 1H) 1.15 (br. s., 6H) 0.98 (d, J=11.74 Hz, 2H) 0.90 (br. s., 3H) 0.84 (br. s., 3H); m/z calcd C36H63N7O [M+H]+ 610.51, found (MS ESI) 610.5. Purity LCMS: 97.44% (TIC), 99% (214 nm, peak area); RT=4.11 min.

TPI 2509-23 (R)-1-((S)-3-((4-(tert-butyl)cyclohexyl)methyl)-1-((R)-1-cyclohexyl-3-((S)-2-(((R)-2-imino-5-isopropylimidazolidin-1-yl)methyl)pyrrolidin-1-yl)propan-2-yl)-2-iminoimidazolidin-4-yl)ethanol (23)

Using General Scheme for the synthesis of bis-cyclic guanidines compound 2509-23 was synthesized using the following reagents: Boc-D-Valine-OH ($R^1$), Boc-D-Cyclohexylalanine-OH ($R^2$), Boc-D-Threonine(Bzl)-OH ($R^3$), 4-tert-butyl-cyclohexancecarboxylic acid ($R^4$). The final crude product was purified using HPLC as described above, with a gradient of (B) 2, 0/2, 2/2, 6/20, 30/30. 1H NMR (400 MHz, CHLOROFORM-d) d ppm 8.58 (br. s., 2H) 4.05-4.34 (m, 3H) 3.98 (br. s., 2H) 3.88 (br. s., 1H) 3.80 (br. s., 2H) 3.42-3.65 (m, 3H) 3.40 (br. s., 1H) 3.31 (br. s., 1H) 3.18 (br. s., 2H) 2.69-2.87 (m, 2H) 2.34 (d, J=13.08 Hz, 2H) 2.19 (br. s., 1H) 2.08 (br. s., 1H) 1.78-1.97 (m, 2H) 1.71 (br. s., 4H) 1.48-1.67 (m, 6H) 1.42 (br. s., 1H) 1.34 (br. s., 1H) 1.05-1.23 (m, 8H) 0.96 (br. s., 3H) 0.90 (br. s., 4H) 0.83 (br. s., 11H); m/z calcd C36H67N7O [M+H]+ 614.54, found (MS ESI) 614.55. Purity LCMS: 98.01% (TIC), 99% (214 nm, peak area); RT=4.35 min.

TPI 2509-24 (R)-1-((S)-1-((R)-1-cyclohexyl-3-((S)-2-(((R)-2-imino-5-isopropylimidazolidin-1-yl)methyl)pyrrolidin-1-yl)propan-2-yl)-2-imino-3-(4-methylpentyl)imidazolidin-4-yl)ethanol (24)

Using General Scheme for the synthesis of bis-cyclic guanidines compound 2509-24 was synthesized using the following reagents: Boc-D-Valine-OH ($R^1$), Boc-D-Cyclohexylalanine-OH ($R^2$), Boc-D-Threonine(Bzl)-OH ($R^3$), 4-Methylvaleric acid ($R^4$). The final crude product was purified using HPLC as described above, with a gradient of (B) 2, 0/2, 2/2, 6/20, 30/30. 1H NMR (400 MHz, CHLOROFORM-d) d ppm 9.05 (br. s., 1H) 8.59 (br. s., 2H) 4.21 (br. s., 3H) 3.95 (br. s., 2H) 3.80 (br. s., 3H) 3.55 (br. s., 1H) 3.48 (br. s., 1H) 3.30-3.44 (m, 3H) 3.20 (br. s., 2H) 2.77 (br. s., 2H) 2.26-2.48 (m, 2H) 2.07 (br. s., 1H) 1.87 (br. s., 2H) 1.72 (br. s., 3H) 1.63 (br. s., 3H) 1.49-1.59 (m, 3H) 1.42 (br. s., 1H) 1.36 (br. s., 1H) 1.17 (br. s., 8H) 0.99 (br. s., 1H) 0.76-0.95 (m, 12H); m/z calcd C31H59N7O [M+H]+ 546.48, found (MS ESI) 546.45. Purity LCMS: 97.57% (TIC), 99% (214 nm, peak area); RT=3.88 min.

TPI 2509-25 (R)-3-(adamantan-1-ylmethyl)-1-((R)-1-cyclohexyl-3-((S)-2-(((R)-2-imino-5-isopropylimidazolidin-1-yl)methyl)pyrrolidin-1-yl)propan-2-yl)-4-propylimidazolidin-2-imine (25)

Using General Scheme for the synthesis of bis-cyclic guanidines compound 2509-25 was synthesized using the following reagents: Boc-D-Valine-OH ($R^1$), Boc-D-Cyclohexylalanine-OH ($R^2$), Boc-D-Norvaline-OH ($R^3$), 1-Adamantancecarboxylic acid ($R^4$). The final crude product was purified using HPLC as described above, with a gradient of (B) 2, 0/2, 2/2, 6/20, 30/30. 1H NMR (400 MHz, CHLOROFORM-d) d ppm 10.54 (br. s., 1H) 9.28 (br. s., 1H) 8.61 (br. s., 2H) 4.16 (br. s., 1H) 3.93 (br. s., 1H) 3.75 (br. s., 1H) 3.48-3.60 (m, 3H) 3.33-3.46 (m, 2H) 3.25 (br. s., 1H) 3.06-3.22 (m, 2H) 2.92 (br. s., 1H) 2.80 (br. s., 1H) 2.71 (d, J=15.28 Hz, 1H) 2.48-2.55 (m, 1H) 2.44 (d, J=13.08 Hz, 1H) 2.06 (br. s., 1H) 1.97 (br. s., 3H) 1.83-1.93 (m, 2H) 1.78 (br. s., 3H) 1.68 (br. s., 5H) 1.59 (s, 3H) 1.63 (s, 4H) 1.54 (br. s., 4H) 1.40 (br. s., 3H) 1.24-1.34 (m, 2H) 1.07-1.23 (m, 4H) 0.92-1.06 (m, 4H) 0.89 (br. s., 3H) 0.81 (br. s., 3H); m/z calcd C37H65N7 [M+H]+ 608.53, found (MS ESI) 608.5. Purity LCMS: 96.94% (TIC), 98% (214 nm, peak area); RT=4.55 min.

TPI 2509-26 (R)-3-((4-(tert-butyl)cyclohexyl)
methyl)-1-((R)-1-cyclohexyl-3-((S)-2-(((R)-2-imino-
5-isopropylimidazolidin-1-yl)methyl)pyrrolidin-1-yl)
propan-2-yl)-4-propylimidazolidin-2-imine (26)

Using General Scheme for the synthesis of bis-cyclic guanidines compound 2509-26 was synthesized using the following reagents: Boc-D-Valine-OH ($R^1$), Boc-D-Cyclohexylalanine-OH ($R^2$), Boc-D-Norvaline-OH ($R^3$), 4-tert-butyl-cyclohexancecarboxylic acid ($R^4$). The final crude product was purified using HPLC as described above, with a gradient of (B) 2, 0/2, 2/2, 6/20, 30/30. 1H NMR (400 MHz, CHLOROFORM-d) d ppm 8.60 (br. s., 2H) 4.16 (br. s., 1H) 3.87 (br. s., 1H) 3.76 (br. s., 2H) 3.58 (br. s., 2H) 3.33-3.49 (m, 2H) 3.27 (br. s., 1H) 3.10-3.21 (m, 2H) 3.03 (d, J=13.82 Hz, 1H) 2.91 (br. s., 1H) 2.81 (br. s., 1H) 2.53 (br. s., 1H) 2.44 (d, J=12.84 Hz, 1H) 2.07 (br. s., 2H) 1.86 (br. s., 2H) 1.78 (br. s., 3H) 1.71 (br. s., 2H) 1.62 (br. s., 2H) 1.46-1.59 (m, 5H) 1.40 (br. s., 3H) 1.31 (br. s., 2H) 1.06-1.22 (m, 5H) 0.96 (br. s., 5H) 0.90 (br. s., 4H) 0.83 (br. s., 12H); m/z calcd C37H69N7 [M+H]+ 612.56, found (MS ESI) 612.55. Purity LCMS: 97.60% (TIC), 98% (214 nm, peak area); RT=4.78 min.

TPI 2509-27 (R)-1-((R)-1-cyclohexyl-3-((S)-2-
(((R)-2-imino-5-isopropylimidazolidin-1-yl)methyp-
pyrrolidin-1-yl)propan-2-yl)-3-(4-methylpentyl)-4-
propylimidazolidin-2-imine (27)

Using General Scheme for the synthesis of bis-cyclic guanidines compound 2509-27 was synthesized using the following reagents: Boc-D-Valine-OH ($R^1$), Boc-D-Cyclohexylalanine-OH ($R^2$), Boc-D-Norvaline-OH ($R^3$), 4-Methylvaleric acid ($R^4$). The final crude product was purified using HPLC as described above, with a gradient of (B) 2, 0/2, 2/2, 6/20, 30/30. 1H NMR (400 MHz, CHLOROFORM-d) d ppm 10.43 (br. s., 1H) 8.59 (br. s., 2H) 4.14 (br. s., 2H) 3.79 (br. s., 2H) 3.69 (br. s., 1H) 3.59 (br. s., 2H) 3.35-3.52 (m, 2H) 3.26 (br. s., 1H) 3.06-3.22 (m, 3H) 2.94 (br. s., 1H) 2.84 (br. s., 1H) 2.53 (br. s., 1H) 2.45 (d, J=13.08 Hz, 1H) 2.09 (br. s., 1H) 1.80 (br. s., 4H) 1.70 (br. s., 1H) 1.64 (br. s., 2H) 1.38-1.60 (m, 6H) 1.32 (br. s., 2H) 1.17 (br. s., 6H) 0.93-1.05 (m, 5H) 0.73-0.93 (m, 12H); m/z calcd C32H61N7 [M+H]+ 544.50, found (MS ESI) 544.45. Purity LCMS: 98.63% (TIC), 99% (214 nm, peak area); RT=4.34 min.

TPI 2509-28 (R)-3-(adamantan-1-ylmethyl)-1-((R)-
1-cyclohexyl-3-((S)-2-(((R)-2-imino-5-isopropylimi-
dazolidin-1-yl)methyl)pyrrolidin-1-yl)propan-2-yl)-
4-isopropylimidazolidin-2-imine (28)

Using General Scheme for the synthesis of bis-cyclic guanidines compound 2509-28 was synthesized using the following reagents: Boc-D-Valine-OH ($R^1$), Boc-D-Cyclohexylalanine-OH ($R^2$), Boc-D-Valine-OH ($R^3$), 1-Adamantancecarboxylic acid ($R^4$). The final crude product was purified using HPLC as described above, with a gradient of (B) 2, 0/2, 2/2, 6/20, 30/30 1H NMR (400 MHz, CHLOROFORM-d) d ppm 10.42 (br. s., 1H) 9.18 (br. s., 1H) 8.62 (br. s., 2H) 4.08 (br. s., 1H) 3.99 (br. s., 1H) 3.77 (br. s., 1H) 3.55-3.68 (m, 1H) 3.53 (br. s., 1H) 3.47 (br. s., 1H) 3.36 (br. s., 1H) 3.26 (br. s., 2H) 3.12 (d, J=14.67 Hz, 1H) 2.92 (br. s., 1H) 2.81 (br. s., 1H) 2.71 (d, J=15.77 Hz, 1H) 2.37-2.53 (m, 2H) 2.25 (br. s., 1H) 2.05 (br. s., 1H) 1.98 (br. s., 3H) 1.88 (br. s., 2H) 1.80 (br. s., 2H) 1.59-1.75 (m, 11H) 1.36-1.59 (m, 6H) 1.08-1.29 (m, 4H) 1.02 (br. s., 1H) 0.89 (s, 3H) 0.93 (s, 3H) 0.80 (br. s., 5H); m/z calcd C37H65N7 [M+H]+ 608.53, found (MS ESI) 608.55. Purity LCMS: 96.79% (TIC), 99% (214 nm, peak area); RT=4.55 min.

TPI 2509-29 (R)-3-((4-(tert-butyl)cyclohexyl)
methyl)-1-((R)-1-cyclohexyl-3-((S)-2-(((R)-2-imino-
5-isopropylimidazolidin-1-yl)methyl)pyrrolidin-1-yl)
propan-2-yl)-4-isopropylimidazolidin-2-imine (29)

Using General Scheme for the synthesis of bis-cyclic guanidines compound 2509-29 was synthesized using the following reagents: Boc-D-Valine-OH ($R^1$), Boc-D-Cyclohexylalanine-OH ($R^2$), Boc-D-Valine-OH ($R^3$), 4-tert-butyl-cyclohexancecarboxylic acid ($R^4$). The final crude product was purified using HPLC as described above, with a gradient of (B) 2, 0/2, 2/2, 6/20, 30/30. 1H NMR (400 MHz, CHLOROFORM-d) d ppm 8.61 (br. s., 2H) 4.06 (br. s., 1H) 3.86-3.99 (m, 1H) 3.82 (br. s., 1H) 3.75 (br. s., 1H) 3.53 (d, J=12.47 Hz, 2H) 3.38-3.49 (m, 1H) 3.36 (br. s., 1H) 3.25 (br. s., 2H) 3.12 (d, J=14.43 Hz, 1H) 2.97 (d, J=14.43 Hz, 1H) 2.90 (br. s., 1H) 2.81 (br. s., 1H) 2.40-2.50 (m, 2H) 2.08 (br. s., 2H) 1.75-1.93 (m, 4H) 1.66-1.75 (m, 2H) 1.63 (br. s., 2H) 1.48-1.59 (m, 5H) 1.44 (br. s., 2H) 1.13 (br. s., 5H) 0.94 (br. s., 6H) 0.88 (br. s., 4H) 0.83 (br. s., 14H); m/z calcd C37H69N7 [M+H]+ 612.56, found (MS ESI) 612.55. Purity LCMS: 98.26% (TIC), 99% (214 nm, peak area); RT=4.79 min.

TPI 2509-30 (R)-1-((R)-1-cyclohexyl-3-((S)-2-
(((R)-2-imino-5-isopropylimidazolidin-1-yl)methyl)
pyrrolidin-1-yl)propan-2-yl)-4-isopropyl-3-(4-meth-
ylpentyl)imidazolidin-2-imine (30)

Using General Scheme for the synthesis of bis-cyclic guanidines compound 2509-30 was synthesized using the following reagents: Boc-D-Valine-OH ($R^1$), Boc-D-Cyclohexylalanine-OH ($R^2$), Boc-D-Valine-OH ($R^3$), 4-Methylvaleric acid ($R^4$). The final crude product was purified using HPLC as described above, with a gradient of (B) 2, 0/2, 2/2, 6/20, 30/30. 1H NMR (400 MHz, CHLOROFORM-d) d ppm 8.59 (br. s., 2H) 4.05 (br. s., 2H) 3.84 (br. s., 1H) 3.75 (br. s., 2H) 3.32-3.60 (m, 4H) 3.19-3.30 (m, 2H) 3.12 (d, J=14.67 Hz, 1H) 3.03 (br. s., 1H) 2.77-2.97 (m, 2H) 2.38-2.50 (m, 2H) 2.13 (br. s., 1H) 2.05 (br. s., 1H) 1.80 (br. s., 4H) 1.66 (d, J=17.85 Hz, 4H) 1.54 (br. s., 3H) 1.45 (br. s., 2H) 1.15 (br. s., 6H) 0.94 (br. s., 4H) 0.86 (br. s., 10H) 0.80 (br. s., 5H); m/z calcd C32H61N7 [M+H]+ 544.50, found (MS ESI) 544.5. Purity LCMS: 98.73% (TIC), 99% (214 nm, peak area); RT=4.33 min.

TPI 2509-31 (R)-1-((S)-3-(adamantan-1-ylmethyl)-
2-imino-1-((R)-1-((S)-2-(((R)-2-imino-5-isopropy-
limidazolidin-1-yl)methyl)pyrrolidin-1-yl)-3-phenyl-
propan-2-yl)imidazolidin-4-yl)ethanol (31)

Using General Scheme for the synthesis of bis-cyclic guanidines compound 2509-31 was synthesized using the following reagents: Boc-D-Valine-OH ($R^1$), Boc-D-Phenylalnine-OH ($R^2$), Boc-D-Threonine(Bzl)-OH ($R^3$), 1-Adamantancecarboxylic acid ($R^4$). The final crude product was purified using HPLC as described above, with a gradient of (B) 2, 0/2, 2/2, 6/20, 30/30. 1H NMR (400 MHz, CHLOROFORM-d) d ppm 8.96 (br. s., 1H) 8.63 (br. s., 2H) 8.32

(br. s., 1H) 7.39 (br. s., 2H) 7.29 (br. s., 1H) 7.21 (br. s., 1H) 4.79 (br. s., 1H) 4.02 (br. s., 2H) 3.81 (br. s., 3H) 3.46-3.66 (m, 3H) 3.29-3.46 (m, 2H) 3.22 (d, J=12.72 Hz, 1H) 3.13 (br. s., 1H) 3.05 (d, J=13.20 Hz, 1H) 2.95 (br. s., 1H) 2.81 (br. s., 1H) 2.73 (br. s., 2H) 2.52 (d, J=10.64 Hz, 1H) 2.38 (br. s., 1H) 2.10 (br. s., 1H) 1.88 (br. s., 3H) 1.59-1.76 (m, 4H) 1.55 (br. s., 4H) 1.32 (br. s., 3H) 1.06-1.23 (m, 5H) 1.01 (br. s., 1H) 0.94 (br. s., 2H) 0.88 (br. s., 3H); m/z calcd C36H57N7O [M+H]+ 604.46, found (MS ESI) 614.45. Purity LCMS: 97.03% (TIC), 99% (214 nm, peak area); RT=3.92 min.

TPI 2509-32 (R)-1-((S)-3-((4-(tert-butyl)cyclohexyl)methyl)-2-imino-1-((R)-1-((S)-2-(((R)-2-imino-5-isopropylimidazolidin-1-yl)methyl)pyrrolidin-1-yl)-3-phenylpropan-2-yl)imidazolidin-4-yl)ethanol (32)

Using General Scheme for the synthesis of bis-cyclic guanidines compound 2509-32 was synthesized using the following reagents: Boc-D-Valine-OH ($R^1$), Boc-D-Phenylalnine-OH ($R^2$), Boc-D-Threonine(Bzl)-OH ($R^3$), 4-tert-butyl-cyclohexancecarboxylic acid ($R^4$). The final crude product was purified using HPLC as described above, with a gradient of (B) 2, 0/2, 2/2, 6/20, 30/30. 1H NMR (400 MHz, CHLOROFORM-d) d ppm 10.00 (br. s., 1H) 8.59 (br. s., 2H) 7.31 (br. s., 2H) 7.21 (br. s., 2H) 4.68 (br. s., 1H) 4.20 (br. s., 2H) 3.92 (br. s., 1H) 3.81 (br. s., 1H) 3.66 (br. s., 1H) 3.44-3.62 (m, 4H) 3.40 (br. s., 1H) 3.20 (d, J=13.33 Hz, 1H) 3.12 (br. s., 1H) 2.87-3.07 (m, 2H) 2.62-2.83 (m, 2H) 2.50 (d, J=11.37 Hz, 1H) 2.40 (br. s., 1H) 2.09 (br. s., 1H) 1.86 (br. s., 1H) 1.70 (br. s., 2H) 1.51 (br. s., 2H) 1.36 (br. s., 2H) 1.07-1.27 (m, 4H) 1.00 (br. s., 1H) 0.92 (br. s., 3H) 0.77-0.89 (m, 13H) 0.66 (br. s., 1H); m/z calcd C36H61N7O [M+H]+ 608.49, found (MS ESI) 608.45. Purity LCMS: 98.13% (TIC), 99% (214 nm, peak area); RT=4.18 min.

TPI 2509-33 (R)-1-((S)-2-imino-1-((R)-1-((S)-2-(((R)-2-imino-5-isopropylimidazolidin-1-yl)methyl)pyrrolidin-1-yl)-3-phenylpropan-2-yl)-3-(4-methylpentyl)imidazolidin-4-yl)ethanol (33)

Using General Scheme for the synthesis of bis-cyclic guanidines compound 2509-33 was synthesized using the following reagents: Boc-D-Valine-OH ($R^1$), Boc-D-Phenylalnine-OH ($R^2$), Boc-D-Threonine(Bzl)-OH ($R^3$), 4-Methylvaleric acid ($R^4$). The final crude product was purified using HPLC as described above, with a gradient of (B) 2, 0/2, 2/2, 6/15, 30/25, 35/30. 1H NMR (400 MHz, CHLOROFORM-d) d ppm 9.90 (br. s., 1H) 9.00 (br. s., 1H) 8.59 (br. s., 2H) 7.29 (br. s., 2H) 7.21 (br. s., 2H) 4.59 (br. s., 2H) 4.27 (br. s., 2H) 3.89 (br. s., 1H) 3.79 (br. s., 1H) 3.66 (br. s., 1H) 3.54 (br. s., 1H) 3.34-3.51 (m, 4H) 3.21 (d, J=13.94 Hz, 1H) 3.13 (br. s., 1H) 2.86-3.06 (m, 2H) 2.77 (br. s., 2H) 2.36-2.63 (m, 2H) 2.07 (br. s., 1H) 1.86 (br. s., 1H) 1.72 (br. s., 2H) 1.39-1.60 (m, 2H) 1.30 (br. s., 1H) 1.04-1.22 (m, 3H) 0.97 (br. s., 2H) 0.91 (br. s., 3H) 0.84 (br. s., 7H); m/z calcd C31H53N7O [M+H]+ 540.43, found (MS ESI) 540.4. Purity LCMS: 96.78% (TIC), 99% (214 nm, peak area); RT=3.63 min.

TPI 2509-34 (R)-3-(adamantan-1-ylmethyl)-1-((R)-1-((S)-2-(((R)-2-imino-5-isopropylimidazolidin-1-yl)methyl)pyrrolidin-1-yl)-3-phenylpropan-2-yl)-4-propylimidazolidin-2-imine (34)

Using General Scheme for the synthesis of bis-cyclic guanidines compound 2509-34 was synthesized using the following reagents: Boc-D-Valine-OH ($R^1$), Boc-D-Phenylalnine-OH ($R^2$), Boc-D-Norvaline-OH ($R^3$), 1-Adamantancecarboxylic acid ($R^4$). The final crude product was purified using HPLC as described above, with a gradient of (B) 2, 0/2, 2/2, 6/20, 30/30. 1H NMR (400 MHz, CHLOROFORM-d) d ppm 10.47 (br. s., 1H) 9.33 (br. s., 1H) 8.63 (br. s., 2H) 7.37 (br. s., 2H) 7.18 (br. s., 2H) 4.68 (br. s., 1H) 4.01 (br. s., 2H) 3.76 (br. s., 1H) 3.68 (br. s., 1H) 3.58 (br. s., 2H) 3.30-3.48 (m, 2H) 3.16-3.30 (m, 3H) 3.07 (d, J=14.06 Hz, 1H) 2.98 (br. s., 2H) 2.74 (t, J=11.55 Hz, 1H) 2.45-2.67 (m, 3H) 2.08 (br. s., 1H) 1.87 (br. s., 4H) 1.71-1.82 (m, 2H) 1.63 (d, J=11.49 Hz, 4H) 1.53 (br. s., 3H) 1.27-1.41 (m, 3H) 1.24 (br. s., 1H) 1.05-1.21 (m, 3H) 0.90 (br. s., 5H) 0.82 (br. s., 3H); m/z calcd C37H59N7 [M+H]+ 602.48, found (MS ESI) 602.45. Purity LCMS: 96.95% (TIC), 99% (214 nm, peak area); RT=4.36 min.

TPI 2509-35 (R)-3-((4-(tert-butyl)cyclohexyl)methyl)-1-((R)-1-((S)-2-(((R)-2-imino-5-isopropylimidazolidin-1-yl)methyl)pyrrolidin-1-yl)-3-phenylpropan-2-yl)-4-propylimidazolidin-2-imine (35)

Using General Scheme for the synthesis of bis-cyclic guanidines compound 2509-35 was synthesized using the following reagents: Boc-D-Valine-OH ($R^1$), Boc-D-Phenylalnine-OH ($R^2$), Boc-D-Norvaline-OH ($R^3$), 4-tert-butyl-cyclohexancecarboxylic acid ($R^4$). The final crude product was purified using HPLC as described above, with a gradient of (B) 2, 0/2, 2/2, 6/20, 30/28. 1H NMR (400 MHz, CHLOROFORM-d) d ppm 8.64 (br. s., 2H) 7.33 (br. s., 2H) 7.20 (br. s., 2H) 4.65 (br. s., 1H) 3.75 (br. s., 2H) 3.57 (br. s., 4H) 3.30-3.49 (m, 3H) 3.17-3.30 (m, 2H) 3.12 (br. s., 1H) 3.04 (d, J=14.06 Hz, 1H) 2.96 (br. s., 1H) 2.88 (d, J=15.53 Hz, 1H) 2.69-2.82 (m, 1H) 2.61 (d, J=10.39 Hz, 2H) 2.09 (br. s., 1H) 1.90 (br. s., 1H) 1.79 (br. s., 2H) 1.65 (br. s., 1H) 1.43-1.59 (m, 2H) 1.36 (d, J=12.10 Hz, 3H) 1.23 (br. s., 3H) 1.07 (d, J=12.72 Hz, 2H) 0.86-1.00 (m, 8H) 0.82 (br. s., 11H); m/z calcd C37H63N7 [M+H]+ 606.51, found (MS ESI) 606.5. Purity LCMS: 97.57% (TIC), 99% (214 nm, peak area); RT=4.57 min.

TPI 2509-36 (R)-1-((R)-1-((S)-2-(((R)-2-imino-5-isopropylimidazolidin-1-yl)methyl)pyrrolidin-1-yl)-3-phenylpropan-2-yl)-3-(4-methylpentyl)-4-propylimidazolidin-2-imine (36)

Using General Scheme for the synthesis of bis-cyclic guanidines compound 2509-36 was synthesized using the following reagents: Boc-D-Valine-OH ($R^1$), Boc-D-Phenylalnine-OH ($R^2$), Boc-D-Norvaline-OH ($R^3$), 4-Methylvaleric acid ($R^4$). The final crude product was purified using HPLC as described above, with a gradient of (B) 2, 0/2, 2/2, 6/20, 30/30. 1H NMR (400 MHz, CHLOROFORM-d) d ppm 8.60 (br. s., 2H) 7.29-7.33 (m, 2H) 7.23-7.27 (m, 2H) 7.19 (br. s., 1H) 4.55 (br. s., 1H) 3.74 (br. s., 1H) 3.32-3.60 (m, 6H) 3.21 (br. s., 2H) 2.90-3.10 (m, 4H) 2.80 (d, J=10.27 Hz, 2H) 2.47-2.68 (m, 2H) 2.07 (br. s., 1H) 1.81-1.93 (m, 1H) 1.76 (br. s., 2H) 1.64 (br. s., 1H) 1.53 (br. s., 1H) 1.39-1.49 (m, 1H) 1.20 (br. s., 5H) 0.96 (br. s., 2H) 0.88 (br. s., 6H) 0.81 (br. s., 10H); m/z calcd C32H55N7 [M+H]+ 538.45, found (MS ESI) 538.4. Purity LCMS: 96.73% (TIC), 99% (214 nm, peak area); RT=4.11 min.

TPI 2509-37 (R)-3-(adamantan-1-ylmethyl)-1-((R)-1-((S)-2-(((R)-2-imino-5-isopropylimidazolidin-1-yl)methyl)pyrrolidin-1-yl)-3-phenylpropan-2-yl)-4-isopropylimidazolidin-2-imine (37)

Using General Scheme for the synthesis of bis-cyclic guanidines compound 2509-37 was synthesized using the following reagents: Boc-D-Valine-OH ($R^1$), Boc-D-Phenylalnine-OH ($R^2$), Boc-D-Valine-OH ($R^3$), 1-Adamantancecarboxylic acid ($R^4$). The final crude product was purified using HPLC as described above, with a gradient of (B) 2, 0/2, 2/2, 6/20, 30/30. 1H NMR (400 MHz, CHLOROFORM-d) d ppm 10.45 (br. s., 1H) 9.29 (br. s., 1H) 8.65 (br. s., 2 H) 7.36 (br. s., 2H) 7.29-7.33 (m, 2H) 7.21 (br. s., 1H) 4.63 (br. s., 1H) 4.03 (br. s., 2H) 3.75 (br. s., 2H) 3.56 (br. s., 1H) 3.46 (br. s., 1H) 3.37 (t, J=14.12 Hz, 3H) 3.27 (br. s., 1H) 3.06-3.24 (m, 2H) 2.90-3.03 (m, 2H) 2.72-2.89 (m, 1H) 2.62 (d, J=15.53 Hz, 1H) 2.55 (br. s., 1H) 2.16 (br. s., 1H) 2.07 (br. s., 1H) 1.89 (br. s., 3H) 1.78 (br. s., 2H) 1.60-1.71 (m, 3H) 1.56 (br. s., 3H) 1.37 (d, J=10.88 Hz, 3H) 1.22 (d, J=11.25 Hz, 3H) 0.86-0.99 (m, 5H) 0.82 (br. s., 3H) 0.73 (br. s., 3H); m/z calcd C37H59N7 [M+H]+ 602.48, found (MS ESI) 602.45. Purity LCMS: 95.20% (TIC), 99% (214 nm, peak area); RT=4.36 min.

TPI 2509-38 (R)-3-((4-(tert-butyl)cyclohexyl)
methyl)-1-((R)-1-((S)-2-(((R)-2-imino-5-isopropylimidazolidin-1-yl)methyl)pyrrolidin-1-yl)-3-phenylpropan-2-yl)-4-isopropylimidazolidin-2-imine (38)

Using General Scheme for the synthesis of bis-cyclic guanidines compound 2509-38 was synthesized using the following reagents: Boc-D-Valine-OH ($R^1$), Boc-D-Phenylalnine-OH ($R^2$), Boc-D-Valine-OH ($R^3$), 4-tert-butyl-cyclohexancecarboxylic acid ($R^4$). The final crude product was purified using HPLC as described above, with a gradient of (B) 2, 0/2, 2/2, 6/20, 30/30. 1H NMR (400 MHz, CHLOROFORM-d) d ppm 8.65 (br. s., 2H) 7.36 (br. s., 2H) 7.29 (br. s., 2H) 7.22 (br. s., 1H) 4.65 (br. s., 1H) 3.65-3.90 (m, 2H) 3.58 (br. s., 2H) 3.35-3.52 (m, 4H) 3.23-3.33 (m, 2H) 3.20 (br. s., 1H) 3.09 (d, J=12.84 Hz, 1H) 3.01 (br. s., 2H) 2.71-2.92 (m, 2H) 2.45-2.69 (m, 2H) 2.09 (br. s., 1H) 2.04 (br. s., 1H) 1.92 (br. s., 1H) 1.80 (br. s., 2H) 1.62-1.74 (m, 1H) 1.57 (br. s., 1H) 1.39-1.53 (m, 2H) 1.29-1.39 (m, 1H) 1.23 (d, J=11.74 Hz, 1H) 1.06-1.18 (m, 1H) 0.99 (br. s., 2H) 0.91 (br. s., 7H) 0.84 (br. s., 10H) 0.77 (br. s., 3H); m/z calcd C37H63N7 [M+H]+ 606.51, found (MS ESI) 606.5. Purity LCMS: 97.88% (TIC), 99% (214 nm, peak area); RT=4.58 min.

TPI 2509-39 (R)-1-((R)-1-((S)-2-(((R)-2-imino-5-isopropylimidazolidin-1-yl)methyl)pyrrolidin-1-yl)-3-phenylpropan-2-yl)-4-isopropyl-3-(4-methylpentyl)imidazolidin-2-imine (39)

Using General Scheme for the synthesis of bis-cyclic guanidines compound 2509-39 was synthesized using the following reagents: Boc-D-Valine-OH ($R^1$), Boc-D-Phenylalnine-OH ($R^2$), Boc-D-Valine-OH ($R^3$), 4-Methylvaleric acid ($R^4$). The final crude product was purified using HPLC as described above, with a gradient of (B) 2, 0/2, 2/2, 6/20, 30/28. 1H NMR (400 MHz, CHLOROFORM-d) d ppm 9.10 (br. s., 1H) 8.38 (br. s., 2H) 7.00-7.09 (m, 4H) 6.95 (br. s., 1H) 4.28 (br. s., 1H) 3.50 (br. s., 1H) 3.22-3.37 (m, 3H) 3.13 (d, J=11.00 Hz, 3H) 2.96 (br. s., 3H) 2.74 (d, J=14.79 Hz, 3H) 2.59 (d, J=10.27 Hz, 2H) 2.34 (d, J=12.96 Hz, 1H) 2.17-2.29 (m, 1H) 1.83 (br. s., 1H) 1.59-1.79 (m, 2H) 1.52 (br. s., 2H) 1.30 (br. s., 1H) 1.16-1.26 (m, 1H) 1.02 (br. s., 1H) 0.92 (br. s., 1H) 0.75 (br. s., 2H) 0.63 (br. s., 5H) 0.57 (br. s., 8H) 0.47 (br. s., 4H); m/z calcd C32H55N7 [M+H]+ 538.45, found (MS ESI) 538.4. Purity LCMS: 96.55% (TIC), 99% (214 nm, peak area); RT=4.11 min.

TPI 2509-40 4-((1-((R)-1-((S)-2-(((R)-5-((S)-secbutyl)-2-iminoimidazolidin-1-yl)methyl)pyrrolidin-1-yl)-3-phenylpropan-2-yl)-3-((4-(tert-butyl)cyclohexyl)methyl)-2-iminoimidazolidin-4-yl)methyl)
phenol (40)

Using General Scheme for the synthesis of bis-cyclic guanidines compound 2509-40 was synthesized using the following reagents: Boc-D-Isoleucine-OH ($R^1$), Boc-D-Phenylalnine-OH ($R^2$), Boc-D-Tyrosine(2-Br—Z)—OH ($R^3$), 4-tert-butyl-cyclohexancecarboxylic acid ($R^4$). The final crude product was purified using HPLC as described above, with a gradient of (B) 2, 0/2, 2/2, 6/20, 30/28. 1H NMR (400 MHz, CHLOROFORM-d) d ppm 9.26 (br. s., 1H) 8.66 (br. s., 2H) 7.22 (br. s., 2H) 6.88 (br. s., 3H) 4.38 (br. s., 1H) 3.94 (br. s., 2H) 3.85 (br. s., 2H) 3.64 (br. s., 2H) 3.48-3.58 (m, 2H) 3.45 (br. s., 1H) 3.38 (br. s., 1H) 3.23 (br. s., 1H) 2.98-3.18 (m, 3H) 2.92 (br. s., 1H) 2.69 (br. s., 2H) 2.53 (br. s., 2H) 2.44 (br. s., 1H) 1.95 (br. s., 1H) 1.82 (br. s., 3H) 1.52 (br. s., 2H) 1.39 (br. s., 1H) 1.33 (br. s., 1H) 1.22 (d, J=13.45 Hz, 3H) 0.95 (br. s., 4H) 0.69-0.90 (m, 10H); m/z calcd C42H65N7O [M+H]+ 684.54, found (MS ESI) 684.5. Purity LCMS: 98.23% (TIC), 99% (214 nm, peak area); RT=4.47 min.

Example 3. Biological Evaluation

The compounds were evaluated using a whole cell assay. This cell assay utilizes HEK293 cells which are transfected with the various melanocortin receptor subtypes and cAMP, a signal important to melanocortin receptor activation, is indirectly measured using a beta-galactosidase reporter gene system (Chen, W. et al (1995) *Analytical Biochemistry*, 226:349-354).

cAMP Based Functional Bioassay

Compounds were dissolved in DMSO at a stock concentration of $10^{-2}$ M and stored at −20° C. until assayed. HEK-293 cells stably expressing the selected melanocortin receptors were transiently transfected with 4 μg of CRE/β-galactosidase reporter gene. Briefly, 5000-15000 post transfection cells were plated into collagen treated 96-well plates (Nunc) and incubated overnight. Forty-eight hours post-transfection, the cells were stimulated with 50 μL of compound ($10^{-6}$-$10^{-12}$M or $10^{-4}$-$10^{-10}$ M for single compounds in dose-response, depending on compound potency, or ca. 50 μg/mL for screening) or forskolin ($10^{-4}$ M) control in assay medium (DMEM containing 0.1 mg/mL BSA and 0.1 mM isobutylmethylxanthine) for 6 h. For screening, each plate was visually inspected under a microscope to determine if cells were healthy or had been killed during the compound stimulation process. The assay media was aspirated, and 50 μL of lysis buffer (250 mM Tris-HCl pH=8.0 and 0.1% Triton X-100) was added. The plates were stored at −80° C. overnight. The plates containing the cell lysates were thawed the following day. Aliquots of 10 μL were taken from each well and transferred to another 96-well plate for relative protein determination. To the cell lysate plates, 40 μL of phosphate-buffered saline with 0.5% BSA was added to each well. Subsequently, 150 μL of substrate buffer (60 mM sodium phosphate, 1 mM $MgCl_2$, 10 mM KCl, 5 mM β-mercaptoethanol, 2 mg/mL ONPG) was added to each well and the plates were incubated at 37° C. The sample absorbance, OD405, was measured using a 96-well plate reader (Molecular Devices). The relative protein was determined by adding 200 μL of 1:5 dilution BioRad G250 protein dye:water to the 10 µL of cell lysate sample taken previously, and the OD595 was measured on a 96-well plate reader (Molecular Devices). Data points were normalized to forskolin and the relative protein content were used as positive controls. The $EC_{50}$ values represent the mean of three or more independent experiments. The $EC_{50}$ estimates, and their associated standard errors of the mean, were determined by fitting the data to a nonlinear least-squares analysis using the PRISM program (v4.0, GraphPad Inc.). This assay protocol was adopted from a similar collaborative study reported in the literature (Haslach, E., et al, (2014) *J. Med. Chem.*, 57:4615-4628).

Results

Each of the exemplary formula I compounds from Table 2a were tested at the mouse melanocortin-1, melanocortin-3, melanocortin-4, and melanocortin-5 receptors for agonist, or ability to activate the given receptor subtype, at concentrations ranging from 0.1 nM to 100,000 nM. Table 2b tabulates the results observed for receptor activation comparing the melanocortin-1 receptor to the melanocortin-3 receptor. Table 2c tabulates the results observed for receptor activation comparing the melanocortin-4 receptor to the melanocortin-5 receptor. The results are tabulated in the form of $EC_{50}$ values. In the case where the particular receptor was not activated to full activity at 100,000 nM, then the relative activity was reported.

Several potent melanocortin-3 receptor compounds were discovered. With respect to the initial goal, some exciting results included several compounds such as TPI 2509-14 and TPI 2509-32 which produced nanomolar $EC_{50}$ values at the melanocortin-3 receptor and little to no activation (>20% maximal activation at 100,000 nM) at the melanocortin-4 receptor (illustrated in FIG. 4).

Figure 3A:
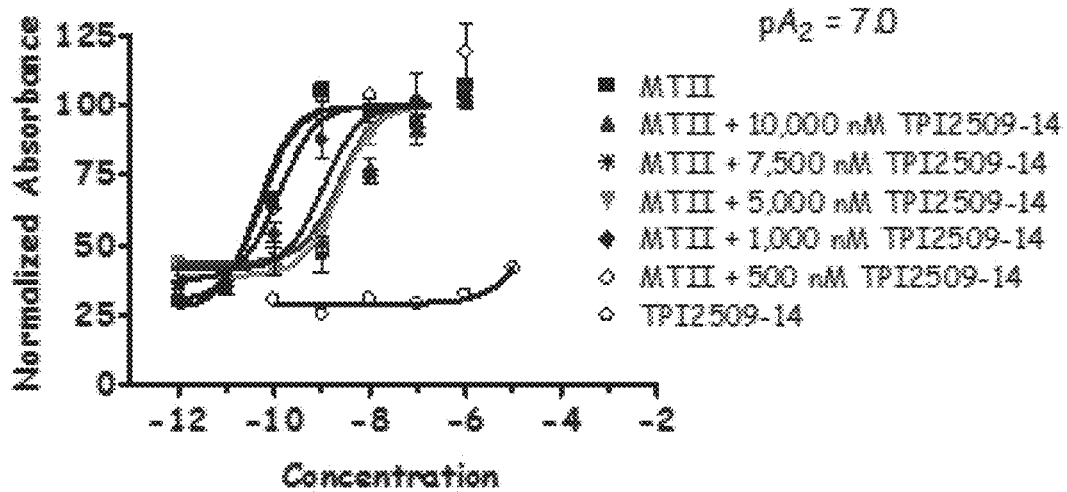
FIG. 3A illustrates a dose-response curve for mMC3R/mMC4R agonist activity and for observed antagonist activity at the mouse MC4R for compound TPI2509-14. Concentration is log [compound (M)].
Figure 3B:
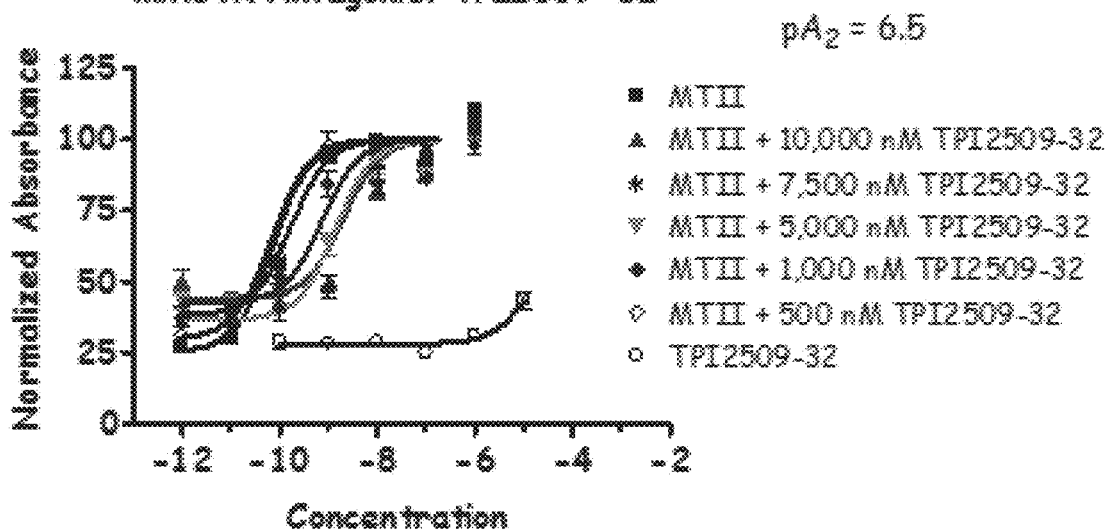
FIG. 3B illustrates a dose-response curve for observed antagonist activity at the mouse MC4R for compound TPI2509-32. Concentration is log [compound (M)]
Figure 4A:
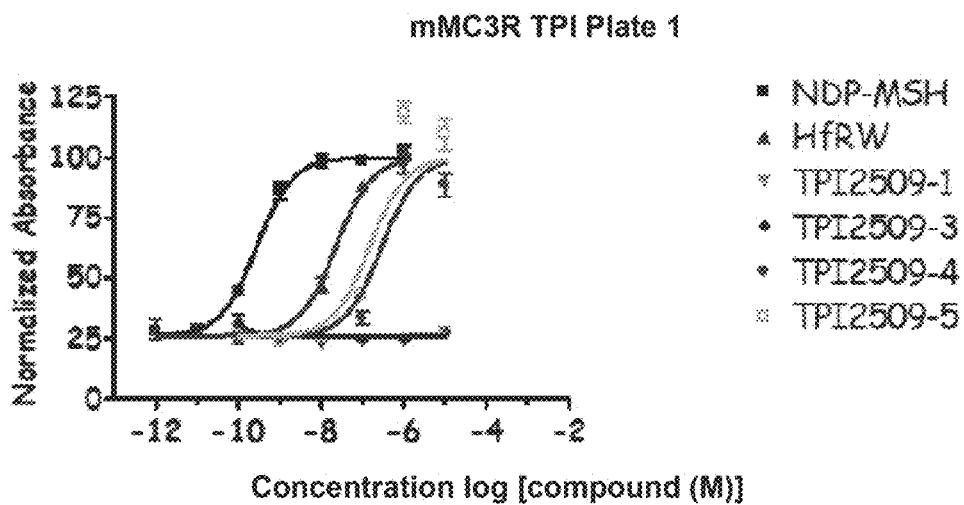
FIG. 4A shows a dose-response curve at the mouse MC3R for positive controls NDP-MSH and HfRW, and TPI2509 compounds 1, 3, 4, 5.
Figure 4B:
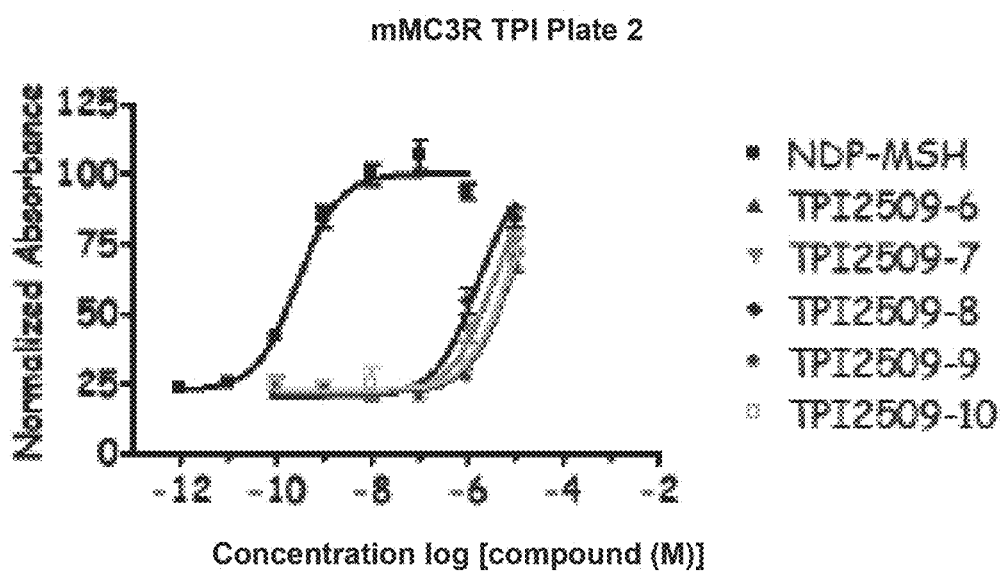
FIG. 4B shows a dose-response curve at the mouse MC3R for positive control NDP-MSH and TPI2509 compounds 6-10.
Figure 4C:
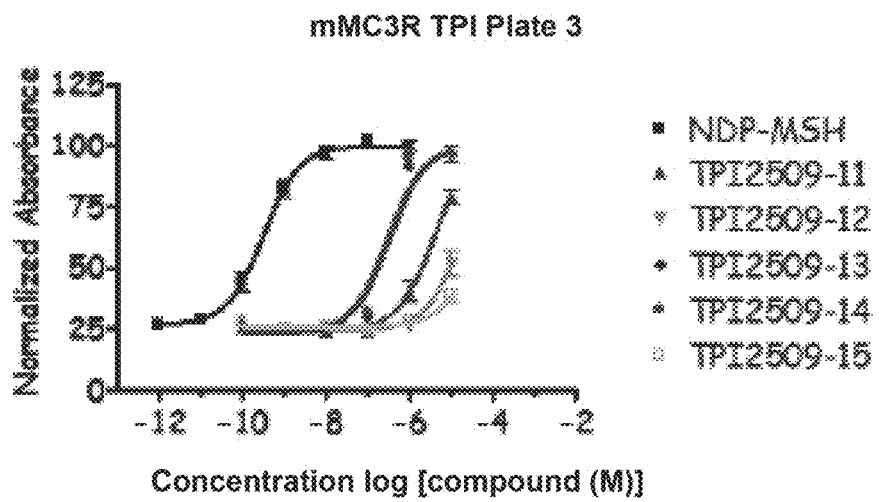
FIG. 4C shows a dose-response curve at the mouse MC3R for positive control NDP-MSH and TPI2509 compounds 11-15.
Figure 4D:
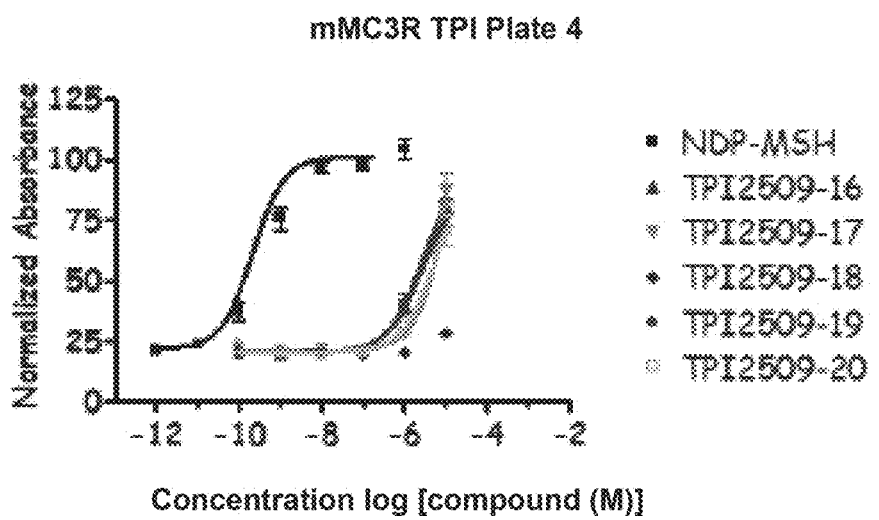
FIG. 4D shows a dose-response curve at the mouse MC3R for positive control NDP-MSH and TPI2509 compounds 16-20.
Figure 4E:
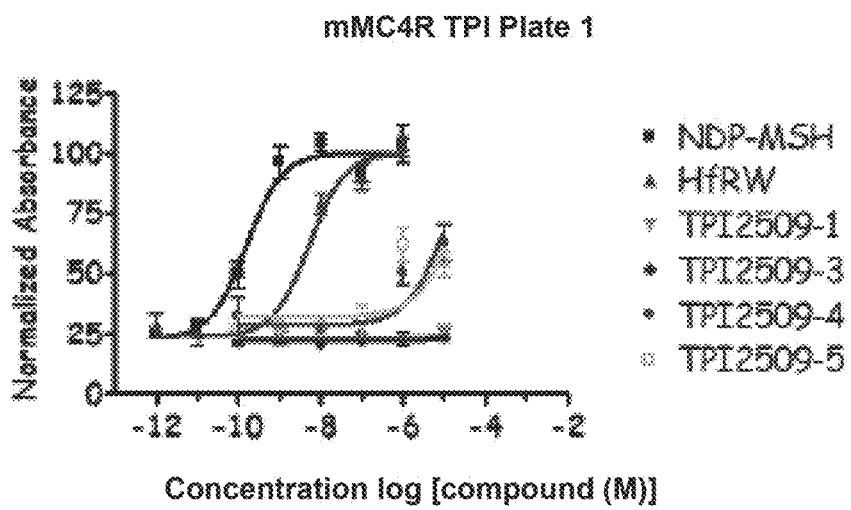
FIG. 4E shows a dose-response curve at the mouse MC4R for positive controls (NDP-MSH and HfRW) and TPI2509 compounds 1, 3, 4, 5.
Figure 4F:
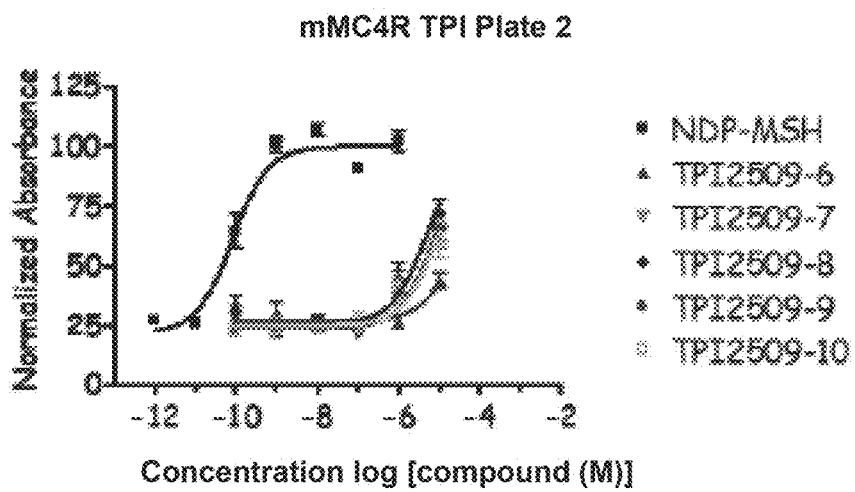
FIG. 4F shows a dose-response curve at the mouse MC4R for positive control NDP-MSH and TPI2509 compounds 6-10.
Figure 4G:
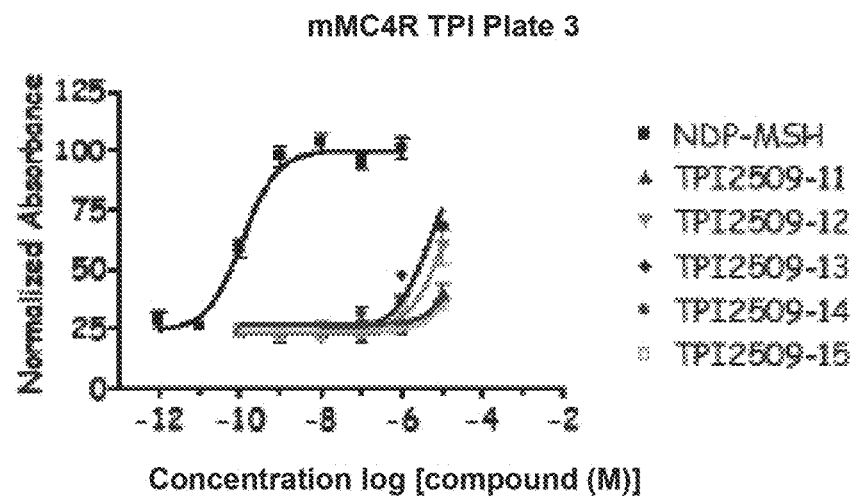
FIG. 4G shows a dose-response curve at the mouse MC4R for positive control NDP-MSH and and TPI2509 compounds 11-15.
Figure 4H:
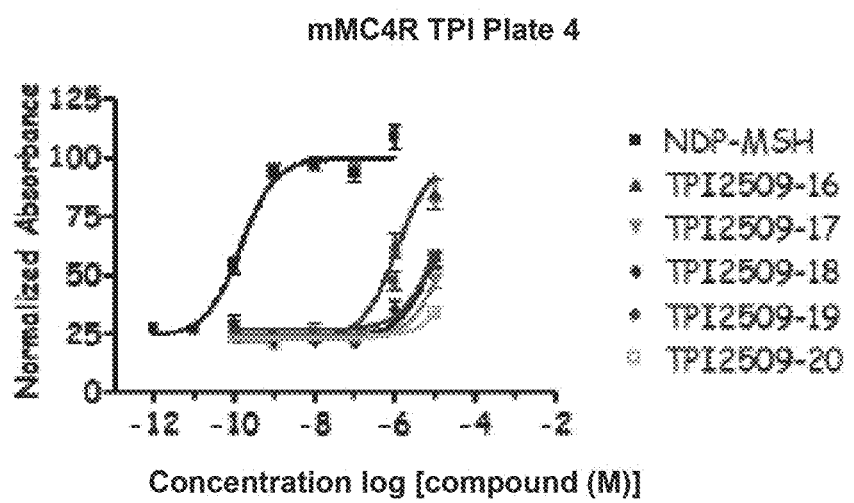
FIG. 4H shows a dose-response curve at the mouse MC4R for positive control NDP-MSH and TPI2509 compounds 16-20.
Figure 5A:
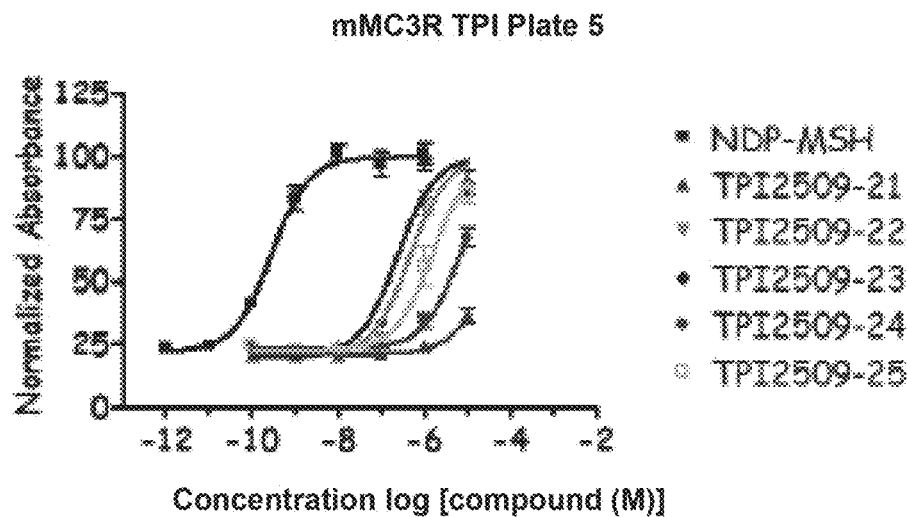
FIG. 5A shows a dose-response curve at the mouse MC3R for positive control NDP-MSH and TPI2509 compounds 21-25.
Figure 5B:
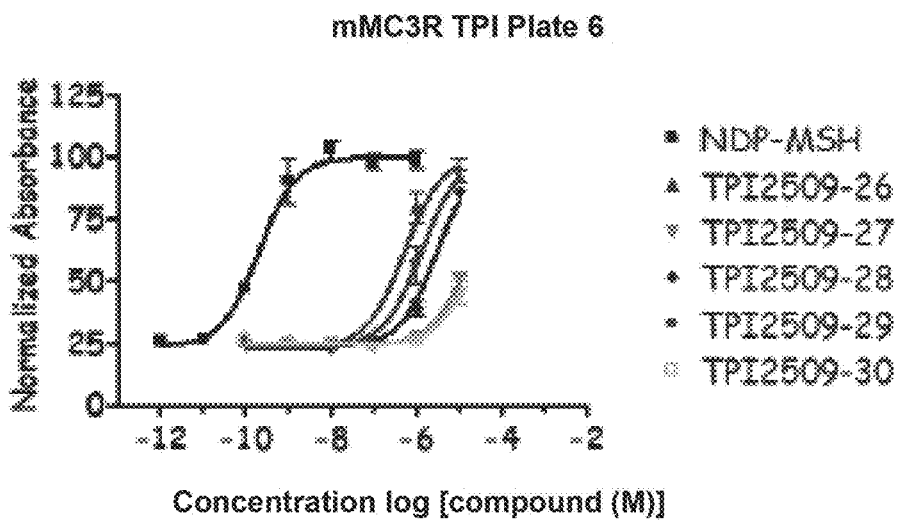
FIG. 5B shows a dose-response curve at the mouse MC3R for positive control NDP-MSH and TPI2509 compounds 26-30.
Figure 5C:
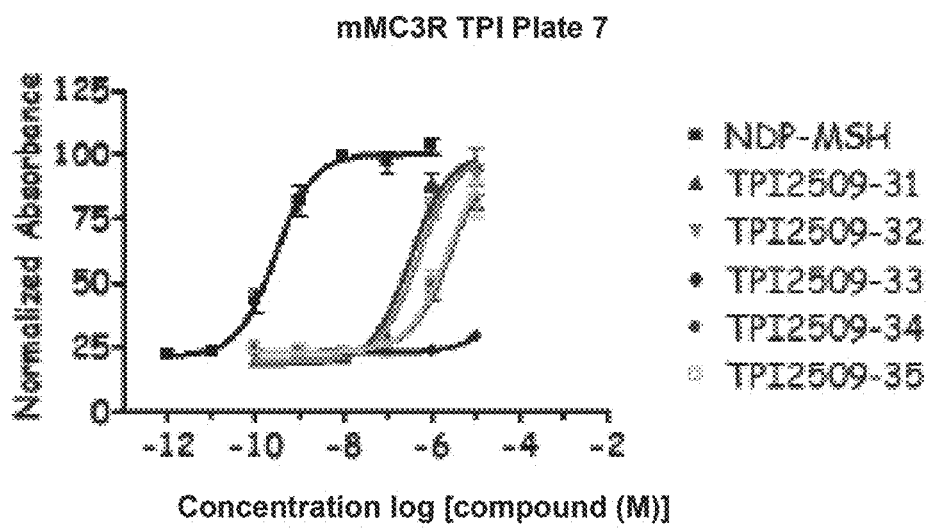
FIG. 5C shows a dose-response curve at the mouse MC3R for positive control NDP-MSH and TPI2509 compounds 31-35.
Figure 5D:
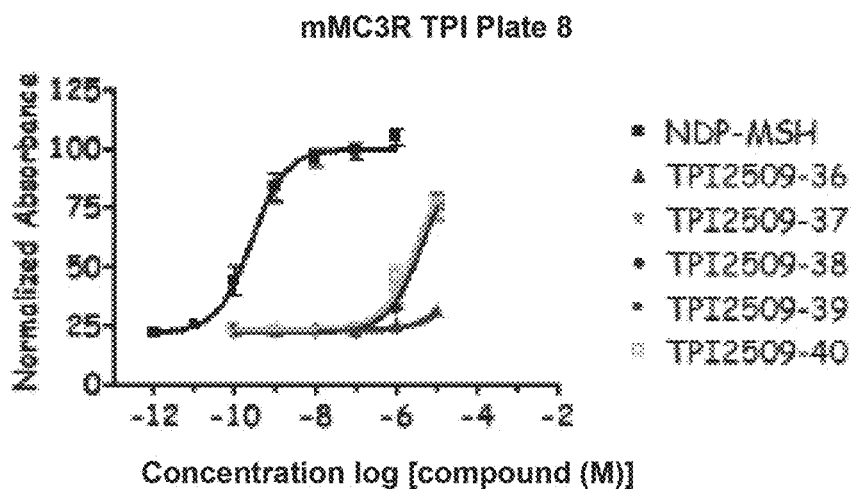
FIG. 5D shows a dose-response curve at the mouse MC3R for positive control NDP-MSH and TPI2509 compounds 36-40.
Figure 5E:
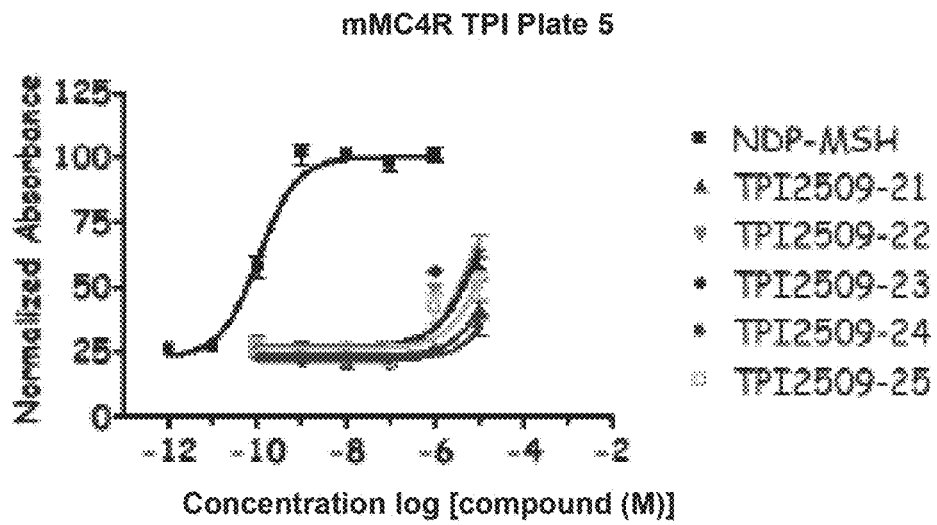
FIG. 5E shows a dose-response curve at the mouse MC4R positive control NDP-MSH and TPI2509 compounds 21-25.
Figure 5F:
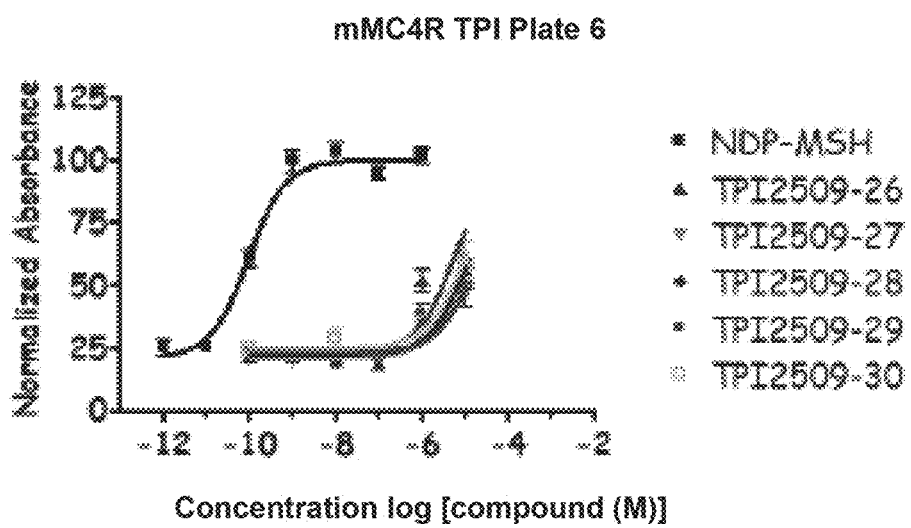
FIG. 5F shows a dose-response curve at the mouse MC4R for positive control NDP-MSH and TPI2509 compounds 26-30.
Figure 5G:
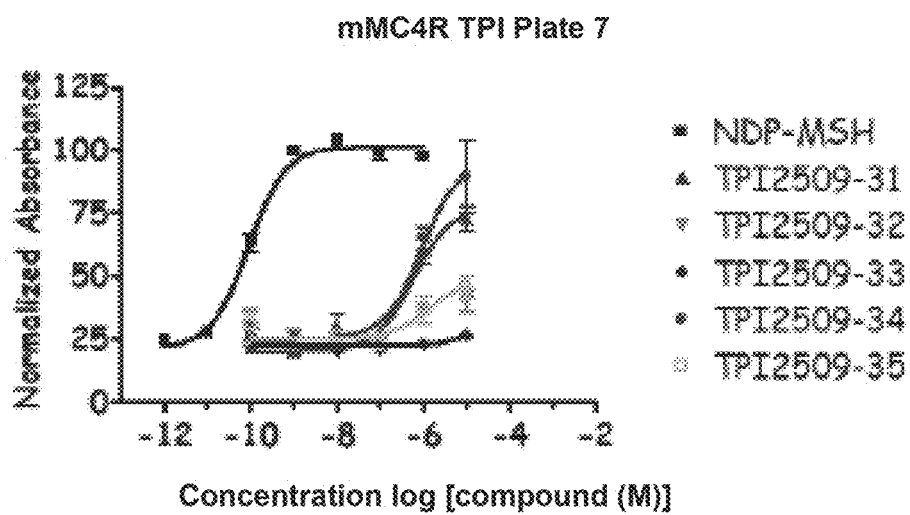
FIG. 5G shows a dose-response curve at the mouse MC4R for positive control NDP-MSH and TPI2509 compounds 31-35.
Figure 5H:
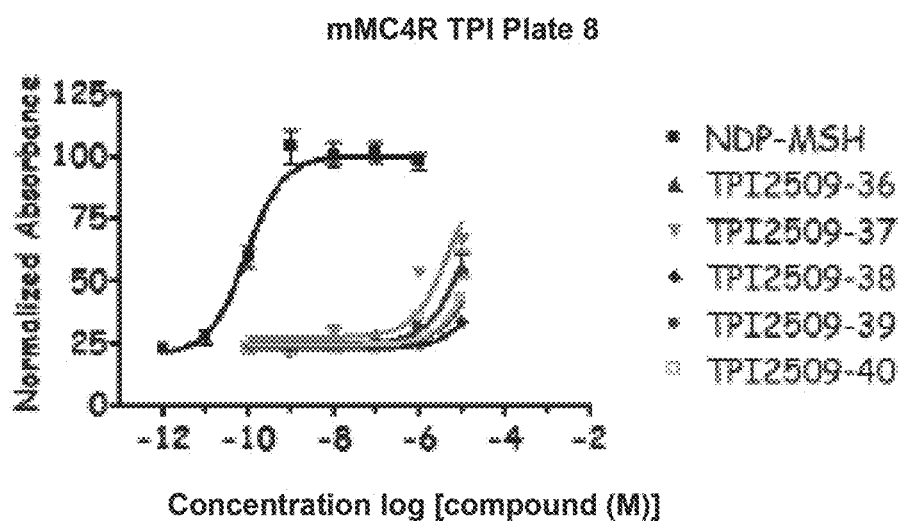
FIG. 5H shows a dose-response curve at the mouse MC4R for positive control NDP-MSH and TPI2509 compounds 36-40.
Figure 6A:
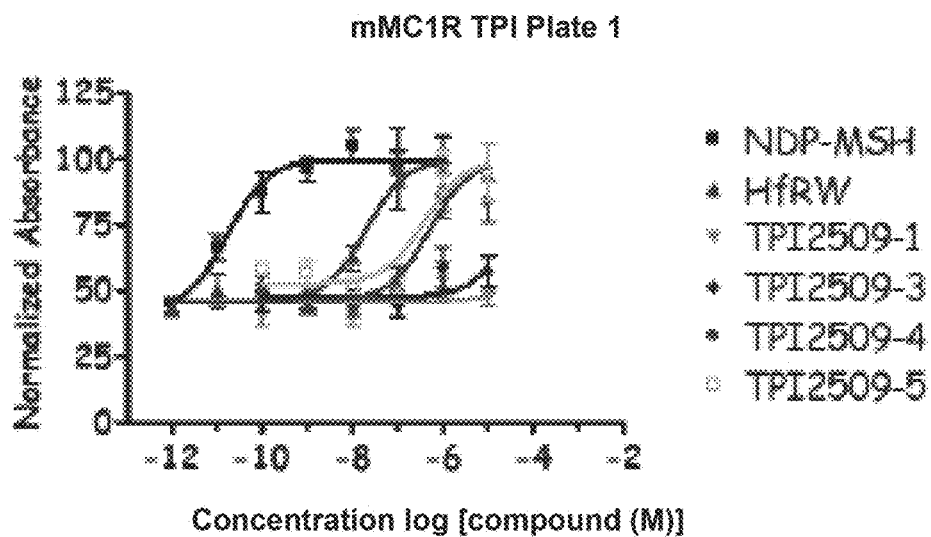
FIG. 6A shows a dose-response curve at the mouse MC1R for positive controls (NDP-MSH and HfRW) and TPI2509 compounds 1, 3, 4, 5.
Figure 6B:
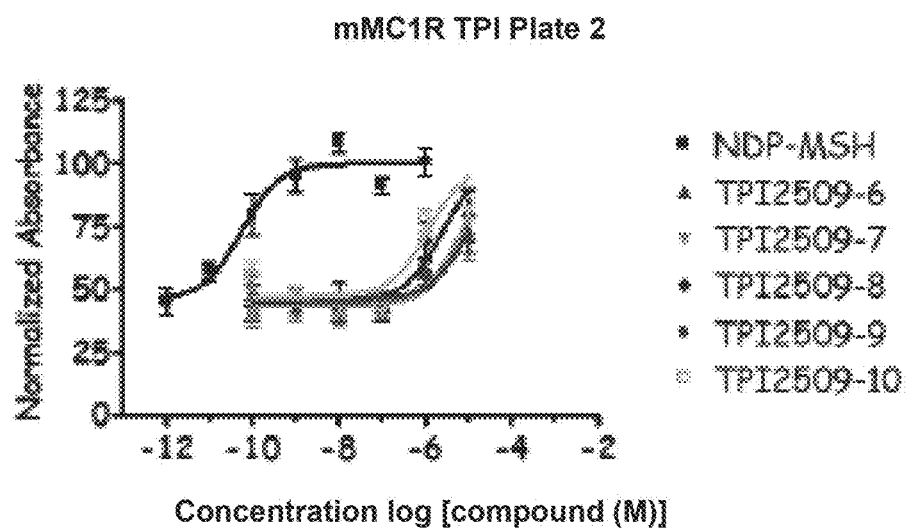
FIG. 6B shows a dose-response curve at the mouse MC1R for positive control NDP-MSH and TPI2509 compounds 6-10.
Figure 6C:
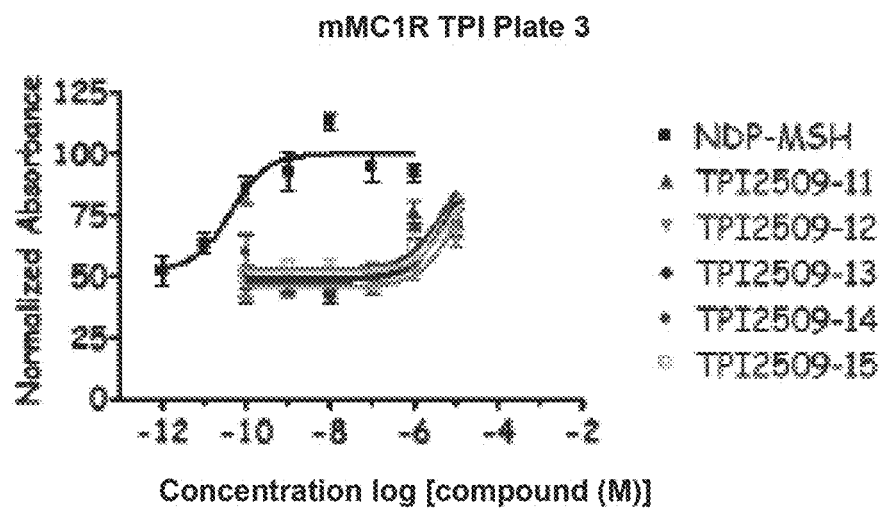
FIG. 6C shows a dose-response curve at the mouse MC1R for positive control NDP-MSH and TPI2509 compounds 11-15.
Figure 6D:
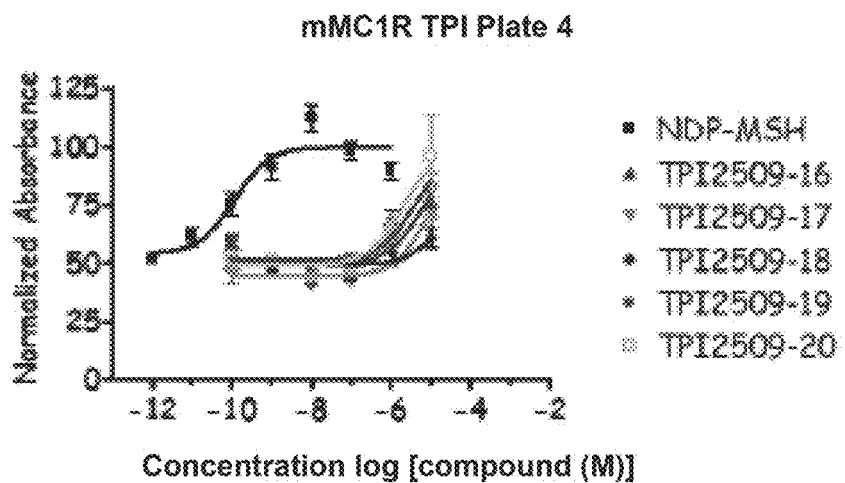
FIG. 6D shows a dose-response curve at the mouse MC1R for positive control NDP-MSH and TPI2509 compounds 16-20.
Figure 6E:
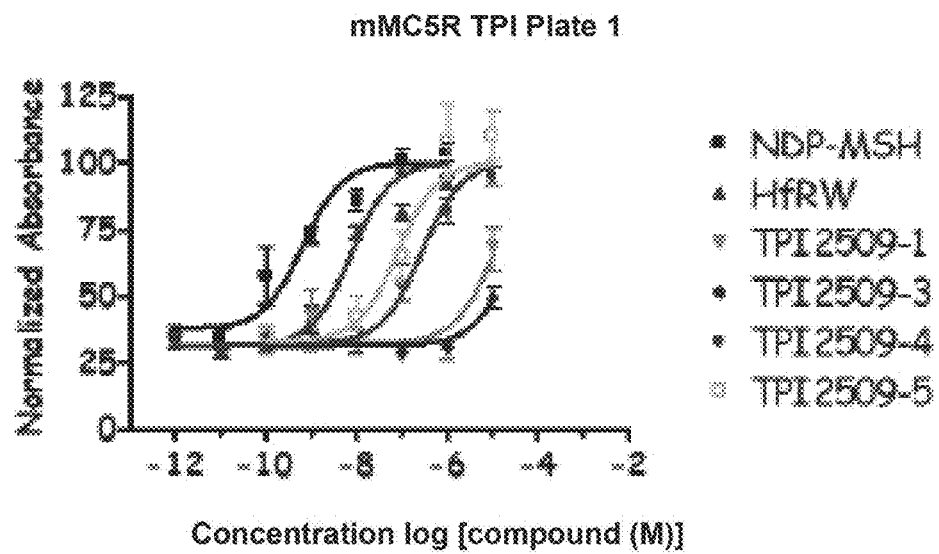
FIG. 6E shows a dose-response curve at the mouse MC5R for positive controls (NDP-MSH and HfRW) and TPI2509 compounds 1, 3, 4, 5.
Figure 6F:
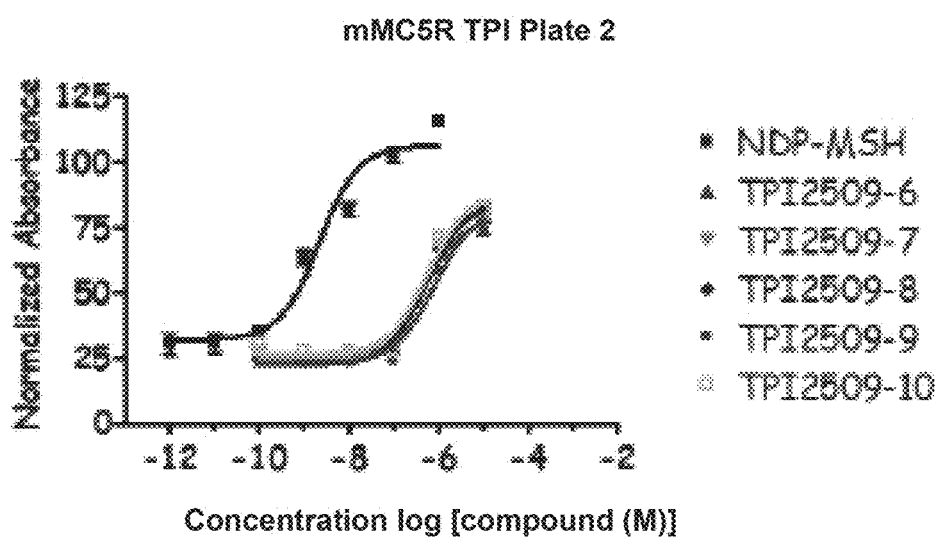
FIG. 6F shows a dose-response curve at the mouse MC5R for positive control NDP-MSH and TPI2509 compounds 6-10.
Figure 6G:
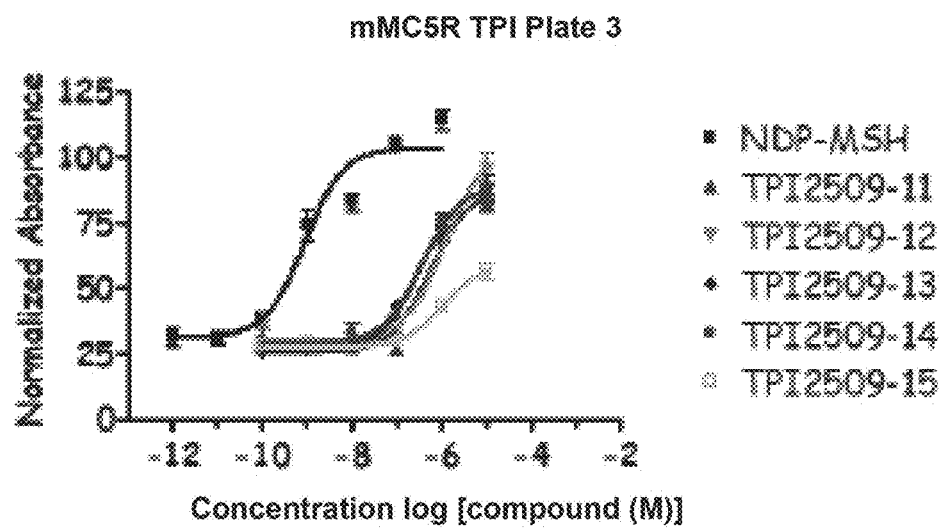
FIG. 6G shows a dose-response curve at the mouse MC5R for positive control NDP-MSH and TPI2509 compounds 11-15.
Figure 6H:
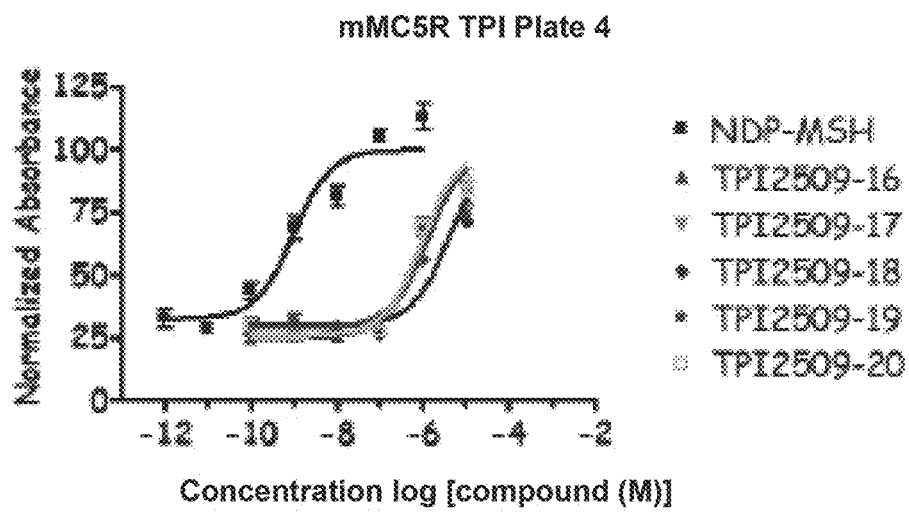
FIG. 6H shows a dose-response curve at the mouse MC5R for positive control NDP-MSH and TPI2509 compounds 16-20.
Figure 7A:
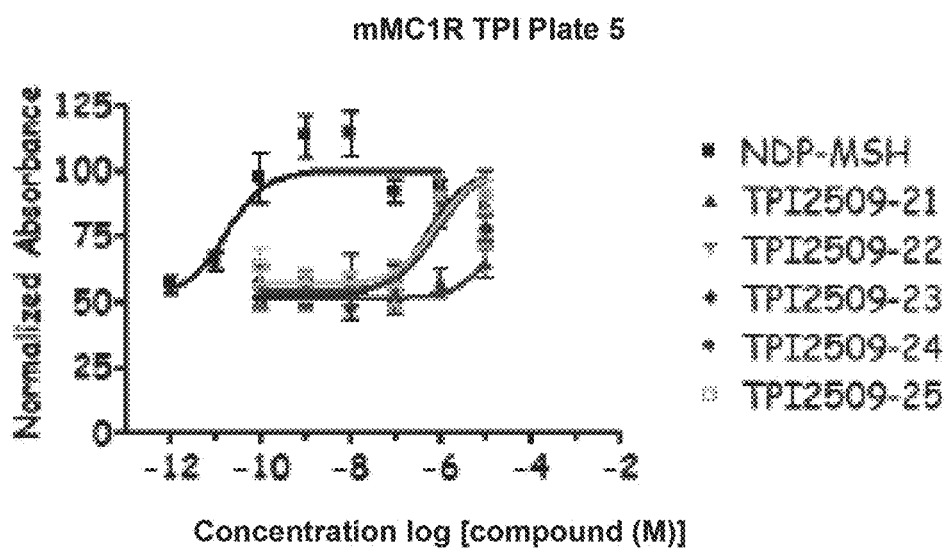
FIG. 7A shows a dose-response curve at the mouse MC1R for positive control NDP-MSH and TPI2509 compounds 21-25.
Figure 7B:
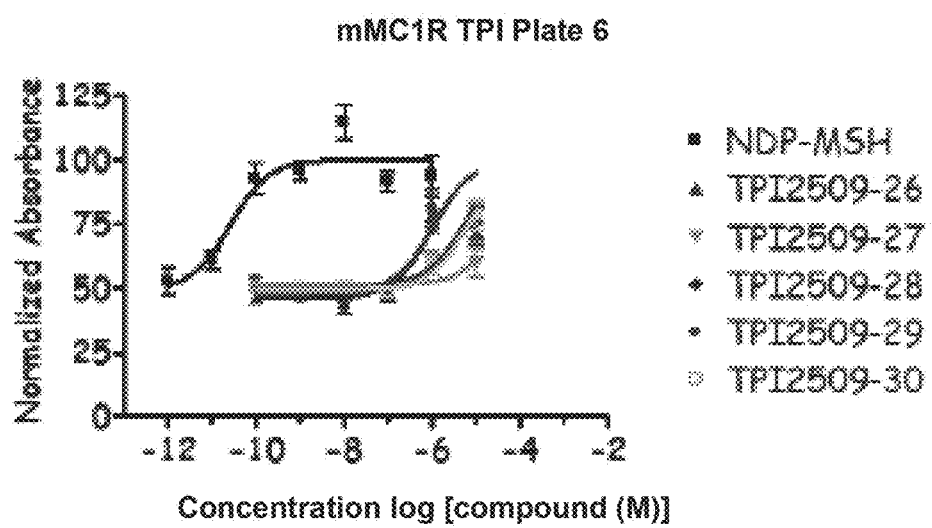
FIG. 7B shows a dose-response curve at the mouse MC1R for positive control NDP-MSH and TPI2509 compounds 26-30.
Figure 7C:
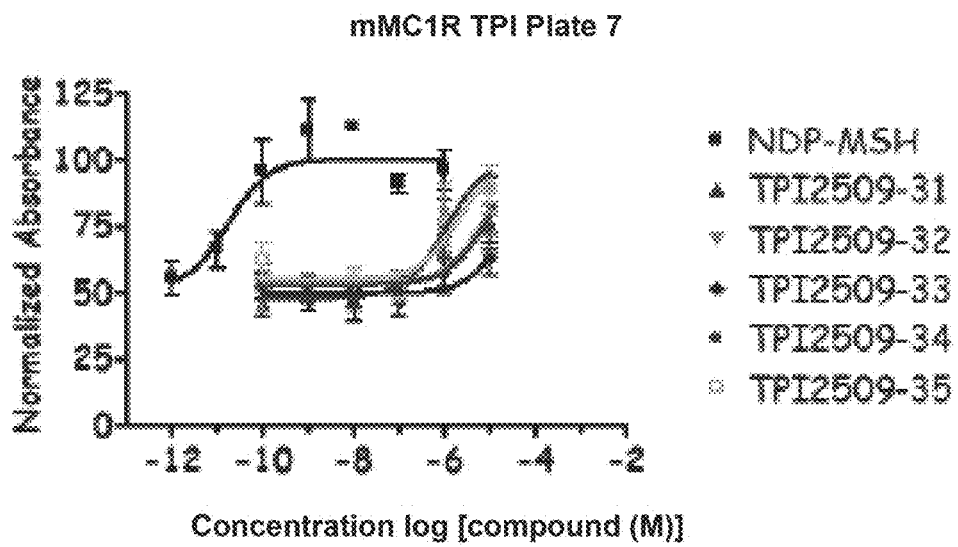
FIG. 7C shows a dose-response curve at the mouse MC1R for positive control NDP-MSH and TPI2509 compounds 31-35.
Figure 7D:
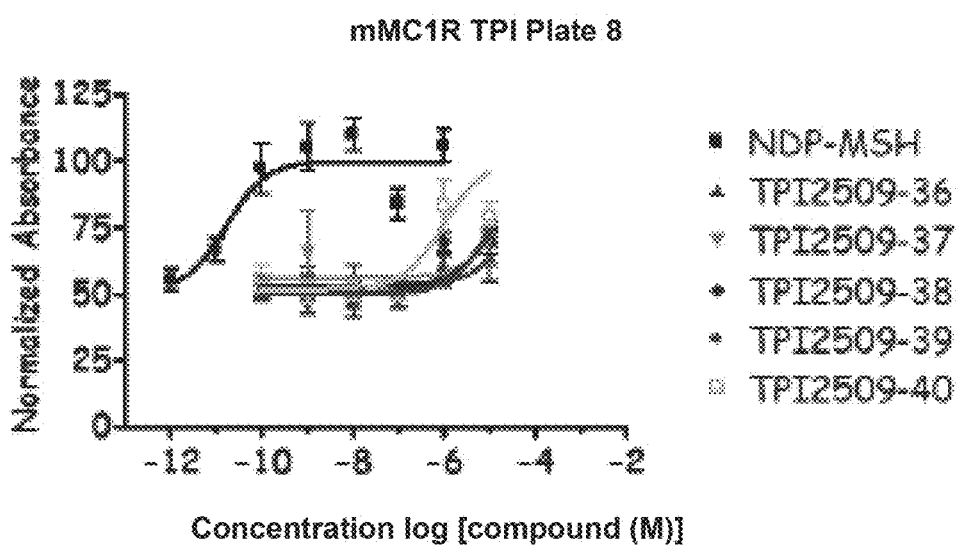
FIG. 7D shows a dose-response curve at the mouse MC1R for positive control NDP-MSH and TPI2509 compounds 36-40.
Figure 7E:
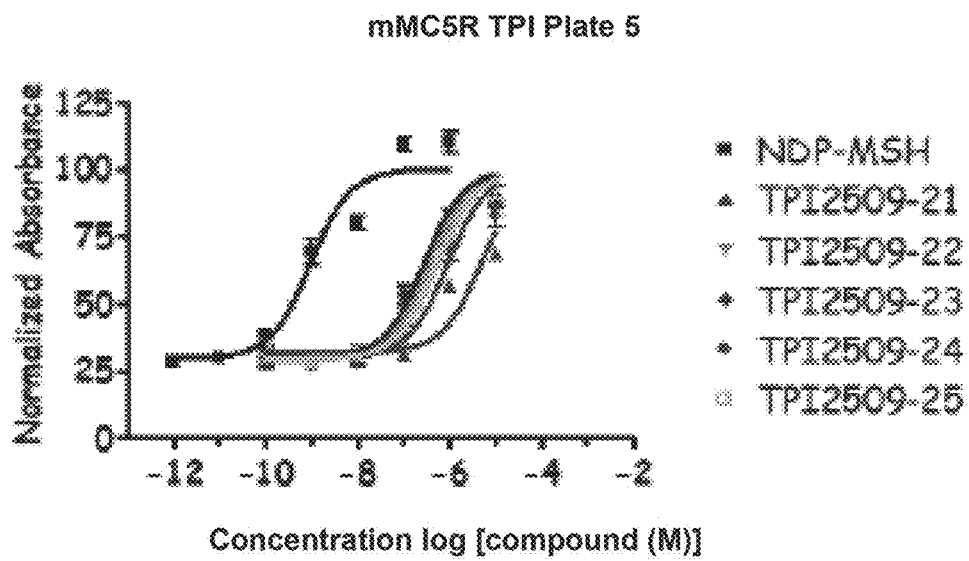
FIG. 7E shows a dose-response curve at the mouse MC5R for positive control NDP-MSH and TPI2509 compounds 21-25.
Figure 7F:
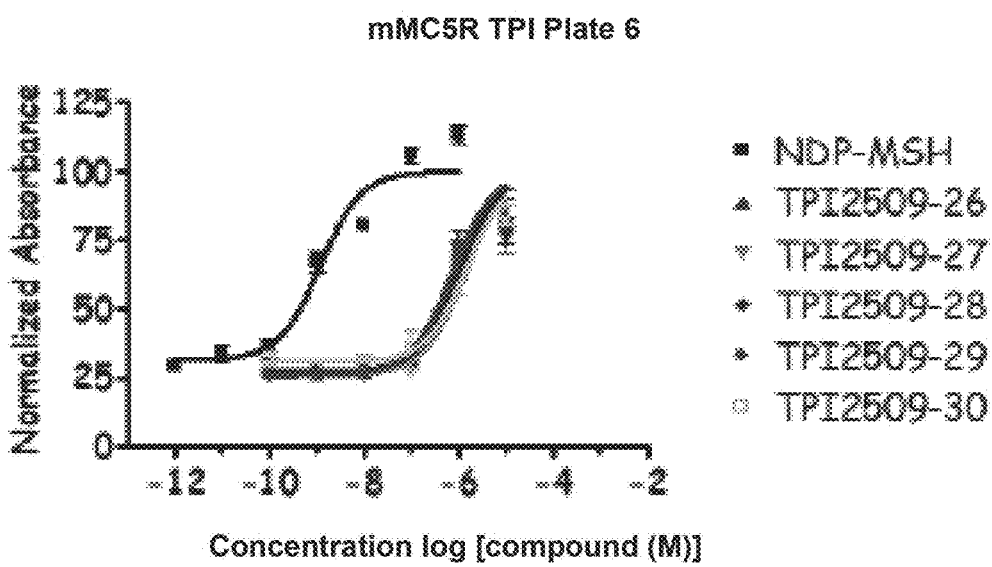
FIG. 7F shows a dose-response curve at the mouse MC5R for positive control NDP-MSH and TPI2509 compounds 26-30.
Figure 7G:
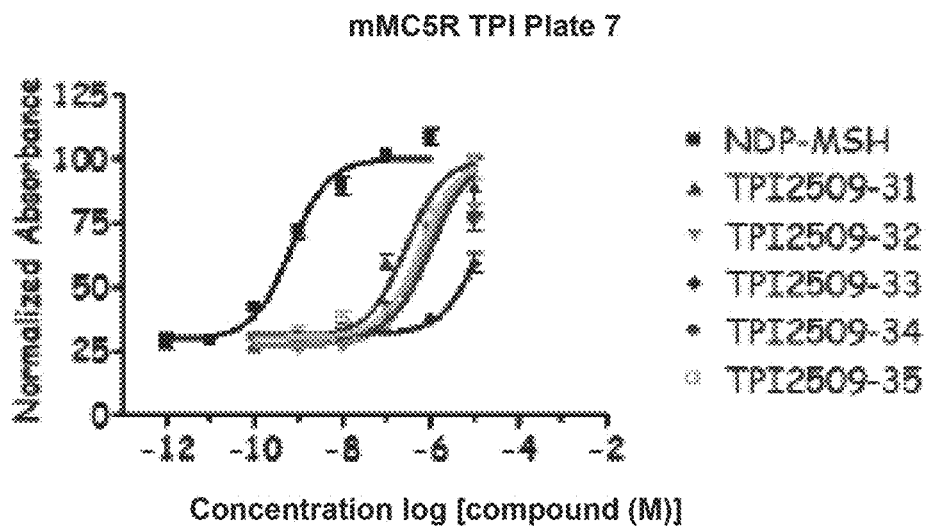
FIG. 7G shows a dose-response curve at the mouse MC5R for positive control NDP-MSH and TPI2509 compounds 31-35.
Figure 7H:
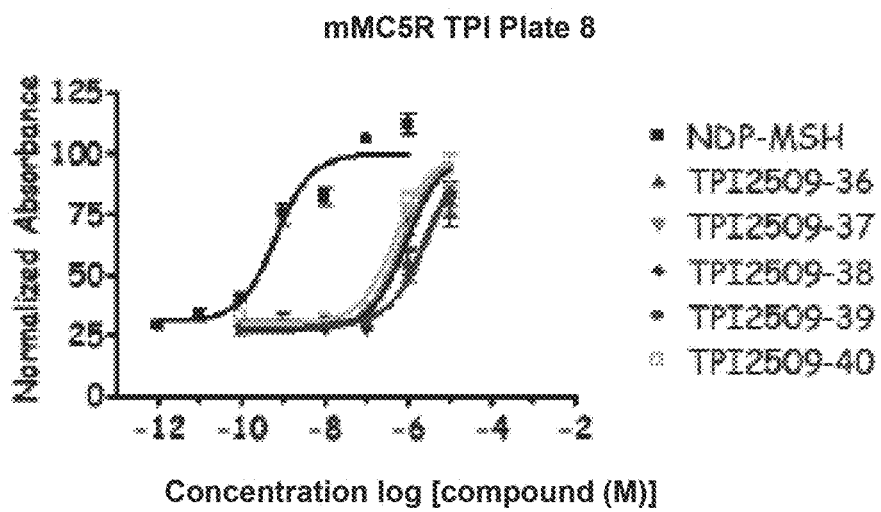
FIG. 7H shows a dose-response curve at the mouse MC5R positive control NDP-MSH and TPI2509 compounds 36-40.

These compounds were selected for further study at the melanocortin-4 receptor to study their potential effects in their ability to block the activity of a known receptor agonist, in the form of a Schild analysis (Schild, H. O., (1947) *British Journal of Pharmacology*, 2:189-206). These studies indicated TPI 2509-14 and TPI 2509-32 displayed antagonist activity with $pA_2$ values of 7.0±0.7 and 6.5±0.5, respectively. The reported values are on a log scale. In order to put them into perspective, their approximate binding disassociation constants, $K_i$ values, can be calculated through the following relationship $pA_2=-\text{Log}_{10}(K_i)$. Therefore, the $K_i$ values for TPI 2509-14 and TPI 2509-32 are 100 nM and 320 nM, correspondingly. The Schild plots are illustrated in FIGS. 3A and 3B.

TABLE 2a

Exemplary formula I compound substituents

| Compound/TPI # | $R_1$ | $R_2$ | $R_3$ | $R_4$ |
| --- | --- | --- | --- | --- |
| 2509-4 | R-isobutyl | R-cyclohexyl | (S,R)-1-hydroxyethyl | adamantan-1-yl-methy; |
| 2509-5 | R-isobutyl | R-cyclohexyl | (S,R)-1-hydroxyethyl | 4-tbutyl-cyclohexyl-methyl |
| 2509-6 | R-isobutyl | R-cyclohexyl | (S,R)-1-hydroxyethyl | 4-methylpentyl |
| 2509-7 | R-isobutyl | R-cyclohexyl | R-propyl | adamantan-1-yl-methyl |
| 2509-8 | R-isobutyl | R-cyclohexyl | R-propyl | 4-tbutyl-cyclohexyl-methyl |
| 2509-9 | R-isobutyl | R-cyclohexyl | R-propyl | 4-methylpentyl |
| 2509-10 | R-isobutyl | R-cyclohexyl | R-isopropyl | adamantan-1-yl-methyl |
| 2509-11 | R-isobutyl | R-cyclohexyl | R-isopropyl | 4-tbutyl-cyclohexyl-methyl |
| 2509-12 | R-isobutyl | R-cyclohexyl | R-isopropyl | 4-methylpentyl |
| 2509-13 | R-isobutyl | R-benzyl | (S,R)-1-hydroxyethyl | adamantan-1-yl-methyl |
| 2509-14 | R-isobutyl | R-benzyl | (S,R)-1-hydroxyethyl | 4-tbutyl-cyclohexyl-methyl |
| 2509-15 | R-isobutyl | R-benzyl | (S,R)-1-hydroxyethyl | 4-methylpentyl |
| 2509-16 | R-isobutyl | R-benzyl | R-propyl | adamantan-1-yl-methyl |
| 2509-17 | R-isobutyl | R-benzyl | R-propyl | 4-tbutyl-cyclohexyl-methyl |
| 2509-18 | R-isobutyl | R-benzyl | R-propyl | 4-methylpentyl |
| 2509-19 | R-isobutyl | R-benzyl | R-isopropyl | adamantan-1-yl-methyl |
| 2509-20 | R-isobutyl | R-benzyl | R-isopropyl | 4-tbutyl-cyclohexyl-methyl |
| 2509-21 | R-isobutyl | R-benzyl | R-isopropyl | 4-methylpentyl |
| 2509-22 | R-isopropyl | R-cyclohexyl | (S,R)-1-hydroxyethyl | adamantan-1-yl-methyl |
| 2509-23 | R-isopropyl | R-cyclohexyl | (S,R)-1-hydroxyethyl | 4-tbutyl-cyclohexyl-methyl |
| 2509-24 | R-isopropyl | R-cyclohexyl | (S,R)-1-hydroxyethyl | 4-methylpentyl |
| 2509-25 | R-isopropyl | R-cyclohexyl | R-propyl | adamantan-1-yl-methyl |
| 2509-26 | R-isopropyl | R-cyclohexyl | R-propyl | 4-tbutyl-cyclohexyl-methyl |
| 2509-27 | R-isopropyl | R-cyclohexyl | R-propyl | 4-methylpentyl |
| 2509-28 | R-isopropyl | R-cyclohexyl | R-isopropyl | adamantan-1-yl-methyl |
| 2509-29 | R-isopropyl | R-cyclohexyl | R-isopropyl | 4-tbutyl-cyclohexyl-methyl |
| 2509-30 | R-isopropyl | R-cyclohexyl | R-isopropyl | 4-methylpentyl |
| 2509-31 | R-isopropyl | R-benzyl | (S,R)-1-hydroxyethyl | adamantan-1-yl-methyl |
| 2509-32 | R-isopropyl | R-benzyl | (S,R)-1-hydroxyethyl | 4-tbutyl-cyclohexyl-methyl |
| 2509-33 | R-isopropyl | R-benzyl | (S,R)-1-hydroxyethyl | 4-methylpentyl |
| 2509-34 | R-isopropyl | R-benzyl | R-propyl | adamantan-1-yl-methyl |
| 2509-35 | R-isopropyl | R-benzyl | R-propyl | 4-tbutyl-cyclohexyl-methyl |
| 2509-36 | R-isopropyl | R-benzyl | R-propyl | 4-methylpentyl |
| 2509-37 | R-isopropyl | R-benzyl | R-isopropyl | adamantan-1-yl-methyl |
| 2509-38 | R-isopropyl | R-benzyl | R-isopropyl | 4-tbutyl-cyclohexyl-methyl |
| 2509-39 | R-isopropyl | R-benzyl | R-isopropyl | 4-methylpentyl |
| 2509-40 | R-2-butyl | R-benzyl | R-4-hydroxybenzyl | 4-tbutyl-cyclohexyl-methyl |

Tables 2b and 2c tabulate the results observed for the activation of the melanocortin-1, -3, -4 and -5 receptors. The complete set of dose-response curves observed for each of the compounds at the four receptor subtypes are illustrated in FIGS. 4A-H, 5A-H, 6A-H, and 7A-H.

TABLE 2b

Summary of Agonist Activity Observed at the mouse Melanocortin-1, and -5 Receptor Subtypes

| | mMC1R | | mMC5R | |
|---|---|---|---|---|
| Compound/TPI # | Mean ± SEM | Activity @ 10 μM | Mean ± SEM | Activity @ 10 μM |
| NDP-MSH [(Nle[4], DPhe[7]) α-MSH] | 0.09 ± 0.03 | | 2.6 ± 0.6 | |
| Ac-His-DPhe-Arg-Trp-NH$_2$ | 13.4 ± 3.9 | | 4.2 ± 1 | |
| 2509-4 | 330 ± 110 | | 340 ± 140 | |
| 2509-5 | 300 ± 90 | | 140 ± 70 | |
| 2509-6 | 7300 ± 4400 | | 630 ± 50 | |
| 2509-7 | | 70% B | 470 ± 90 | |
| 2509-8 | 500 ± 50 | | 530 ± 50 | |
| 2509-9 | 2300 ± 90 | | 1800 ± 130 | |
| 2509-10 | 570 ± 150 | | 500 ± 40 | |
| 2509-11 | | 54% B | 560 ± 50 | |
| 2509-12 | | 50% B | 1850 ± 800 | |
| 2509-13 | | 41% B | 810 ± 280 | |
| 2509-14 | | 58% B | 530 ± 50 | |
| 2509-15 | | 62% B | | 77% B |
| 2509-16 | 7000 ± 6100 | | 610 ± 160 | |
| 2509-17 | | 38% A | 480 ± 170 | |
| 2509-18 | | | 2180 ± 625 | |
| 2509-19 | 15500 ± 14000 | | 440 ± 110 | |
| 2509-20 | 6800 ± 600 | | 560 ± 170 | |
| 2509-21 | | | 1260 ± 130 | |
| 2509-22 | 200 ± 80 | | 600 ± 210 | |
| 2509-23 | 300 ± 120 | | 150 ± 20 | |
| 2509-24 | 700 ± 80 | | 740 ± 270 | |
| 2509-25 | 550 700 ± 80 170 | | 590 ± 180 | |
| 2509-26 | | B | 540 ± 50 | |
| 2509-27 | | B | 1040 ± 150 | |
| 2509-28 | 300 ± 30 | | 580 ± 160 | |
| 2509-29 | 290 ± 20 | | 510 ± 50 | |
| 2509-30 | 6100 700 ± 80 4700 | | 1700 ± 520 | |
| 2509-31 | 440 ± 140 | | 180 ± 90 | |
| 2509-32 | 600 ± 340 | | 490 ± 155 | |
| 2509-33 | | B | | 40% A |
| 2509-34 | 6700 ± 4700 | | 6600 ± 5740 | |
| 2509-35 | 2300 ± 1000 | | 940 ± 340 | |
| 2509-36 | 22900 ± 10000 | | 2030 ± 980 | |
| 2509-37 | 47800 ± 23100 | | 660 ± 130 | |
| 2509-38 | 29100 ± 20000 | | 600 ± 170 | |
| 2509-39 | 10220 ± 6570 | | 1600 ± 460 | |
| 2509-40 | 290 ± 20 | | 380 ± 50 | |

A: <50%
B: >51%
PA: full partial agonist plateau response to generate valid EC50

TABLE 2c

Summary of Agonist Activity Observed at the mouse Melanocortin-3, and -4 Receptor Subtypes

| | mMC3R | | mMC4R | | mMC4R Antagonist |
|---|---|---|---|---|---|
| Compound/TPI # | Mean ± SEM | Activity @ 10 μM | Mean ± SEM | Activity @ 10 μM | pA2 |
| NDP-MSH [(Nle[4], DPhe[7]) α-MSH] | 0.36 ± 0.04 | | 0.12 ± 0.01 | | |
| Ac-His-DPhe-Arg-Trp-NH$_2$ | 31 ± 9 | | 5.5 ± 0.8 | | |
| 2509-4 | 240 ± 40 | | | 55% PA | pA2 = 5.5 ± 1.1 |
| 2509-5 | 210 ± 50 | | | 45% PA | pA2 = 5.8 ± 0.08 |
| 2509-6 | | 58% B | | A | |
| 2509-7 | | 67% B | | 51% A | |
| 2509-8 | | 75% B | | 65% B | |
| 2509-9 | | 58% B | 6700 ± 2400 | | |
| 2509-10 | | 70% B | | 50% A | |
| 2509-11 | | 69% B | | | |
| 2509-12 | | 33% A | | B | |
| 2509-13 | 360 ± 40 | | | 58% B | pA2 = 5.6 ± 0.2 |
| 2509-14 | 310 ± 60 | | | A | pA2 = 7.0 ± 0.7 |
| 2509-15 | | | | | |

TABLE 2c-continued

Summary of Agonist Activity Observed at the mouse Melanocortin-3, and -4 Receptor Subtypes

| Compound/TPI # | mMC3R Mean ± SEM | mMC3R Activity @ 10 μM | mMC4R Mean ± SEM | mMC4R Activity @ 10 μM | mMC4R Antagonist pA2 |
|---|---|---|---|---|---|
| 2509-16 | | 74% B | 1330 ± 510 | | |
| 2509-17 | | 83% B | | 28% A | |
| 2509-18 | | | | B | |
| 2509-19 | | 67% B | 8200 ± 3550 | | |
| 2509-20 | | 62% B | | | |
| 2509-21 | | A | | A | |
| 2509-22 | 370 ± 90 | | | 49% A | pA2 = 5.8 ± 0.1 |
| 2509-23 | 220 ± 30 | | | 41% A | pA2 = 5.9 ± 0.03 |
| 2509-24 | 5200 ± 1540 | | | | |
| 2509-25 | 2800 ± 1800 | | | 45% A | |
| 2509-26 | 350 ± 20 | | | 50% A | pA2 = 5.8 ± 0.2 |
| 2509-27 | | B | | 40% A | |
| 2509-28 | 3700 ± 880 | | | 40% A | |
| 2509-29 | 4300 ± 3300 | | | 28% A | |
| 2509-30 | | B | | B | |
| 2509-31 | 360 ± 10 | | | 50% PA | pA2 = 5.8 ± 0.04 |
| 2509-32 | 420 ± 120 | | | A | pA2 = 6.5 ± 0.5 |
| 2509-33 | | | | | |
| 2509-34 | 2000 ± 850 | | 1400 ± 760 | | |
| 2509-35 | 6200 ± 5400 | | | 27% A | |
| 2509-36 | | | | 41% A | |
| 2509-37 | 4000 ± 1900 | | | 54% B | |
| 2509-38 | | 68% B | | | |
| 2509-39 | | | | 21% A | |
| 2509-40 | | 65% B | | 23% A | |

A: <50%
B: >51%
PA: full partial agonist plateau response to generate valid EC50

Example 4. In Vivo Murine Studies

The ability of the compounds of the invention to affect metabolic activity and/or food intake may be tested using in vivo feeding studies in mice. Specially developed mice (e.g., wild-type, melanocortin-3 receptor knockout, melanocortin-4 receptor knockout, and melanocortin-3/4 receptor double knockout) may be injected with a compound of the invention and any possible effects on food intake and metabolic activity may be assessed.

Example 5. The Following Illustrate Representative Pharmaceutical Dosage Forms, Containing a Compound of Formula I ('Compound X'), for Therapeutic or Prophylactic Use in Humans

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X= (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X= (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

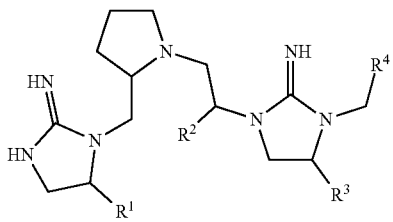

I wherein:

$R^1$ is H, or $C_{1-30}$ alkyl; wherein the $C_{1-30}$ alkyl is optionally substituted with one or more groups selected from the group consisting of halo, hydroxy, nitro, cyano, $C_{1-6}$ alkoxy, $-NR^a_2$, $-NHC(=NH)NR^a_2$, $-C(=O)NR^a_2$, $-COOR^a$, and $-SR^a$;

$R^2$ is H, $C_{1-8}$ alkyl or $-L^2-A^2$; wherein the $C_{1-8}$ alkyl is optionally substituted with one or more groups selected from the group consisting of halo, hydroxy, nitro, cyano, $C_{1-6}$ alkoxy, $-NR^b_2$, $-NHC(=NH)NR^b_2$, $-C(=O)NR^b_2$, $-COOR^b$, and $-SR^b$;

$R^3$ is H, or $C_{1-30}$ alkyl; wherein the $C_{1-30}$ alkyl is optionally substituted with one or more groups selected from the group consisting of halo, hydroxy, nitro, cyano, $C_{1-6}$ alkoxy, $-NR^c_2$, $-NHC(=NH)NR^c_2$, $-C(=O)NR^c_2$, $-COOR^c$, and $-SR^c$;

$R^4$ is H, $C_{1-30}$ alkyl or $-L^4-A^4$; wherein the $C_{1-30}$ alkyl is optionally substituted with one or more groups selected from the group consisting of halo, hydroxy, nitro, cyano, $C_{1-6}$ alkoxy, $-NR^d_2$, $-NHC(=NH)NR^d_2$, $-C(=O)NR^d_2$, $-COOR^d$, and $-SR^d$;

$L^2$ is absent or $C_{1-4}$ alkylene;

$L^4$ is absent or $C_{1-4}$ alkylene;

$A^2$ is cycloalkyl, aryl, or heteroaryl; wherein the cycloalkyl, aryl, and heteroaryl are optionally substituted with one or more groups selected from the group consisting of halo, hydroxy, nitro, cyano, $C_{1-6}$ alkyl, $C_{1-6}$ alkoxy, $C_{1-6}$ haloalkyl, $C_{1-6}$ haloalkoxy, and phenyl;

$A^4$ is cycloalkyl; wherein the cycloalkyl is optionally substituted with one or more groups selected from the group consisting of halo, hydroxy, nitro, cyano, $C_{1-6}$ alkyl, $C_{1-6}$ alkoxy, $C_{1-6}$ haloalkyl, $C_{1-6}$ haloalkoxy, and phenyl;

each $R^a$ is independently H or $C_{1-6}$ alkyl;

each $R^b$ is independently H or $C_{1-6}$ alkyl;

each $R^c$ is independently H or $C_{1-6}$ alkyl; and each $R^d$ is independently H or $C_{1-6}$ alkyl;

or a salt thereof.

2. The compound of claim 1 which is a compound of formula Ia:

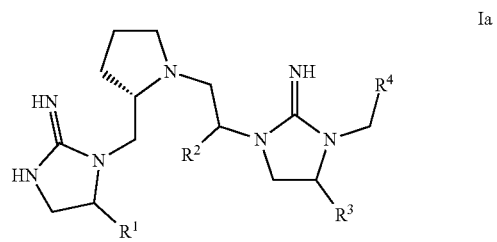

Ia or a salt thereof.

3. The compound of claim 1, wherein $R^1$ is selected from the group consisting of:

a) a side chain of an amino acid selected from the group consisting of: D-Leu, D-Val, D-Ile, D-Nle, D-Nva, D-Thr, D-Ala, Gly, Ala, D-Ser, Val, Nva, Thr, Leu, Nle, Ile, and Ser; and b) $C_{1-30}$ alkyl, substituted with one or more COOH.

4. The compound of claim 1, wherein $R^2$ is a side chain of an amino acid having 1 to 12 carbon atoms and 0 to 4 heteroatoms selected from the group consisting of oxygen, nitrogen and sulfur.

5. The compound of claim 4, wherein the amino acid is selected from the group consisting of: D-Cha, Cha, D-Nle, D-Phe, D-Ser, D-Leu, D-Nva, Ala(2-naphtyl), Ser, Phg, D-Ala(2-naphtyl), Val, Ile, D-Thr, Nle, Tyr, D-Tyr, D-Ile, D-Ala, Ala, D-Val, Phe, Nva, Gly, and Thr.

6. The compound of claim 1, wherein:

$R^2$ is $-L^2-A^2$;

$L^2$ is $C_{1-4}$ alkylene; and $A^2$ is cycloalkyl or aryl.

7. The compound of claim 1, wherein $R^2$ is:

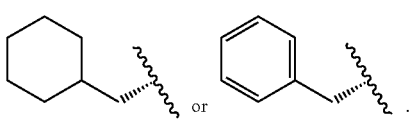

8. The compound of claim 1, wherein $R^3$ is a side chain of an amino acid selected from the group consisting of: D-Thr, D-Nva, D-Val, D-Ile, Gly, D-Ala, D-Leu, D-Nle, D-Ser, Ala, Nle, Thr, Val, Nva, Ile, and Leu.

9. The compound of claim 1, wherein $R^3$ is $C_{1-8}$ alkyl which is optionally substituted with hydroxy.

10. The compound of claim 1, wherein:

$R^4$ is $C_{1-8}$ alkyl or $-L^4-A^4$;

$L^4$ is absent or $C_{1-4}$ alkylene; and $A^4$ is cycloalkyl; wherein the cycloalkyl is optionally substituted with one or more groups selected from the group consisting of halo, hydroxy, $C_{1-6}$ alkyl, $C_{1-6}$ alkoxy, $C_{1-6}$ haloalkyl, and phenyl.

11. The compound of claim 1, wherein $R^4$ is selected from the group consisting of:

—CH$_2$CH$_2$CH(CH$_3$)$_2$,

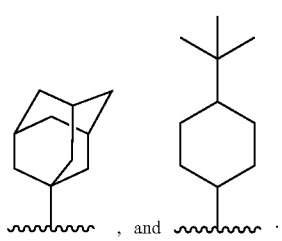 [SMILES: *C12CC3CC(CC(C3)C1)C2 ; *C1CCC(C(C)(C)C)CC1]

, and

12. The compound of claim 1 which is selected from the group consisting of:

TPI 2509-4

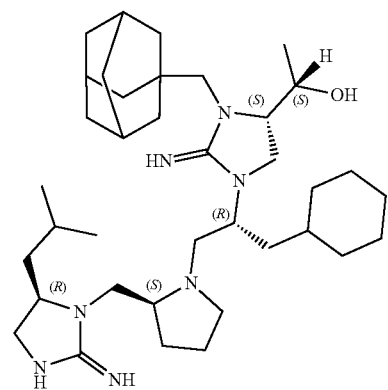

TPI 2509-5

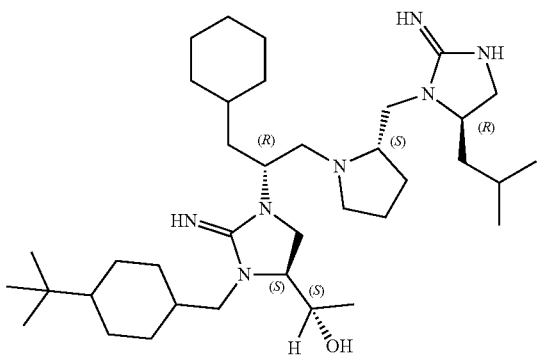

TPI 2509-6

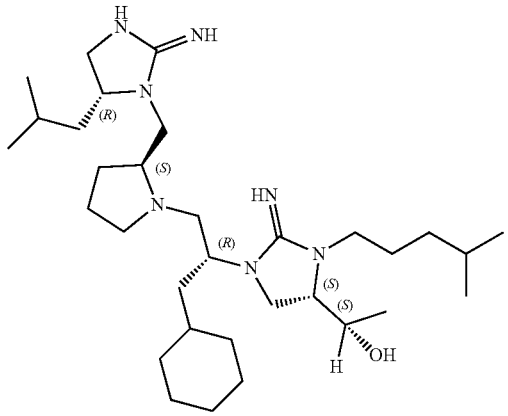

TPI 2509-7

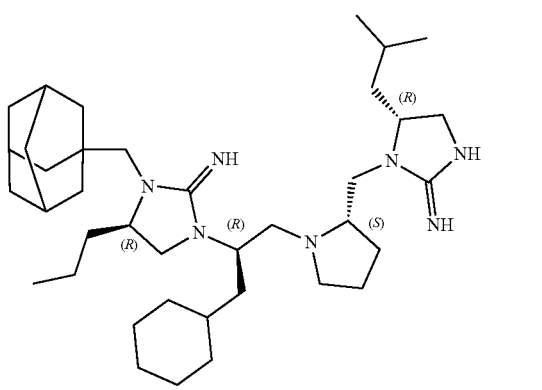

TPI 2509-8

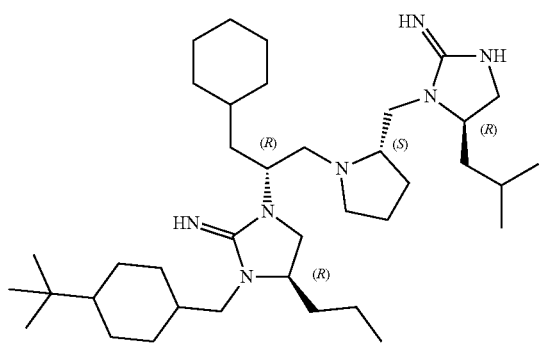

TPI 2509-9

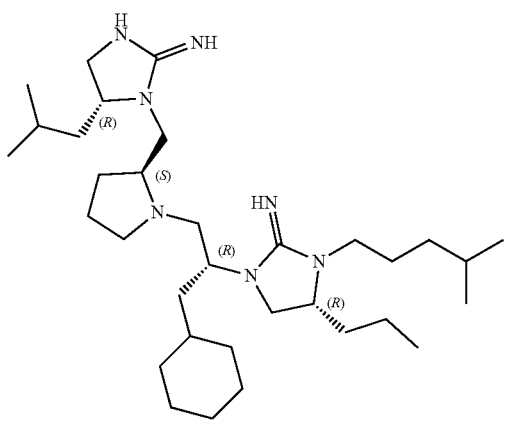

-continued
TPI 2509-10
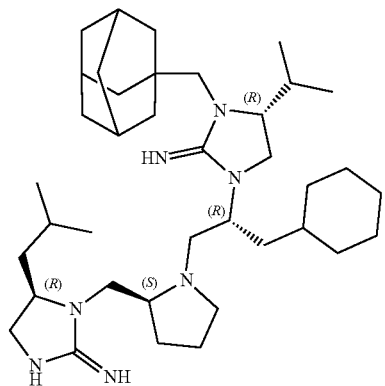
TPI 2509-11
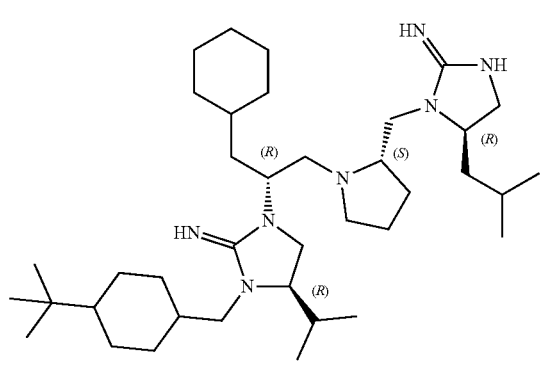
TPI 2509-12
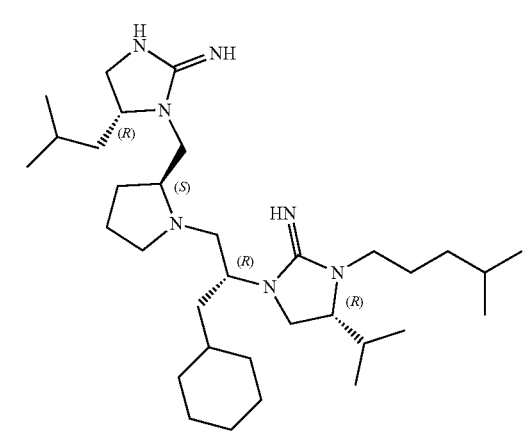
TPI 2509-13
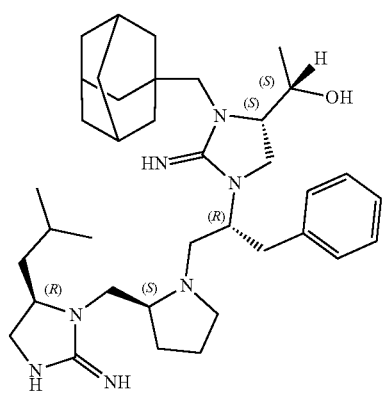
-continued
TPI 2509-14
TPI 2509-15
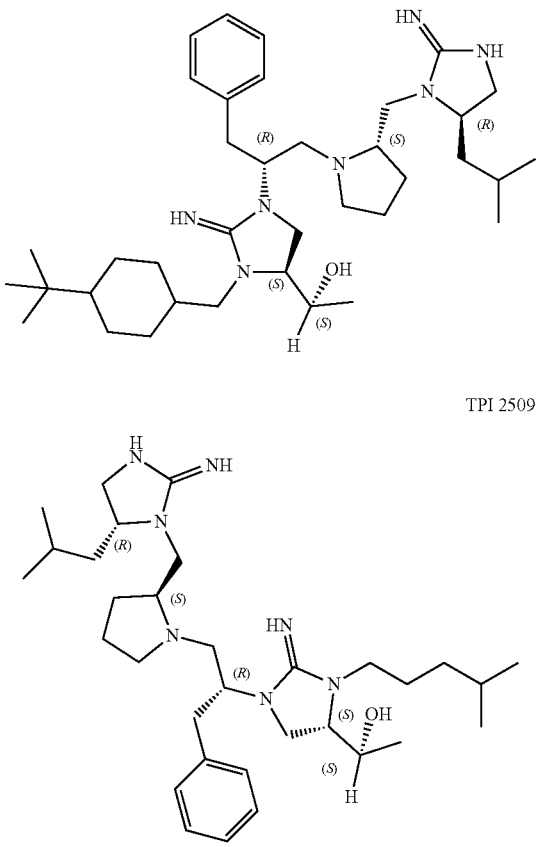
TPI 2509-16
TPI 2509-17
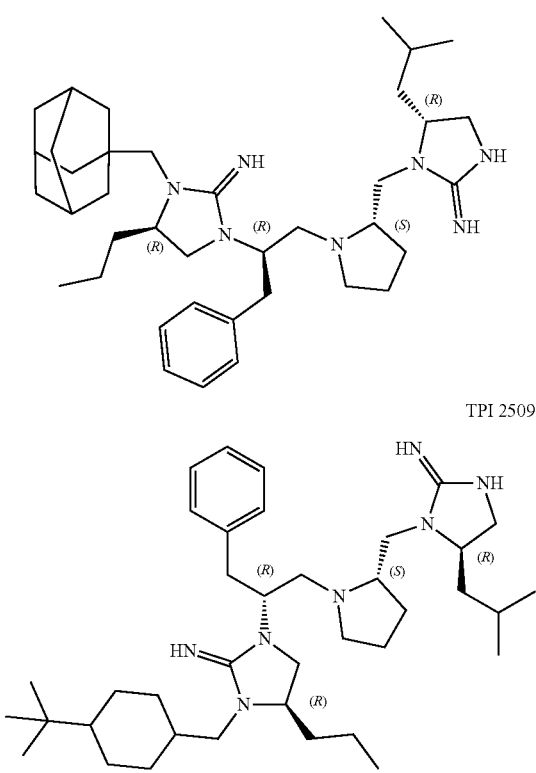

TPI 2509-18
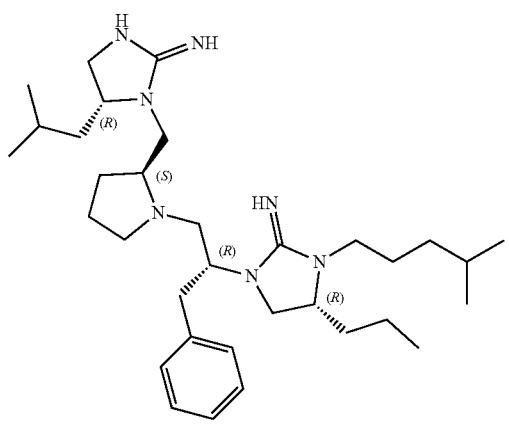
TPI 2509-19
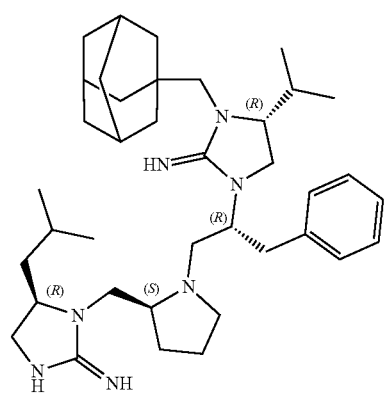
TPI 2509-20
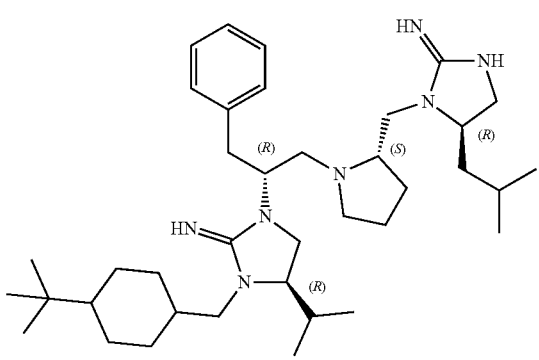
TPI 2509-21
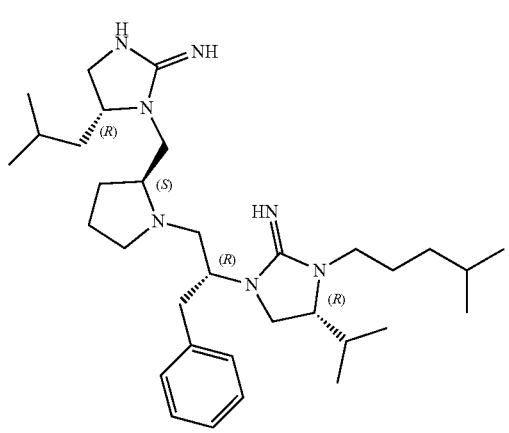
TPI 2509-22
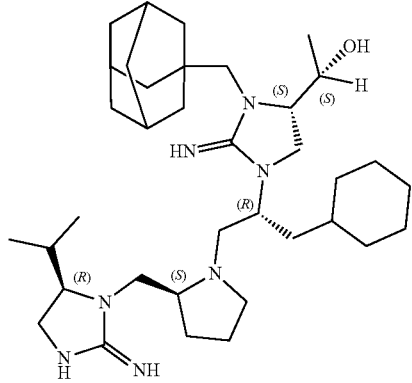
TPI 2509-23
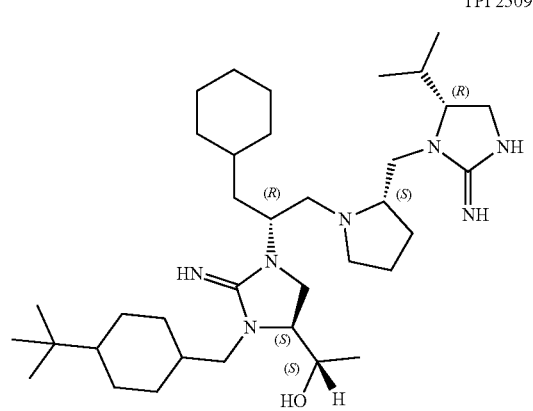
TPI 2509-24
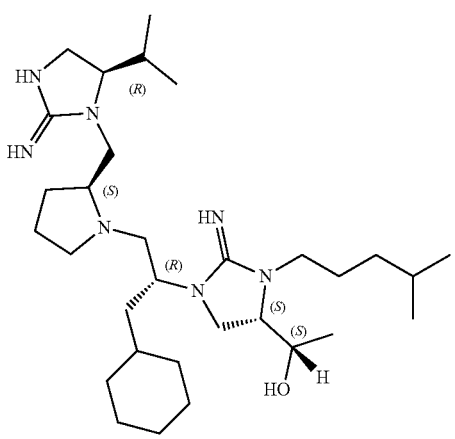
TPI 2509-25
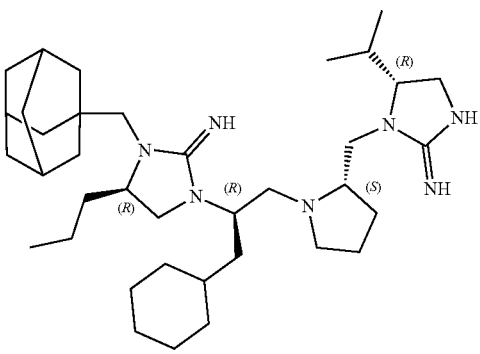

TPI 2509-26
TPI 2509-27
TPI 2509-28
TPI 2509-29
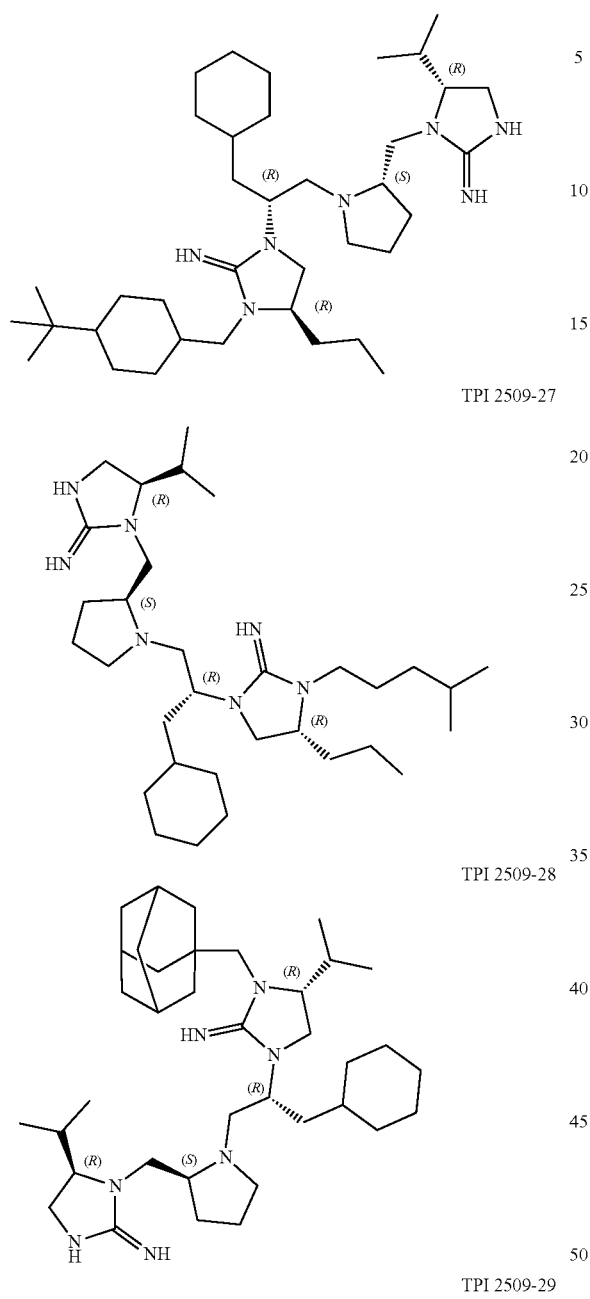
TPI 2509-30
TPI 2509-31
TPI 2509-32
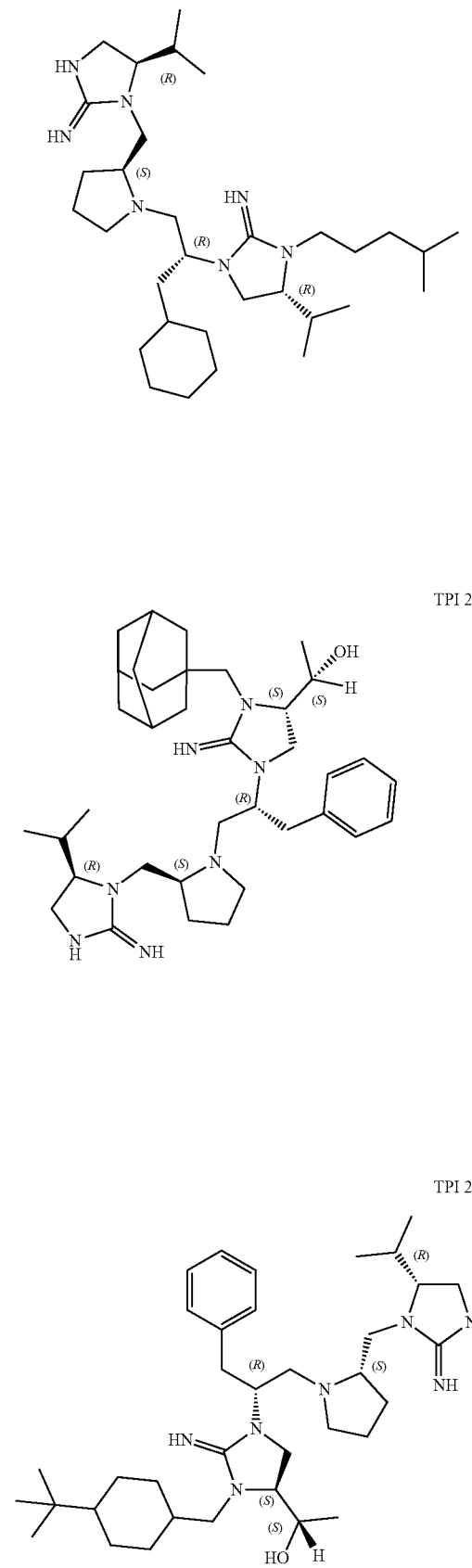

-continued
TPI 2509-33
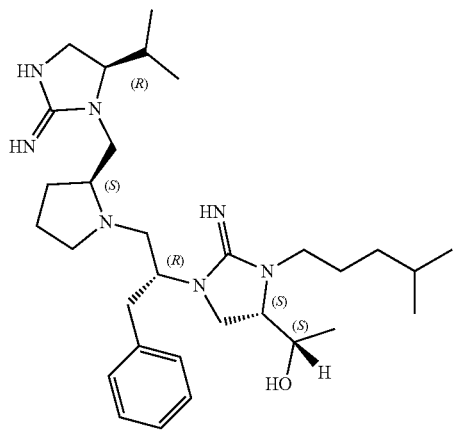
TPI 2509-34
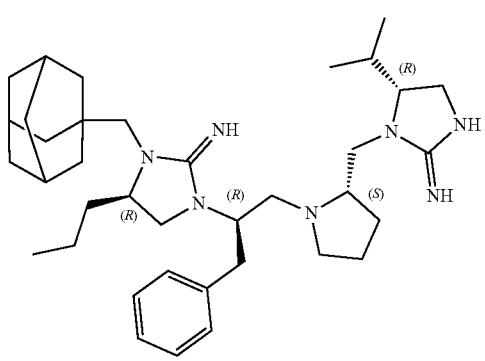
TPI 2509-35
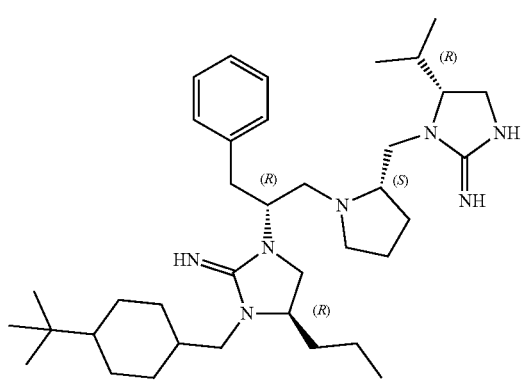
-continued
TPI 2509-36
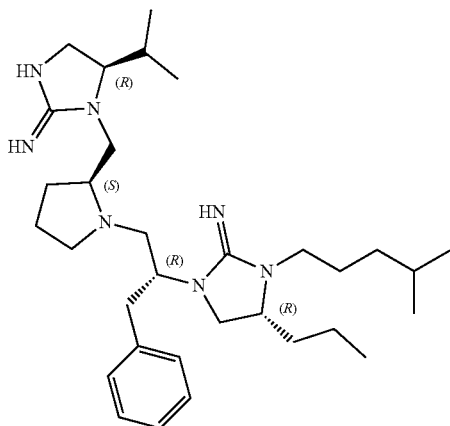
TPI 2509-37
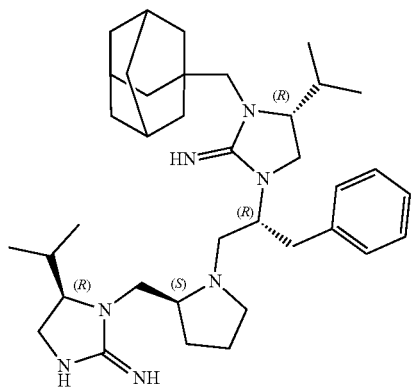
TPI 2509-38
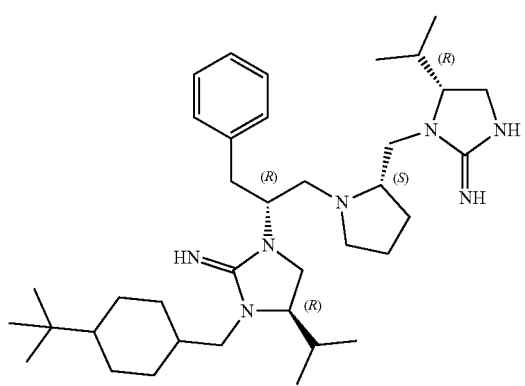

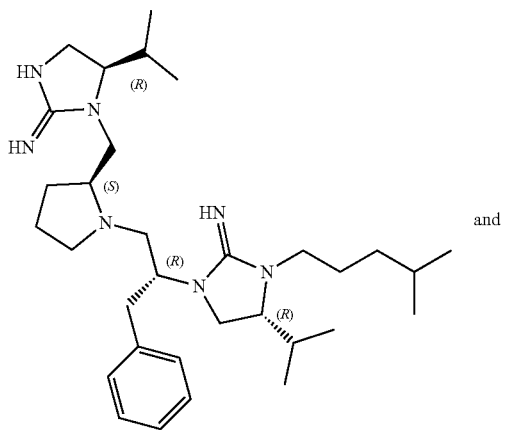

TPI 2509-39 and

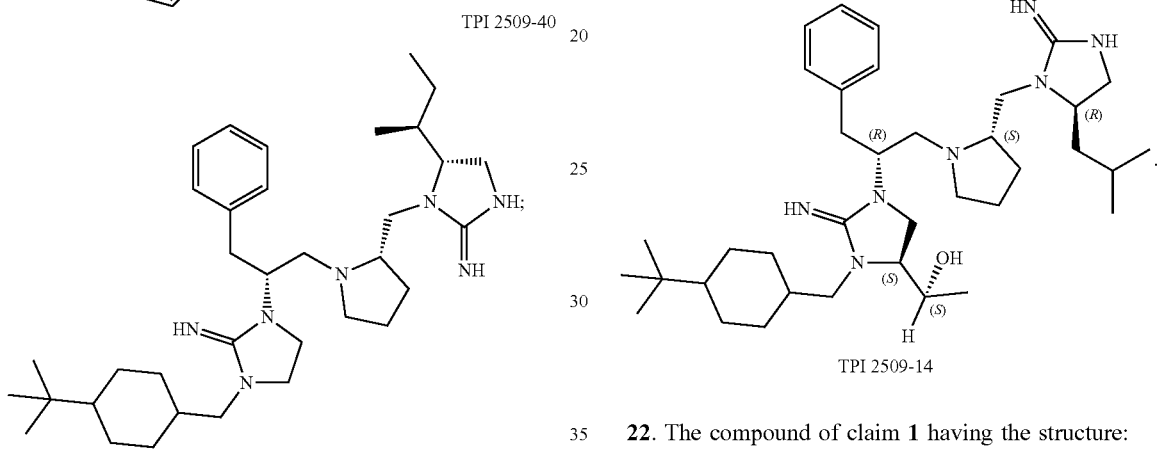

TPI 2509-40 or a salt thereof.

13. A pharmaceutical composition comprising a compound of formula I as described in claim 1, or a pharmaceutically acceptable salt thereof, and a pharmaceutically acceptable excipient.

14. A dietary supplement comprising a compound of formula I as described in claim 1, or a salt thereof.

15. A method of treating obesity, anorexia, cachexia, failure to thrive, modulation of food intake and the desire to eat or a disease associated with obesity, anorexia, cachexia, failure to thrive, modulation of food intake and the desire to eat in humans or in an animal in need thereof, comprising administering an effective amount of a compound of formula I as described in claim 1, or a pharmaceutically acceptable salt thereof, to the human or animal.

16. The method of claim 15, wherein the disease associated with obesity is diabetes, cardiovascular disease or hypertension.

17. A method of modulating the activity of a melanocortin receptor in vitro or in vivo comprising contacting the receptor with an effective amount of a compound of formula I as described in claim 1, or a pharmaceutically acceptable salt thereof.

18. The method of claim 17, wherein the melanocortin receptor is melanocortin-3 receptor (MC3R).

19. A method of selectively activating melanocortin-3 receptor (MC3R) over melanocortin-4 receptor (MC4R) in vitro or in vivo comprising contacting the receptors with an effective amount of a compound of formula I as described in claim 1, or a pharmaceutically acceptable salt thereof.

20. A method of modulating appetite in an animal in need thereof, comprising administering an effective amount of a compound of formula I as described in claim 1, or a pharmaceutically acceptable salt thereof, to the animal.

21. The compound of claim 1 having the structure:

TPI 2509-14

22. The compound of claim 1 having the structure:

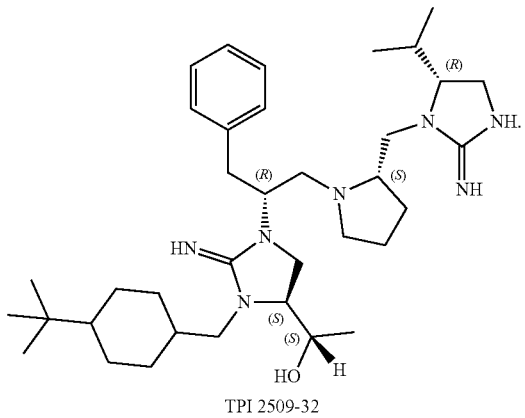

TPI 2509-32

* * * * *